(12) United States Patent
Leblond et al.

(10) Patent No.: US 9,446,044 B2
(45) Date of Patent: Sep. 20, 2016

(54) DYRK1 INHIBITORS AND USES THEREOF

(75) Inventors: Bertrand Leblond, Paris (FR);
Anne-Sophie Casagrande, Draveil (FR); Laurent Desire, Paris (FR); Alicia Foucourt, Canteleu (FR); Thierry Besson, Preaux (FR)

(73) Assignee: DIAXONHIT, Paris (FR)

( * ) Notice: Subject to any disclaimer, the term of this patent is extended or adjusted under 35 U.S.C. 154(b) by 0 days.

(21) Appl. No.: 14/238,925

(22) PCT Filed: Aug. 17, 2012

(86) PCT No.: PCT/EP2012/066151
§ 371 (c)(1),
(2), (4) Date: May 30, 2014

(87) PCT Pub. No.: WO2013/026806
PCT Pub. Date: Feb. 28, 2013

(65) Prior Publication Data
US 2014/0275064 A1    Sep. 18, 2014

(30) Foreign Application Priority Data
Aug. 19, 2011    (EP) .................................... 11178190

(51) Int. Cl.
| A61K 31/5377 | (2006.01) |
| C07D 513/04 | (2006.01) |
| A61K 31/519 | (2006.01) |
| C07C 271/28 | (2006.01) |
| C07D 277/68 | (2006.01) |
| C07C 219/04 | (2006.01) |
| C07D 277/64 | (2006.01) |

(52) U.S. Cl.
CPC ......... *A61K 31/519* (2013.01); *A61K 31/5377* (2013.01); *C07C 219/04* (2013.01); *C07C 271/28* (2013.01); *C07D 277/64* (2013.01); *C07D 277/68* (2013.01); *C07D 513/04* (2013.01)

(58) Field of Classification Search
CPC .................... A61K 31/5377; C07D 513/04
See application file for complete search history.

(56) References Cited

FOREIGN PATENT DOCUMENTS
| GB | 2447791 | 9/2008 |
| WO | WO 95/19970 | 7/1995 |

OTHER PUBLICATIONS

Ferrer, I., et al. "Constitutive Dyrk1A is abnormally expressed in Alzheimer disease, Down syndrome, Pick disease, and related transgenic models." Neurobiology of Disease. (2005), vol. 20, pp. 392-400.*
Janel, N., et al. "Plasma DYRK1A as a novel risk factor for Alzheimer's disease." Transl. Psychiatry. (2014), vol. 4, pp. 1-7.*
Costa, A.C., et al. "Prospects for Improving Brain Function in Individuals with Down Syndrome." CNS Drug. (2013), pp. 1-24.*
Hedou, D., et al. "Design and Synthesis of Thiazolo[5,4-f]quinazolines as DYRK1A Inhibitors, Part I." Molecules. (2014), vol. 19, pp. 15546-15571.*
Royal Society of Chemistry. ChemSpider. "(−)-Epigallocatechin gallate." (c) 2015. Available from: < http://www.chemspider.com/Chemical-Structure.58575.html >.*
De la Torre, et al. "Epigallocatechin-3-gallate, a DYRK1A inhibitor, rescues cognitive deficits in Down syndrome mouse models and in humans." Mol. Nutr. Food Res. (2013), 00, pp. 1-11.*
Guedj, F., et al. "Green Tea Polyphenols Rescue of Brain Defects Induced by Overexpression of DYRK1A." PLoS One. (Feb. 2009), vol. 4, Issue 2, pp. 1-8.*
Morrice, A. G. et al, "The Angular Benzoadenines. 9-Aminoimidazo[4,5-*f*]quinazoline and 6-Aminoimidazo[4,5-*h*]quinazoline" *Journal of Organic Chemistry*, Jan. 1, 1975, pp. 363-366, vol. 40, No. 3.
Rewcastle, G. W. et al. "Tyrosine Kinase Inhibitors. 9. Synthesis and Evaluation of Fused Tricyclic Quinazoline Analogues as ATP Site Inhibitors of the Tyrosine Kinase Activity of the Epidermal Growth Factor Receptor" *Journal of Medicinal Chemistry*, Jan. 1, 1996, pp. 918-928, vol. 39, No. 4.
Showalter, H. D. et al. "Tyrosine Kinase Inhibitors. 16. 6,5,6-Tricyclic Benzothieno[3,2-*d*]pyrimidines and Pyrimido[5,4-*b*]- and -[4,5-*b*]indoles as Potent Inhibitors of the Epidermal Growth Factor Receptor Tyrosine Kinase" *Journal of Medicinal Chemistry*, Jan. 1, 1999, pp. 5464-5474, vol. 42, No. 26.
Beck, G. et al. "Nucleophile Substitution an chlorierten Mono- und Dicyan-benzolen" *Justus Liebigs Annalen Der Chemie*, 1968, pp. 47-60, vol. 716.
Written Opinion in International Application No. PCT/EP2012/066151, Oct. 24, 2012, pp. 1-7.

* cited by examiner

*Primary Examiner* — Noble Jarrell
*Assistant Examiner* — John S Kenyon
(74) *Attorney, Agent, or Firm* — Saliwanchik, Lloyd & Eisenschenk

(57) ABSTRACT

The present invention relates to novel thiazolo[5,4-f]quinazoline compounds and methods that are useful in the amelioration, treatment or control of Down's syndrome or early Alzheimer's disease or in the amelioration, treatment or control of cancers, especially solid tumors. More specifically, the invention relates to DYRK1A and/or DYRK1B inhibitors and to methods for preparing such compounds.

10 Claims, No Drawings

DYRK1 INHIBITORS AND USES THEREOF

CROSS-REFERENCE TO RELATED APPLICATION

This application is the U.S. national stage application of International Patent Application No. PCT/EP2012/066151, filed Aug. 17, 2012.

FIELD OF THE INVENTION

The present invention relates to novel thiazolo[5,4-f] quinazoline compounds and methods that are useful in the amelioration, treatment or control of Down's syndrome or early Alzheimer's disease or in the amelioration, treatment or control of cancers, especially solid tumors. More specifically, the invention relates to DYRK1A and/or DYRK1B inhibitors and to methods for preparing such compounds.

BACKGROUND OF THE INVENTION

Protein kinases are enzymes which catalyze protein phosphorylation, a key cellular regulatory mechanism which is frequently deregulated in human diseases. Consequently, protein kinases represent interesting targets for the pharmaceutical industry in its search for new therapeutic agents. 518 Human protein kinase genes have been identified in the human kinome (Manning G. et al., Science, 2002, 298, 1912-34). It is well known that protein kinases are key elements in intracellular signaling pathways that control many physiological processes. Most kinases act on both serine and threonine, others act on tyrosine, and a number (dual-specificity kinases) act on all three.

Dual-specificity tyrosine-regulated kinases (DYRKs) comprise a family of protein kinases within the CMGC group of the eukaryotic kinome (CMGC: cyclin-dependent kinases (CDKs), mitogen-activated protein kinases (MAPKs), glycogen synthase kinases (GSKs), and CDK-like kinases (CLKs). The DYRK family comprises five members in humans, DYRK1A, DYRK1B, DYRK2, DYRK3, and DYRK4 (Becker et al., J. Biol. Chem., 1998, 273(40), 25893-902).

DYRK1A may play a significant role in a signaling pathway regulating cell proliferation and may be involved in brain development.

Expression of DYRK1A is detected in several regions of the central nervous system, from development to adulthood, especially in the cortex, hippocampus and cerebellum. Dyrk1A knock-out mice are embryonic lethal and transgenic mice overexpressing Dyrk1A display learning and memory deficiencies. The human DYRK1A gene has been implicated in the pathogenesis of Down syndrome due to its location on the Down syndrome (DS) critical region of the human chromosome 21 and is present in three copies in DS patients. Trisomy-driven overexpression in DS patients has been demonstrated and DYRK1A overexpression in DS is also associated with early Alzheimer's disease (AD) phenotype observed in DS patients.

In DS, the pathogenetic role of enhanced activity of DYRK1A in both neurodevelopment and neurodegeneration makes it a target for therapeutic intervention for cognitive improvement and neuroprotection. However, a number of studies (Kimura et al., Hum. Mol. Genet., 2007, 16(1), 15-23, and Wegiel et al., FEBS J., 2011, 278(2), 236-45 for review) indicate that overexpression of DYRK1A could be a primary risk factor contributing to the enhancement of both amyloidosis and neurofibrillary degeneration seen in DS, but also AD and other neurodegenerative diseases. Moreover, elevated levels of Aβ peptide may upregulate DYRK1A expression and enhance the contribution of overexpressed DYRK1A to neurofibrillary degeneration and beta-amyloidosis.

DYRK1A phosphorylates key players in AD, namely, APP, Tau, presenilin, and septin-4, DYRK1A acts as a priming kinase, allowing its substrates to be further phosphorylated by GSK3, a key kinase in AD.

Elevated Aβ levels detected in the hippocampus of DYRK1A transgenic mice and in the brain of DS and AD patients suggest that DYRK1A overexpression promotes APP cleavage and Aβ production. Recent studies by Ryoo et al. (J. Neurochem., 2008, 104(5), 1333-44) revealed that DYRK1A phosphorylates APP at Thr668 in vitro and in mammalian cells. Elevated levels of phospho-APP are observed in AD, particularly in the hippocampus. The phosphorylation of APP at Thr668 may facilitate the cleavage of APP by BACE1 and gamma-secretase and enhance the production of Aβ (Vingtdeux et al., Neurobiol. Dis., 2005, 20(2), 625-37). Dyrk1A may also contribute to Aβ production by controlling PS1 phosphorylation at Thr(354). Elevated Aβ levels are detected in the hippocampus of DYRK1A transgenic mice and in the brain of DS patients, suggesting that DYRK1A overexpression promotes APP cleavage and Aβ production. Inhibition of DYRK1A may thus be particularly useful for the regulation or reduction of the formation of Aβ peptide and consequently, the reduction of beta amyloid plaque formation on the brain. Accordingly, DYRK1A can be useful for the treatment of AD and other amyloid-related disorders.

The hypothesis that the elevated activity of DYRK1A contributes to the cognitive deficits in Down syndrome and the development of Alzheimer's disease has stimulated interest in DYRK1A as a potential target for therapeutic inhibitors.

The human DYRK1B gene was mapped to chromosome 19 (19q12-13.11) by radiation hybrid analysis (Leder, S., et al., Biochem. Biophys. Res. Commun., 1999, 254(2), 474-9). The amino acid sequences of DYRK1A and DYRK1B are 84% identical in the N-terminus and the catalytic domain but show no extended sequence similarity in the C-terminal region. DYRK1B contains all motifs characteristic for the DYRK family of protein kinases. In addition, the sequence comprises a bipartite nuclear localization motif. DYRK1B is a muscle- and testis-specific isoform of DYRK1A and is involved in the regulation of nuclear functions.

The protein kinase DYRK1B (also referred to as MIRK) mediates survival and differentiation in many tissues. It is believed to be implicated in certain cancers, particularly solid tumors, see Gao J. et al., Cancer Biology & Therapy, 2009, 8:17, 1671-9 (lung cancer cells), Lee, K. et al., Cancer Research, 2000, 60, 3631-7 (colon cancer cells) and Deng, X. et al., Cancer Research, 2006, 66, 4149-58 (pancreatic cancer cells).

A major problem in the treatment of cancer arises from quiescent cancer cells that are relatively insensitive to most chemotherapeutic drugs and radiation. Such residual cancer cells can cause tumor regrowth or recurrence when they reenter the cell cycle. Earlier studies showed that levels of the serine/threonine kinase MIRK/DYRK1B are elevated up to 10-fold in quiescent G(0) tumor cells (Ewton, D. Z. et al., Mol. Cancer Ther., 2011, 10(11), 2104-14 and Friedman E., Sarcoma, 2011, 260757. Epub 2011 Apr. 13). MIRK/DYRK1B uses several mechanisms to block cell cycling, and MIRK/DYRK1B increases expression of antioxidant genes that decrease reactive oxygen species (ROS) levels and increase quiescent cell viability. MIRK/DYRK1B kinase inhibition elevated ROS levels and DNA damage detected by increased phosphorylation of the histone protein H2AX and by S-phase checkpoints. MIRK/DYRK1B kinase inhibitors increased cleavage of the apoptotic proteins PARP and caspase 3, and increased tumor cell kill several-fold by gemcitabine and cisplatin. A phenocopy of these effects occurred following MIRK/DYRK1B depletion, showing drug specificity. MIRK/DYRK1B knockout or depletion had no detectable effect on normal tissue, suggesting that the MIRK/DYRK1B kinase inhibitor could have a selective effect on cancer cells expressing elevated levels of MIRK/DYRK1B kinase (e.g. lung cancer cells, colon cancer cells, pancreatic cancer cells, ovarian cancer cells, osteosarcoma cells, and rhabdomyosarcoma cells).

Two plant compounds, epigallocatechin-gallate (EGCG) and harmine, have been identified as DYRK1A inhibitors in selectivity profiling studies (Bain et al., Biochem., 2003, 371, 199) (Table 1). EGCG was used in cell culture studies to confirm the presumed role of DYRK1A in signalling events and to rescue brain defects of DYRK1A-overexpressing mice (Guedj et al., PLoS ONE, 2009, 4, 4606). A clinical trial was set-up to investigate the clinical benefits and safety of EGCG administration in young adults with DS, to establish short-term EGCG effects (three months) on neurocognitive performance, and to determine the persistency or reversibility of EGCG related effects after three months of discontinued use (http://clinicaltrials.gov/ct2/show/NCT01394796?term=EGCG&rank=3). The first results look promising (M. Dierssen, Journées internationales Jérôme-Lejeune, 24 Mar. 2011, Institut Pasteur, Paris).

Harmine is a β-carboline alkaloid that has long been known as a potent inhibitor of monoamine oxidase A. Harmine displays excellent specificity for DYRK1A as a potent ATP competitive inhibitor among 69 protein kinases (GB2447791A and Brain et al., Biochem., 2007, 408, 297). However, harmine also inhibits DYRK1B (5-fold less efficiently) and DYRK2 and DYRK3 (50-fold less efficiently) and its inhibitory effect on monoamine oxidase clearly limits its use as a DYRK1A inhibitor (Göckler N, et al., FEBS J. 2009, 276(21), 6324-37).

A number of inhibitors of DYRK1A/1B have been developed. Table 1 below provides the structures of such inhibitors and relevant references disclosing the same.

TABLE 1

Inhibitors of DYRK1A/1B (when non specified $IC_{50s}$ or $K_{ds}$ are given for DYRK1A)

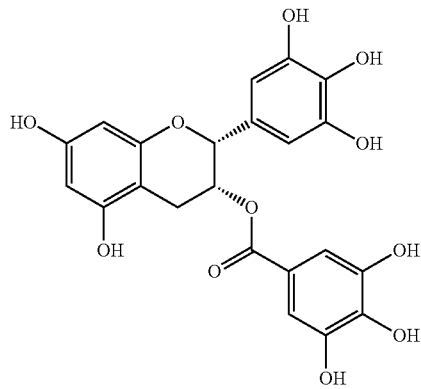

EGCG
$K_d$ = 330 nM
Non ATP competitive inhibitor
Bain et al., *Biochem. J.*, 2003, 371, 199

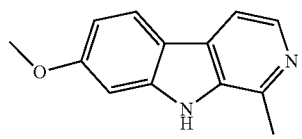

Harmine
$IC_{50}$ = 33-80 nM
GB2447791A (P. Cohen)
Bain et al., *Biochem. J.*, 2007, 408, 297

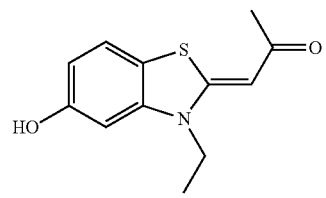

INDY
$IC_{50}$ = 240 nM
WO 2010010797 (KinoPharma Inc.)
Ogawa et al., *Nat. Commun.*, 2010, 1, 1

TABLE 1-continued

Inhibitors of DYRK1A/1B (when non specified $IC_{50s}$ or $K_{ds}$ are given for DYRK1A)

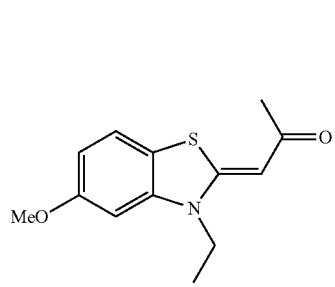

TG003
$IC_{50}$ = 930 nM
(DYRK1B $IC_{50}$ = 1.74 μM)

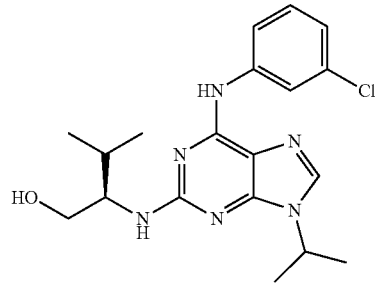

Purvalanol A
$IC_{50}$ = 300 nM
Bain et al., *Biochem. J.*, 2003, 371, 199

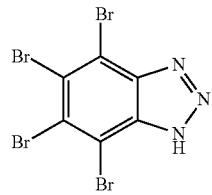

TBB
$IC_{50}$ = 4.36 μM

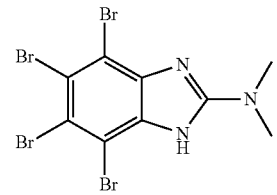

DMAT
$IC_{50}$ = 410 nM

Pagano et al., *Biochem. J.*, 2008 415, 353

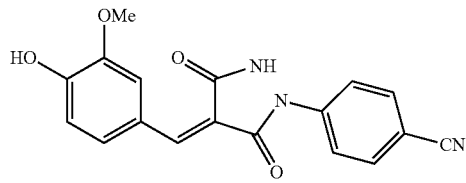

pyrazolidine-3,5-dione 21
$IC_{50}$ = 600 nM
(autophosphorylation assay)

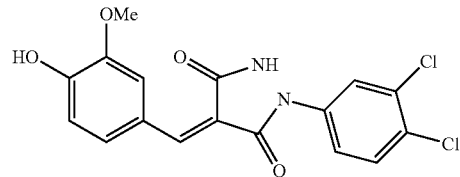

pyrazolidine-3,5-dione 18
$IC_{50}$ = 600 nM
(autophosphorylation assay)

Kim et al., *BMCL*, 2006, 16, 3772
Koo et al., *BMCL*, 2009, 19, 2324

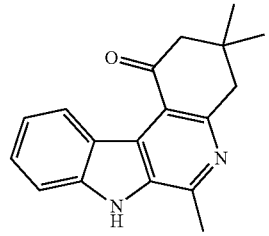

1
$K_d$ = 1 μM

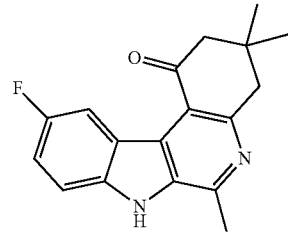

4
$K_d$ = 1 μM

US 20110021776 (MediProPharma Inc.)

TABLE 1-continued

Inhibitors of DYRK1A/1B (when non specified IC$_{50s}$ or K$_{ds}$ are given for DYRK1A)

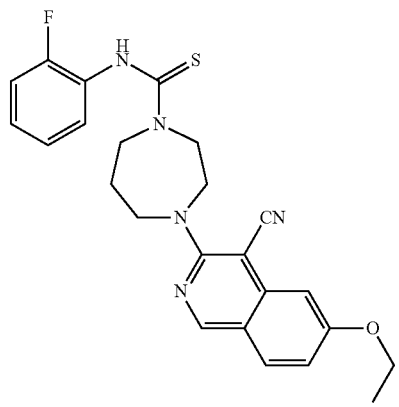

NNI-351
WO 2011037962 (Neuronascent Inc.)

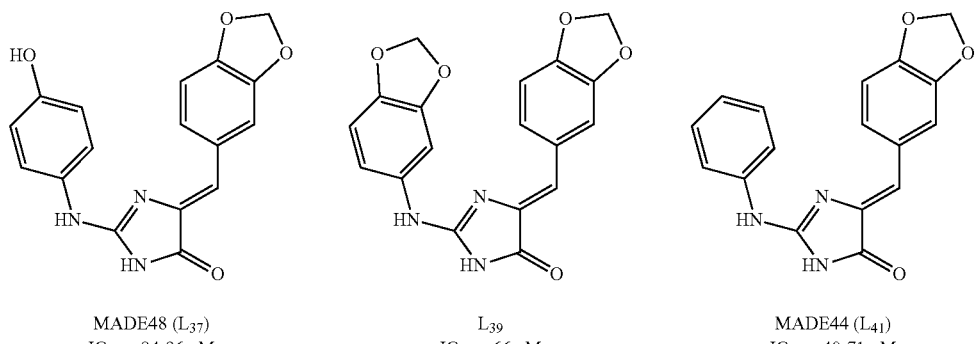

MADE48 (L$_{37}$)
IC$_{50}$ = 84-96 nM

L$_{39}$
IC$_{50}$ = 66 nM

MADE44 (L$_{41}$)
IC$_{50}$ = 40-71 nM

Debdab et al., *J. Med. Chem.*, 2011, 54, 4172
Leudettines WO 2009050352 (CNRS)

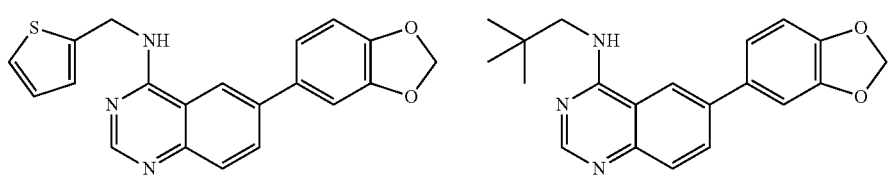

NCGC-00010037
IC$_{50}$ = 62 nM
(DYRK1B IC$_{50}$ = 697 nM)

NCGC-00189310
IC$_{50}$ = 17 nM
(DYRK1B IC$_{50}$ = 83 nM)

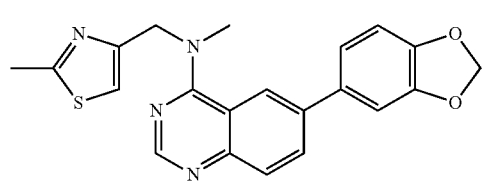

NCGC-00185981
IC$_{50}$ = 14 nM
(DYRK1B IC$_{50}$ = 25 nM)

WO 2011041655 (US department of Health & Human Services)
Mott et al., *BMCL*, 2009, 19, 6700
Rosenthal et al., *BMCL*, 2011, 21, 3152

TABLE 1-continued
Inhibitors of DYRK1A/1B (when non specified IC$_{50s}$ or K$_{ds}$ are given for DYRK1A)
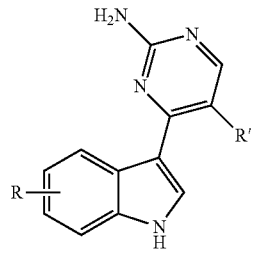
Meridianin Derivatives
30: R = 7-Br, R' = H    IC$_{50}$ = 68 nM
33: R = 6-Br, R' = I    IC$_{50}$ = 34 nM
34: R = 7-Br, R' = I    IC$_{50}$ = 39 nM
68: R = 7-NO$_2$, R' = H    IC$_{50}$ = 85 nM
72: R = 6-NO$_2$, R' = I    IC$_{50}$ = 95 nM
74: R = H, R' = I    IC$_{50}$ = 66 nM
Giraud et al., *J. Med. Chem.*, 2011, 54, 4474
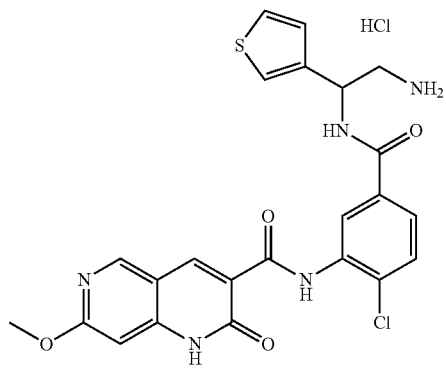
71
IC$_{50}$ = 4.6 nM (DYRK1B IC$_{50}$ < 4.6 nM)
WO 2012099066 (Hoffman-La Roche AG)
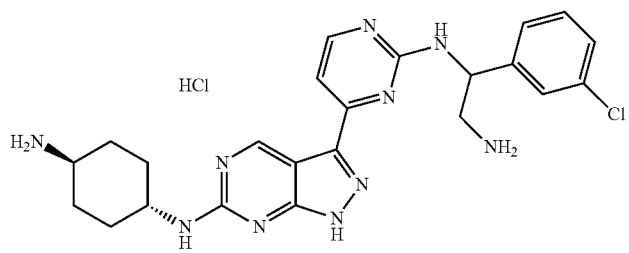
78
IC$_{50}$ = 4.6 nM (DYRK1B IC$_{50}$ < 4.6 nM)
WO 2012098068 (Hoffman-La Roche AG)

TABLE 1-continued

Inhibitors of DYRK1A/1B (when non specified $IC_{50s}$ or $K_{ds}$ are given for DYRK1A)

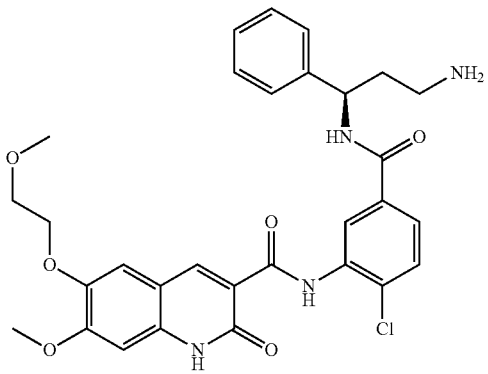

63
$IC_{50}$ = 5 nM (DYRK1B $IC_{50}$ = 8 nM)
WO 2012098070 (Hoffman-La Roche AG)

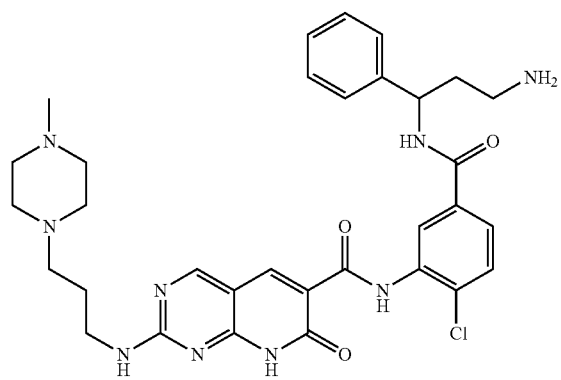

120
$IC_{50}$ = 6 nM (DYRK1B $IC_{50}$ < 4.6 nM)
WO 2012098065 (Hoffman-La Roche AG)

However, there remains a need for new potent and selective inhibitors of DYRK1A and/or DYRK1B. DYRK1A inhibitors will be useful to treat subjects with a central nervous system disease or disorder that is mediated by DYRK1A. DYRK1B inhibitors will be useful to treat subjects with cancers since DYRK1B is overexpressed and mediates survival and differentiation in many cancerous tissues.

SUMMARY OF THE INVENTION

The present invention relates to compounds of formula (I):

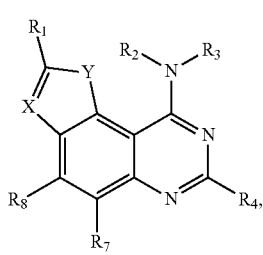

wherein
X is a nitrogen atom;
Y is an oxygen atom, a sulfur atom, a NH group or a N—(C1-C3)alkyl group;
R1 is a —C(=A)-B group, wherein
  A is NH or O and
  B is a OR5 or a NR5R6 group, wherein
  R5 and R6 are independently chosen from a hydrogen atom and an unsubstituted or substituted C1-C8 alkyl group;
A and B can alternatively independently be nitrogen and/or oxygen atoms and form, with the carbon atom to which they are bound, a heterocycloalkyl group such as dihydroimidazole or dihydrooxazole;
R2 is a hydrogen atom or an unsubstituted C1-C8 alkyl group;
R3 is an unsubstituted or substituted C1-C8 alkyl or an unsubstituted or substituted aryl or heteroaryl group;
R4 is a hydrogen atom, a halogen atom, an amino group, a cyano group or an unsubstituted or substituted C1-C5 alkyl group;
R7 and R8 are independently chosen from a hydrogen atom, a halogen atom, a hydroxyl group, or an unsubstituted or substituted C1-C5 alkyl group.

The invention further relates to a composition comprising, in a pharmaceutically acceptable carrier, a compound of formula (I).

The invention also relates to a compound of formula (I) or a pharmaceutical composition comprising a compound of formula (I), for use as a medicament.

The invention also relates to a compound of formula (I), for use in inhibiting DYRK1A in a subject in need thereof. In particular, a compound of formula (I) is used for the treatment of Down's syndrome or Alzheimer's disease. More particularly, the invention relates to a method for treating, ameliorating or controlling Down's syndrome or Alzheimer's disease in a subject in need thereof, more particularly a human subject, comprising administering a therapeutically effective amount of a compound according to the invention or a pharmaceutically acceptable salt thereof.

The invention also relates to a compound of formula (I), for use in inhibiting DYRK1B in a subject in need thereof. In particular, a compound of formula (I) is used for treating, ameliorating or controlling cancers, including specifically solid tumors, for example lung, pancreatic, colon, ovarian, breast, bone (such as osteosarcoma), prostate cancers and rhabdomyosarcoma in a mammal, specifically a human, comprising administering to said mammal a therapeutically effective amount of a compound according to the invention or a pharmaceutically acceptable salt thereof.

The invention further relates to a process of synthesis of a compound of formula (I).

Further applications and uses of the compounds of the invention, and methods of preparation thereof, are provided in the following detailed description.

DETAILED DESCRIPTION OF THE INVENTION

Definitions

In the present invention, an "alkyl" group is a saturated, straight or branched, hydrocarbon group, comprising from 1 to 8 carbon atoms (C1-C8 alkyl group), in particular from 1 to 6, or from 1 to 4 carbons atoms, unless otherwise indicated. Examples of alkyl groups having from 1 to 6 carbon atoms inclusive are methyl, ethyl, propyl (e.g., n-propyl, iso-propyl), butyl (e.g., tert-butyl, sec-butyl, n-butyl), pentyl (e.g., neo-pentyl), hexyl (e.g., n-hexyl), 2-methylbutyl, 2-methylpentyl and the other isomeric forms thereof. Alkyl groups may be unsubstituted or substituted by at least one group chosen from halogen atoms, cycloalkyl, heterocycloalkyl, aryl, heteroaryl, hydroxyl, alkoxyl, alkenyl, alkynyl, CN, nitro and amino groups.

In the present invention, an "alkenyl" group is a straight or branched hydrocarbon group comprising at least one double C=C bond, comprising from 2 to 8 carbon atoms (unless otherwise indicated). Examples of alkenyl containing from 2 to 6 carbon atoms are vinyl, allyl, 1-propenyl, 2-propenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl, 5-hexenyl and the isomeric forms thereof. Alkenyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro and amino groups.

In the present invention, an "alkynyl" group is a straight or branched hydrocarbon group comprising at least one triple C≡C bond, comprising from 2 to 8 carbon atoms. Alkynyl groups may be substituted by at least one group chosen from halogen atoms, cycloalkyl, heterocycloalkyl, aryl, heteroaryl, hydroxyl, alkoxyl, alkenyl, alkynyl, CN, nitro and amino groups.

In the present invention, an "aryl" group is an aromatic hydrocarbon cycle, comprising from 5 to 14 carbon atoms. Most preferred aryl groups are mono- or bi-cyclic and comprises from 6 to 14 carbon atoms, such as phenyl, α-naphtyl, β-naphtyl, antracenyl, preferably phenyl. "Aryl" groups also include bicycles or tricycles comprising an aryl cycle fused to at least another aryl, heteroaryl, cycloalkyl or heterocycloalkyl group, such as benzodioxolane, benzodioxane, dihydrobenzofurane or benzimidazole. Aryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, aryl groups may be substituted by adjacent substituents which can, taken together with the carbon atom to which they are attached, form a 5- to 6-membered ring which may contain one or more heteroatom(s) selected from N, O and S.

In the present invention, a "halogen atom" is a Cl, Br, F or I atom.

In the present invention, an "alkoxyl" group is an alkyl group linked to the rest of the molecule through an oxygen atom, of the formula O-alkyl.

In the present invention, an "amino" group is a $NH_2$, NHalkyl, or N(alkyl)$_2$ group.

In the present invention, a "heteroaryl" group is an aryl group whose cycle is interrupted by at least at least one heteroatom, for example a N, O, S or P atom, such as thiophene or pyridine. Heteroaryl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, Heteroaryl groups may be substituted by adjacent substituents which can, taken together with the carbon atom to which they are attached, form a 5- to 6-membered ring which may contain one or more heteroatom(s) selected from N, O and S.

In the present invention, a "cycloalkyl" denotes a saturated alkyl group that forms one cycle having preferably from 3 to 14 carbon atoms, and more preferably 3 to 8 carbon atoms, such as cyclopropyl, cyclobutyl, cyclopentyl, cyclohexyl, cycloheptyl, and cyclooctyl. cycloalkyl groups may be unsubstituted, or substituted by at least one (e.g. 1, 2 or 3) group chosen from halogen atoms, cycloalkyl, heterocycloalkyl, aryl, heteroaryl, hydroxyl, alkoxyl, alkenyl, alkynyl, CN, nitro and amino groups. In addition, cycloalkyl groups may be substituted by adjacent substituents which can, taken together with the carbon atom to which they are attached, form a 5- to 6-membered ring which may contain one or more heteroatom(s) selected from N, O and S.

In the present invention, a "heterocycloalkyl" group is a cycloalkyl group comprising at least one heteroatom, such as pyrrolidine, tetrahydrothiophene, tetrahydrofuran, piperidine, pyran, dioxin, morpholine or piperazine. A heterocycloalkyl group may in particular comprise from four to fourteen carbon atoms, such as morpholinyl, piperidinyl, pyrrolidinyl, tetrahydropyranyl, dithiolanyl. heterocycloalkyl groups may be unsubstituted, or substituted by at least one group chosen from halogen atoms, cycloalkyl, heterocycloalkyl, aryl, heteroaryl, hydroxyl, alkoxyl, alkenyl, alkynyl, CN, nitro and amino groups. In addition, heterocycloalkyl groups may be substituted by adjacent substituents which can, taken together with the carbon atom to which they are attached, form a 5- to 6-membered ring which may contain one or more heteroatom(s) selected from N, O and S.

The terms "treatment", "treating" and the like are used herein to refer generally to obtaining a desired pharmacological and/or physiological effect. These terms include both therapeutic and prophylactic treatments. The effect may be prophylactic in terms of completely or partially preventing a disease or symptom thereof and/or may be therapeutic in terms of a partial or complete stabilization or cure for a disease and/or adverse effect attributable to the disease. "Treatment" as used herein covers any treatment of a disease in a subject, and includes: (a) preventing the disease or symptom from occurring in a subject which may be predisposed to the disease or symptom, may or may not be diagnosed as having it; (b) inhibiting the disease symptom, i.e., arresting its development; or (c) relieving the disease symptom, i.e., causing regression of the disease or symptom.

The expression "therapeutically effective amount" refers to an amount of a compound disclosed herein, that is effective for preventing, ameliorating, treating or delaying the onset of a disease or condition.

Compounds and Compositions of the Invention

The present invention relates to compounds of formula (I):

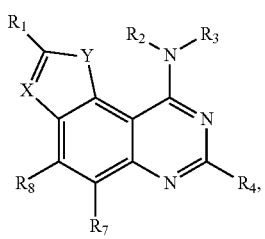

wherein
X is a nitrogen atom;
Y is an oxygen atom, a sulfur atom, a NH group or a N—(C1-C3)alkyl group;
R1 is a —C(=A)-B group, wherein
  A is NH or O and
  B is a OR5 or a NR5R6 group, wherein
  R5 and R6 are independently chosen from a hydrogen atom and an unsubstituted or substituted C1-C8 alkyl group;
A and B can alternatively independently be nitrogen and/or oxygen atoms and form, with the carbon atom to which they are bound, a heterocycloalkyl group such as dihydroimidazole or dihydrooxazole;
R2 is a hydrogen atom or an unsubstituted C1-C8 alkyl group;
R3 is an unsubstituted or substituted C1-C8 alkyl or an unsubstituted or substituted aryl or heteroaryl group;
R4 is a hydrogen atom, a halogen atom, an amino group, a cyano group or an unsubstituted or substituted C1-C5 alkyl group;
R7 and R8 are independently chosen from a hydrogen atom, ahalgen atom, a hydroxyl group, or an unsubstitution or substitution C1-C5 alky group.

The invention also includes isomers, stereoisomers, enantiomers, diastereoisomers, tautomers, pharmaceutically acceptable salts, solvates (e.g. hydrates) and prodrugs of the compounds of formula (I).

In a particular embodiment, R3 is unsubstituted or substituted aryl or heteroaryl group. In particular, the present invention discloses compounds of formula (I) with R3 being a substituted or unsubstituted phenyl group.

Particular compounds of the invention are those wherein:
Y is a sulfur atom;
A is NH;
A is NH and B is a $NR_5R_6$ group;
A is NH and B is a $OR_5$ group;
A is NH and B is a $OCH_3$ group;
A is O and B is $NH_2$;
R6 is a hydrogen atom;
R2 is a hydrogen atom;
R3 is an unsubstituted alkyl group, an alkyl group substituted by an alkoxyl group, preferably a methoxyl group, an alkyl group substituted by a cycloalkyl group, preferably a cyclohexyl group, or an alkyl group substituted by an aryl or a heteroaryl group;
R3 is an unsubstituted aryl group or an aryl group substituted by at least one group selected from halogen atoms and alkoxyl groups, preferably methoxyl groups; or
R4, R6 and/or R7 are hydrogen atoms; preferably R4, R6 and R7 are hydrogen atoms.

It should be understood that any combination of at least two of the features presented in the previous paragraph is within the scope of the present invention.

In a particular embodiment, the invention relates to a compound of formula (I) wherein:
Y is a sulphur atom;
A is NH;
B is a OR5 group wherein R5 is an unsubstituted (C1-C8)alkyl group, in particular a (C1-C4)alkyl group, in particular a methyl or ethyl group;
R2, R4, R7 and R8 are hydrogen atoms; and
R3 is an ethyl group substituted by a (C1-C4)alkoxy group (in particular a methoxy group) or an aryl group, in particular a phenyl group substituted with one or two substituents selected from the group consisting of a (C1-C4)alkyl (e.g. methyl or ethyl), a halogen atom (e.g. F or Cl) and a (C1-C4)alkoxy group (e.g. a methoxy group).

The compounds of the invention are DYRK1A and/or DYRK1B inhibitors. Their activity can be assayed by methods well known in the art. For example, the skilled person can implement the kinase assay provided in example 2 below. However, the present disclosure is not limited to implementation of this specific method.

In a particular embodiment, the compound of the invention has an $IC_{50}$ on DYRK1A activity of about 10000 nM or lower. In another embodiment, the compound of the invention has an $IC_{50}$ on DYRK1A and/or DYRK1B activity of about 5000 nM or lower. In another embodiment, the compound of the invention has an $IC_{50}$ on DYRK1A and/or DYRK1B activity of about 1000 nM or lower. In another embodiment, the compound of the invention has an $IC_{50}$ on DYRK1A and/or DYRK1B activity of about 500 nM or lower. In another embodiment, the compound of the invention has an $IC_{50}$ on DYRK1A and/or DYRK1B activity of about 100 nM or lower. In another embodiment, the compound of the invention has an $IC_{50}$ on DYRK1A and/or DYRK1B activity of about 10 nM or lower. In another embodiment, the compound of the invention has an $IC_{50}$ on DYRK1A and/or DYRK1B activity of about 1 nM or lower. In another embodiment, the compound of the invention has an $IC_{50}$ on DYRK1A and/or DYRK1B activity of about 0.5 nM or lower.

Specific examples of compounds of formula (I) which fall within the scope of the present invention include:

9-(3-Chloro-4-fluorophenylamino)-N-(2-morpholinoethyl)thiazolo[5,4-f]quinazoline-2-carboximidamide 1,
9-(3-Chloro-4-fluorophenylamino)-N-(2-(piperidin-1-yl)ethyl)thiazolo[5,4-f]quinazoline-2-carboximidamide 2,
9-(3-Chloro-4-fluorophenylamino)-N-(2-(pyrrolidin-1-yl)ethyl)thiazolo[5,4-f]quinazoline-2-carboximidamide 3,
9-(3-Chloro-4-fluorophenylamino)-N-(2-(dimethylamino)ethyl)thiazolo[5,4-f]quinazoline-2-carboximidamide 4,
9-(3-Chloro-4-fluorophenylamino)-N-(2-(diethylamino)ethyl)thiazolo[5,4-f]quinazoline-2-carboximidamide 5,
N-Benzyl-9-(3-chloro-4-fluorophenylamino)thiazolo[5,4-f]quinazoline-2-carboximidamide 6,
9-(3-Chloro-4-fluorophenylamino)-N,N-dimethylthiazolo[5,4-f]quinazoline-2-carboximidamide 7,
9-(4-Bromo-2-fluorophenylamino)-N-(2-morpholinoethyl)thiazolo[5,4-f]quinazoline-2-carboximidamide 8,
9-(4-Bromo-2-fluorophenylamino)-N-(2-(piperidin-1-yl)ethyl)thiazolo[5,4-f]quinazoline-2-carboximidamide 9,
9-(4-Bromo-2-fluorophenylamino)-N-(2-(dimethylamino)ethyl)thiazolo[5,4-f]quinazoline-2-carboximidamide 10,
9-(4-Bromo-2-fluorophenylamino)-N-(2-(diethylamino)ethyl)thiazolo[5,4-f]quinazoline-2-carboximidamide 11,
9-(4-Bromo-2-fluorophenylamino)-N-(2-(pyrrolidin-1-yl)ethyl)thiazolo[5,4-f]quinazoline-2-carboximidamide 12,
N-Benzyl-9-(4-bromo-2-fluorophenylamino)thiazolo[5,4-f]quinazoline-2-carboximidamide 13,
9-(4-Bromo-2-fluorophenylamino)-N-(2-(dimethylamino)ethyl)thiazolo[5,4-f]quinazoline-2-carboximidamide 14,
9-(4-Bromo-2-fluorophenylamino)-N-isopropylthiazolo[5,4-f]quinazoline-2-carboximidamide 15,
9-(4-Bromo-2-fluorophenylamino)-N-(4-fluorobenzyl)thiazolo[5,4-f]quinazoline-2-carboximidamide 16,
9-(4-Bromo-2-fluorophenylamino)-N-(3-fluorobenzyl)thiazolo[5,4-f]quinazoline-2-carboximidamide 17,
9-(4-Bromo-2-fluorophenylamino)-N-(cyclohexylmethyl)thiazolo[5,4-f]quinazoline-2-carboximidamide 18,
9-(4-Bromo-2-fluorophenylamino)-N-(pyridin-4-ylmethyl)thiazolo[5,4-f]quinazoline-2-carboximidamide 19,
9-(3-Cyanophenylamino)-N-(2-morpholinoethyl)thiazolo[5,4-f]quinazoline-2-carboximidamide 20,
9-(3-Cyanophenylamino)-N-(2-(piperidin-1-yl)ethyl)thiazolo[5,4-f]quinazoline-2-carboximidamide 21,
N-(2-(Dimethylamino)ethyl)-9-(4-methoxyphenylamino)thiazolo[5,4-f]quinazoline-2-carboximidamide 22,
N-(2-(Diethylamino)ethyl)-9-(4-methoxyphenylamino)thiazolo[5,4-f]quinazoline-2-carboximidamide 23,
9-(4-Methoxyphenylamino)-N-(2-(pyrrolidin-1-yl)ethyl)thiazolo[5,4-f]quinazoline-2-carboximidamide 24,
N-benzyl-9-(4-methoxyphenylamino)thiazolo[5,4-f]quinazoline-2-carboximidamide 25,
9-(4-Methoxyphenylamino)-N-(2-morpholinoethyl)thiazolo[5,4-f]quinazoline-2-carboximidamide 26,
9-(4-Methoxyphenylamino)-N-(2-(piperidin-1-yl)ethyl)thiazolo[5,4-f]quinazoline-2-carboximidamide 27,
9-(4-Methoxyphenylamino)-N,N-dimethylthiazolo[5,4-f]quinazoline-2-carboximidamide 28,
9-(Benzo[d][1,3]dioxol-5-ylamino)-N-(2-morpholinoethyl)thiazolo[5,4-f]quinazoline-2-carboximidamide 29,
9-(Benzo[d][1,3]dioxol-5-ylamino)-N-(2-(piperidin-1-yl)ethyl)thiazolo[5,4-f]quinazoline-2-carboximidamide 30,
9-(Benzo[d][1,3]dioxol-5-ylamino)-N-(2-(pyrrolidin-1-yl)ethyl)thiazolo[5,4-f]quinazoline-2-carboximidamide 31,
9-(Benzo[d][1,3]dioxol-5-ylamino)-N-benzylthiazolo[5,4-f]quinazoline-2-carboximidamide 32,
9-(Benzo[d][1,3]dioxol-5-ylamino)-N-(2-(dimethylamino)ethyl)thiazolo[5,4-f]quinazoline-2-carboximidamide 33,
9-(Benzo[d][1,3]dioxol-5-ylamino)-N-(2-(diethylamino)ethyl)thiazolo[5,4]quinazoline-2-carboximidamide 34,
9-(3-Chloro-4-fluorophenylamino)thiazolo[5,4-f]quinazoline-2-carboxamide 35,
9-(4-Bromo-2-fluorophenylamino)thiazolo[5,4-f]quinazoline-2-carboxamide 36,
9-(4-Methoxyphenylamino)thiazolo[5,4-f]quinazoline-2-carboxamide 37,
9-(3,4,5-Trimethoxyphenylamino)thiazolo[5,4]quinazoline-2-carboxamide 38,
9-(Benzo[d][1,3]dioxol-5-ylamino)thiazolo[5,4-f]quinazoline-2-carboxamide 39,
9-(3,4-Dimethoxyphenylamino)thiazolo[5,4-f]quinazoline-2-carboxamide 40,
N-(3-Chloro-4-fluorophenyl)-2-(4,5-dihydro-1H-imidazol-2-yl)thiazolo[5,4-f]quinazolin-9-amine 41,
2-(4,5-dihydrooxazol-2-yl)-N-(4-methoxyphenyl)thiazolo[5,4-f]quinazolin-9-amine 42,
Methyl 9-(3-chloro-4-fluorophenylamino)thiazolo[5,4-f]quinazoline-2-carbimidate 43,
Methyl 9-(4-bromo-2-fluorophenylamino)thiazolo[5,4-f]quinazoline-2-carbimidate 44,
Methyl 9-(4-methoxyphenylamino)thiazolo[5,4-f]quinazoline-2-carbimidate 45,
Methyl 9-((4-methoxyphenyl)(methyl)amino)thiazolo[5,4-f]quinazoline-2-carbimidate 46,
Methyl 9-(7-bromobenzo[d][1,3]dioxol-5-ylamino)thiazolo[5,4-f]quinazoline-2-carbimidate 47,
Methyl 9-(benzo[d][1,3]dioxol-5-ylamino)thiazolo[5,4-f]quinazoline-2-carbimidate 48,
Methyl 9-(2,3-dihydrobenzo[b][1,4]dioxin-6-ylamino)thiazolo[5,4-f]quinazoline-2-carbimidate 49,
Methyl 9-((2,3-dihydrobenzo[b][1,4]dioxin-6-yl)(methyl)amino)thiazolo[5,4-f]quinazoline-2-carbimidate 50,
Methyl 9-(3,4-dimethoxyphenylamino)thiazolo[5,4-f]quinazoline-2-carbimidate 51,
Methyl 9-((3,4-dimethoxyphenyl)(methyl)amino)thiazolo[5,4-f]quinazoline-2-carbimidate 52,
Methyl 9-(4-hydroxyphenylamino)thiazolo[5,4-f]quinazoline-2-carbimidate 53,
Methyl 9-(3-hydroxy-4-methoxyphenylamino)thiazolo[5,4-f]quinazoline-2-carbimidate 54,
Methyl 9-(2,3-dihydrobenzofuran-5-ylamino)thiazolo[5,4-f]quinazoline-2-carbimidate 55,
Methyl 9-(4-chlorophenylamino)thiazolo[5,4-f]quinazoline-2-carbimidate 56,
Methyl 9-(3,4-dichorophenylamino)thiazolo[5,4-f]quinazoline-2-carbimidate 57,
Methyl 9-(3-ethynylphenylamino)thiazolo[5,4-f]quinazoline-2-carbimidate 58,
Methyl 9-(1H-benzo[d]imidazol-6-ylamino)thiazolo[5,4-f]quinazoline-2-carbimidate 59,
Methyl 9-(4-hydroxy-3-nitrophenylamino)thiazolo[5,4-f]quinazoline-2-carbimidate 60,
Methyl 9-(3,4,5-trimethoxyphenylamino)thiazolo[5,4-f]quinazoline-2-carbimidate 61,
Methyl 9-(2,4-dimethoxyphenylamino)thiazolo[5,4-f]quinazoline-2-carbimidate 62,
Methyl 9-(3,5-dimethoxyphenylamino)thiazolo[5,4-f]quinazoline-2-carbimidate 63,
Methyl 9-(phenylamino)thiazolo[5,4-f]quinazoline-2-carbimidate 64,
Methyl 9-(p-tolylamino)thiazolo[5,4-f]quinazoline-2-carbimidate 65,
Methyl 9-(4-fluorophenylamino)thiazolo[5,4-f]quinazoline-2-carbimidate 66, Methyl 9-(3-cyanophenylamino)thiazolo[5,4-f]quinazoline-2-carbimidate 67,
Methyl 9-(2-bromo-4-fluorophenylamino)thiazolo[5,4-f]quinazoline-2-carbimidate 68,
Methyl 9-(2-fluoro-4-methoxyphenylamino)thiazolo[5,4-f]quinazoline-2-carbimidate 69,
Methyl 9-(4-cyanophenylamino)thiazolo[5,4-f]quinazoline-2-carbimidate 70,
Methyl 9-(4-chloro-2-fluorophenylamino)thiazolo[5,4-f]quinazoline-2-carbimidate 71,
Methyl 9-(2,4-dichorophenylamino)thiazolo[5,4-f]quinazoline-2-carbimidate 72,
Methyl 9-(4-methoxy-3-nitrophenylamino)thiazolo[5,4-f]quinazoline-2-carbimidate 73,
Methyl 9-(4-tert-butylphenylamino)thiazolo[5,4-f]quinazoline-2-carbimidate 74,
Methyl 9-(3-chlorophenylamino)thiazolo[5,4-f]quinazoline-2-carbimidate 75,
Methyl 9-(4-(dimethylamino)phenylamino)thiazolo[5,4-f]quinazoline-2-carbimidate 76,
Methyl 9-(4-(pyrrolidin-1-yl)phenylamino)thiazolo[5,4-f]quinazoline-2-carbimidate 77,
Methyl 9-(2,4-difluorophenylamino)thiazolo[5,4-f]quinazoline-2-carbimidate 78,
Methyl 9-(3-fluoro-4-hydroxyphenylamino)thiazolo[5,4-f]quinazoline-2-carbimidate 79,
Methyl 9-(4-(trifluoromethyl)phenylamino)thiazolo[5,4-f]quinazoline-2-carbimidate 80,
Ethyl 9-(4-bromo-2-fluorophenylamino)thiazolo[5,4-f]quinazoline-2-carbimidate 81,
Ethyl 9-(benzo[d][1,3]dioxol-5-ylamino)thiazolo[5,4-f]quinazoline-2-carbimidate 82,
Benzyl 9-(benzo[d][1,3]dioxol-5-ylamino)thiazolo[5,4-f]quinazoline-2-carbimidate 83,
Methyl 9-(benzo[d][1,3]dioxol-5-ylamino)thiazolo[5,4-f]quinazoline-2-carboxylate 84,
Isopropyl 9-(benzo[d][1,3]dioxol-5-ylamino)thiazolo[5,4-f]quinazoline-2-carbimidate 85,
9-((2-Bromo-4-fluorophenyl)amino)thiazolo[5,4-f]quinazoline-2-carboxamide 86,
9-((2,4-Dichlorophenyl)amino)thiazolo[5,4-f]quinazoline-2-carboxamide 87,
Butyl 9-((2,4-dichlorophenyl)amino)thiazolo[5,4-f]quinazoline-2-carbimidate 88,
Methyl 9-((2,4-dichlorophenyl)amino)thiazolo[5,4-f]quinazoline-2-carboxylate 89.

The compounds according to the present invention may be prepared by various methods known to those skilled in the art. More preferably, the following chemical routes were carried out.

The compounds of Formula I, or pharmaceutically acceptable salts thereof, may be prepared by any process known to be applicable for the preparation of chemically-related compounds by one skilled in the art. Such processes, when used to prepare compounds of Formula I, or pharmaceutically-acceptable salts thereof, are provided as further features of the invention and are illustrated by the following schemes. Starting materials are commercially available or may be obtained by standard procedures of organic chemistry. The preparation of such starting materials is described within the accompanying non-limiting examples. Alternatively starting materials are obtainable by analogous procedures to those illustrated which are within the ordinary skill of an organic chemist.

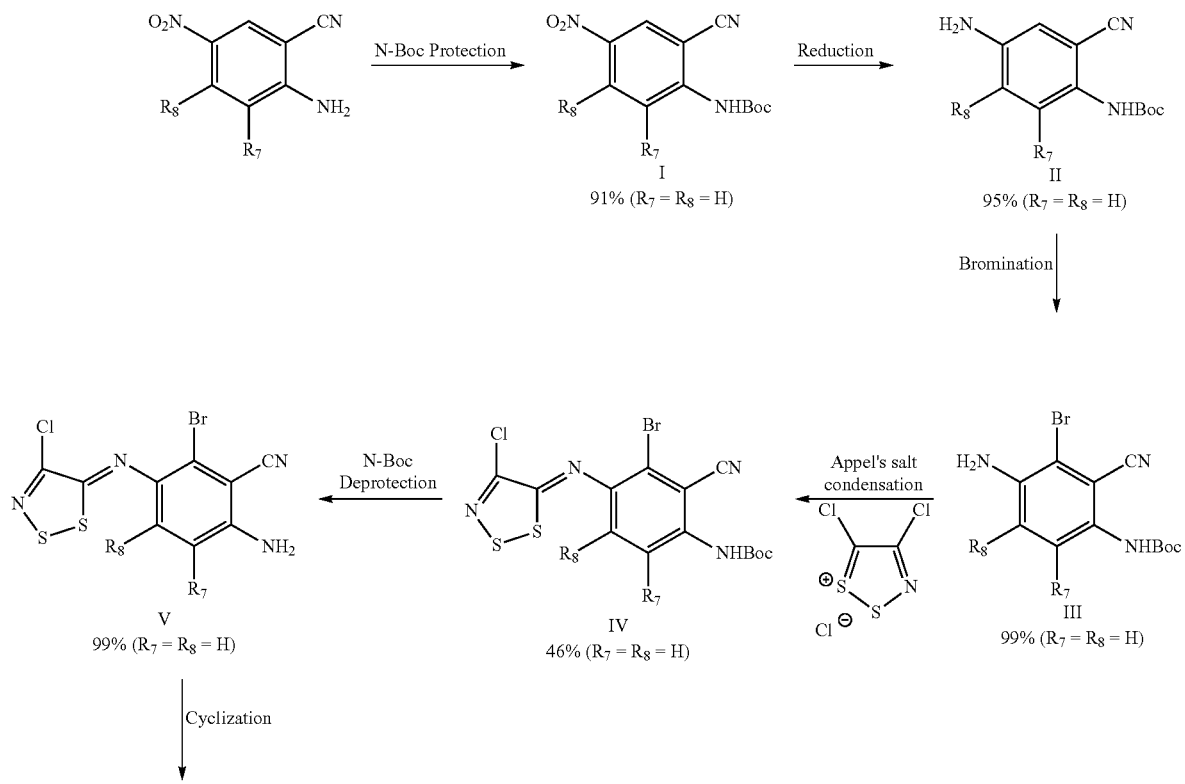

Scheme 1: Preparation of thiazolo[5,4-f]quinazoline-2-carbonitriles VIIIaa-ib

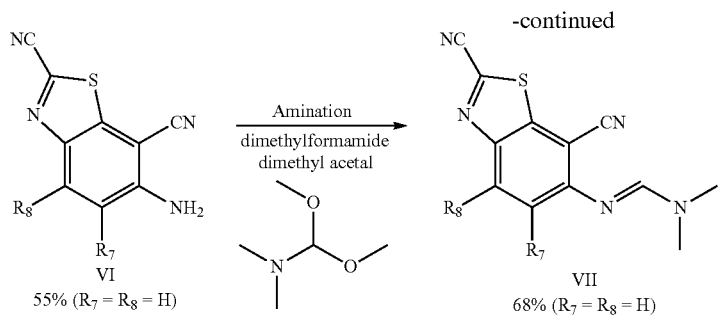 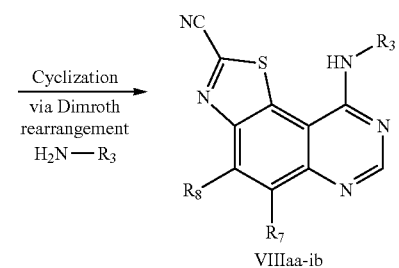

The thiazolo[5,4-f]quinazoline-2-carbonitriles VIIIaa-ib were prepared following scheme 1: N-Boc Protection of 2-amino-5-nitrobenzonitrile using di-tert-butyl dicarbonate in a suitable solvent, such as dichloromethane, in presence of suitable bases such as triethylamine and 4-(dimethylamino)pyridine and preferably at room temperature, provides tert-butyl (2-cyano-4-nitrophenyl)carbamate I in high yield. Reduction of the nitro intermediate I, for example by treatment with ammonium formate and a catalytic amount of 10% palladium charcoal preferably in ethanol under microwave irradiation for preferably 30 min at 600 W, provides tert-butyl 4-amino-2-cyanophenylcarbamate II in high yield. Treatment of intermediate II by a solution of bromine in dichloromethane in a suitable solvent, such as acetic acid, preferably at room temperature provides tert-butyl 4-amino-3-bromo-2-cyanophenylcarbamate III in a quantitative yield. Intermediate III is reacted with Appel's salt (4,5-dichloro-1,2,3-dithiazolium chloride) (Appel, R. et al., Chem. Ber., 1985, 118, 1632) preferably in dichloromethane at room temperature to afford (Z)-tert-butyl-3-bromo-4-(4-chloro-5H-1,2,3-dithiazol-5-ylideneamino)-2-cyanophenylcarbamate IV. N-Boc deprotection of intermediate IV using di-tert-butyl dicarbonate in a suitable solvent, such acetic acid, preferably under microwave irradiation at 118° C. provides (Z)-6-amino-2-bromo-3-(4-chloro-5H-1,2,3-dithiazol-5-ylideneamino)benzonitrile V in a quantitative yield. Cyclization of intermediate V may be accomplished by treatment with copper iodide in a suitable solvent, such as pyridine, preferably under microwave irradiation at 400 W at 130° C. for 20 min to obtain 6-aminobenzo[d]thiazole-2,7-dicarbonitrile VI in good yield (Besson, T. et al., J. Chem. Soc., Perkin Trans. 1, 1998, 3925). Treatment of intermediate VI in a suitable solvent, such as dimethylformamide dimethylacetal, preferably under microwave irradiation at 70° C. (600 W) gives (E)-N'-(2,7-dicyanobenzo[d]thiazol-6-yl)-N,N-dimethylformimidamide VII in good yield. Cyclization of intermediate VII in thiazolo[5,4-f]quinazoline-2-carbonitriles VIIIaa-ib may be accomplished by a Dimroth rearrangement using the appropriate aniline or primary amine $R_3NH_2$ (preferably 1.5 equivalent) in a suitable solvent, such acetic acid and preferably under microwave irradiation at 118° C. (600 W) (Foucourt, A. et al., Tetrahedron, 2010, 66, 4495).

Accordingly, the invention relates to a process of synthesis of a thiazoloquinazoline compound of formula I, comprising the steps of:

a) condensing Appel's salt (4,5-dichloro-1,2,3-dithiazol-1-ium chloride

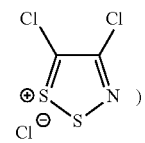)

on a compound of the formula (III)

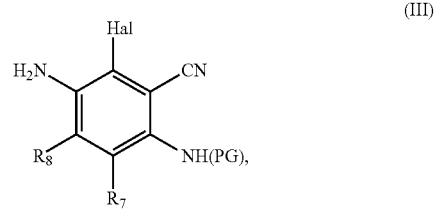

wherein (PG) is an amino protecting group, for instance a Boc group, and Hal is a halogen atom, for instance a Br atom, to form a compound of the formula (IV)

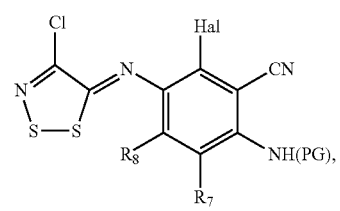

b) deprotecting the amino group of the compound of the formula (IV), and cyclising the obtained compound of formula (V)

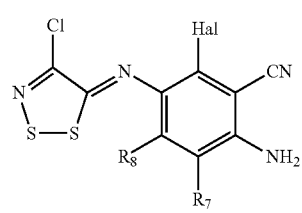

to form a compound of the formula (VI)

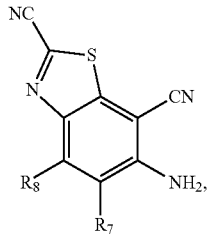
(VI)

c) aminating the compound of the formula (VI) obtained in step b) with dimethylformamide dimethylacetal to form a compound of the formula (VII)

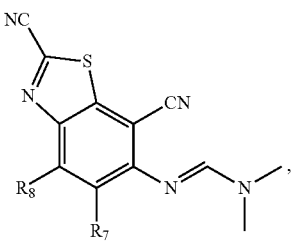
(VII)

and d) cyclising the compound of the formula (VII) obtained in step c) to form a tricyclic compound of the formula (VIII)

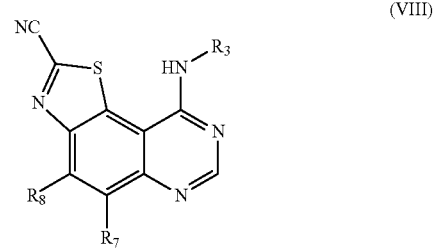
(VIII)

via a Dimroth rearrangement.

In a particular embodiment of the process of synthesis of the invention, R7 and R8 are independently selected from a hydrogen atom or an unsubstituted or substituted C1-C5 alkyl group. In particular, both R7 and R8 are hydrogen atoms.

In a further embodiment, compound of formula (VIII) can be further N-alkylated to obtain a compound of formula (IX) wherein R2 is an unsubstituted C1-C8 alkyl group.

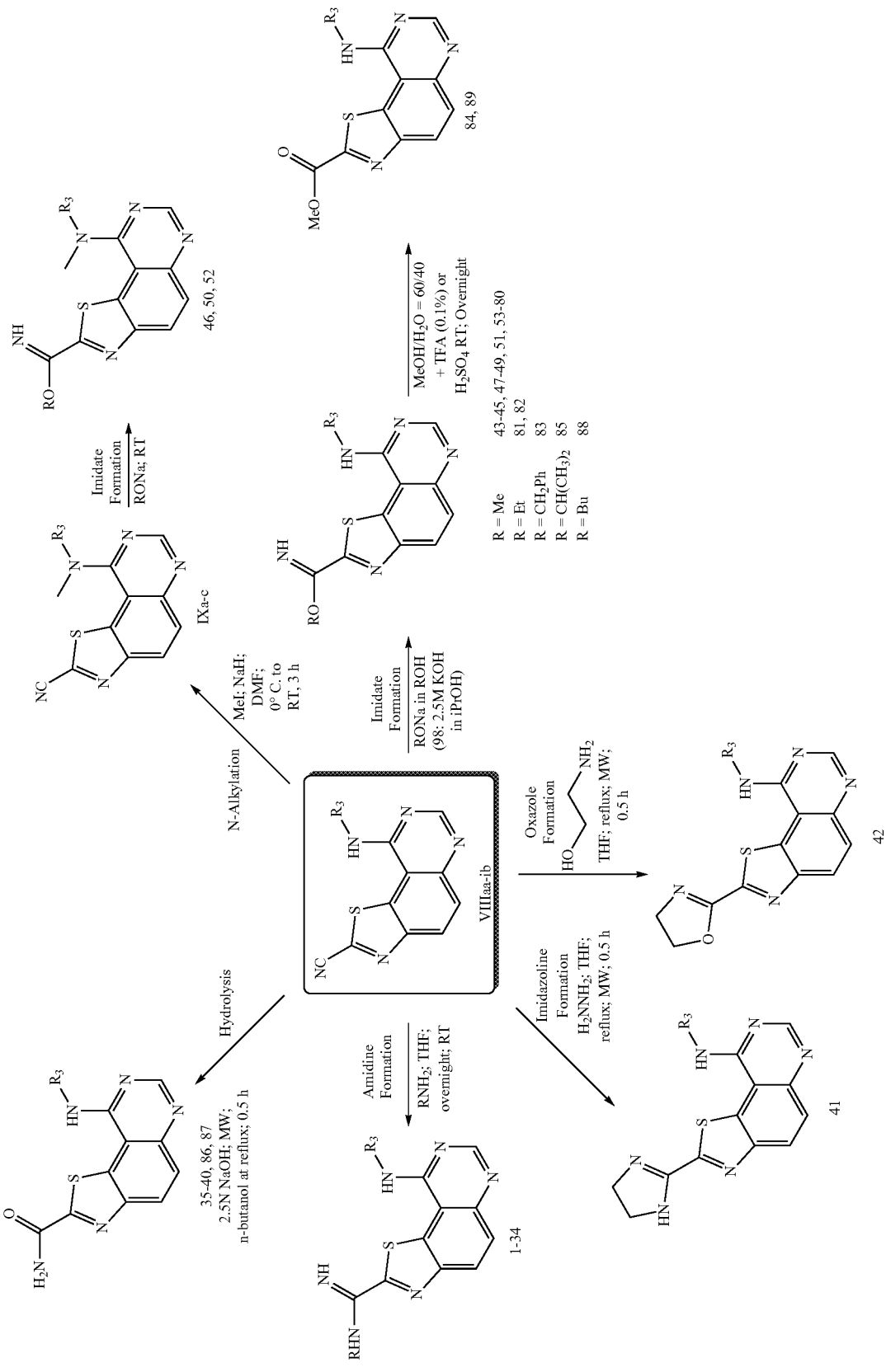
Scheme 2: Preparation of Compounds 1 to 89

The compounds 1 to 89 were prepared following scheme 2 starting from the thiazolo[5,4-f]quinazoline-2-carbonitriles VIIIaa-ib:

The N-methylated-thiazolo[5,4-f]quinazoline-2-carbonitriles IXa-c were obtained by N-alkylation of the thiazolo [5,4-f]quinazoline-2-carbonitriles VIIIja, VIIIda, VIIIha with methyl iodide in a suitable solvent, such as dimethylformamide, in presence of a base, such as sodium hydride and preferably for 1 h at 0° C. then for 2 h at room temperature. The amidines 1-34 were prepared from the thiazolo[5,4-f]quinazoline-2-carbonitriles VIIIaa-fa by treatment with the appropriate secondary amine $RHN_2$ (preferably 1.2 equivalent) in a suitable solvent, such as dry THF and preferably for overnight at room temperature (Bénéteau, V., Besson, T. et al., Eur. J. Med. Chem., 1999, 34, 1053). Hydrolysis under basic conditions of thiazolo[5,4-f]quinazoline-2-carbonitriles VIIIaa, VIIIba, VIIIda, VIIIea, VIIIfa, and VIIIia, using preferably a 2.5 N solution of aqueous NaOH in a suitable solvent, such as n-butanol and at reflux preferably for 0.5 h under microwave irradiation, provided respectively amides 35-40 in high yields, and 86 and 87 in modest yields. The imidazoline 41 or oxazole 42 were obtained respectively from thiazolo[5.4-f]quinazoline-2-carbonitriles VIIIaa or VIIIda by treatment by ethylene diamine or ethanolamine, in a suitable solvent, such as dry THF at reflux and preferably under microwave irradiation for 30 min (Testard, A., Besson, T. et al., J. Enz. Inhib. Med. Chem., 2005, 20, 557). The methyl imidates 43-80 were obtained from their corresponding thiazolo[5,4-f]quinazoline-2-earbonitriles VIIIaa-ib or N-methylated-thiazolo [5,4-f]quinazoline-2-carbonitriles IXa-c by treatment with a 0.5 M solution of sodium methoxide in a suitable solvent, such as methanol, and preferably under microwave irradiation at 65° C. for 30 min. The ethyl imidates 81-82, the benzyl imidate 83 were prepared similarly to the methyl imidates 43-80 using, respectively, a 0.5 M solution of sodium ethoxide in ethanol or a 1.0 M solution of sodium benzyloxide in benzyl alcohol and preferably under microwave irradiation, at 80° C. for 30 min (81-82) or 100° C. for 30 min (83). The isopropyl imidate 85 was prepared from carbonitrile VIIIfa with a 2.5 N KOH solution in isopropanol and preferably under microwave irradiation, at 100° C. for 2 h. The butyl imidate 88 was prepared from carbonitrile VIIIab with NaOH (2.5 M solution in water) in butanol and preferably under microwave irradiation at 117° C. for 30 min. Finally the methyl esters 84 and 89 were prepared in high yield from the methyl imidates 48 and 72 respectively, by treatment, preferably for overnight with a mixture of MeOH/$H_2O$=60/40 in presence of trifluoroacetic acid (0.1%) (for 84) or with diluted $H_2SO_4$ for 2 h (for 89), and preferably at room temperature.

It should be understood that other ways of producing these compounds may be designed by the skilled person, based on common general knowledge and following guidance contained in this application.

Another object of the present invention is the intermediate compounds used for the preparation of compounds of formula (I). The present invention thus also relates to a compound which is an intermediate in scheme 1 above. In particular, the present invention relates to a compound of formula III, IV, V, VI or VII as represented in scheme 1 above. The present invention relates in particular to the specific intermediate compounds herein below mentioned in the examples.

The compounds according to the invention can be in the form of salts, particularly acid or base salts, preferably compatible with pharmaceutical use (i.e. pharmaceutically acceptable salts of the compounds of the invention). It will be appreciated by those skilled in the art that non-pharmaceutically acceptable salts of compounds of formula (I) are also part of the present invention, since such non-pharmaceutically acceptable salts can be useful as intermediates in the preparation of pharmaceutically acceptable salts.

Salts of compounds of the invention include pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like.

Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Further examples of pharmaceutically acceptable inorganic or organic acid addition salts include the pharmaceutically acceptable salts listed in J. Pharm. Sci. 1977, 66, 2, which is incorporated herein by reference. Examples of metal salts include lithium, sodium, potassium, magnesium salts and the like. Base salts include, but are not limited to, those formed with pharmaceutically acceptable cations, such as sodium, potassium, lithium, calcium, magnesium, ammonium and alkylammonium. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Other examples of organic bases include lysine, arginine, guanidine, diethanolamine, choline and the like. The present invention includes in particular cationic salts, for example sodium or potassium salts, or alkyl esters (e.g. methyl or ethyl) of the phosphate group.

The pharmaceutically acceptable salts can in particular be prepared by reacting the compound of formula (I) with acids such as hydrochloric acid, hydrobromic acid, nitric acid, sulfuric acid, phosphoric acid, p-toluenesulphonic acid, methanesulfonic acid, fonic acid, acetic acid, citric acid, maleic acid, salicylic acid, hydroxynaphthoic acid, ascorbic acid, palmitic acid, succinic acid, benzoic acid, benzenesulfonic acid, tartaric acid and the like in solvents like ethyl acetate, ether, alcohols, acetone, THF, dioxane, etc. Mixture of solvents may also be used.

The compounds of the invention can be administered alone, but are generally administered with a pharmaceutically acceptable carrier, with respect to standard pharmaceutical practice (such as described in Remington's Pharmaceutical Sciences, Mack Publishing). Accordingly, a further object of this invention relates to a pharmaceutical composition comprising a compound of formula (I), as defined above, and a pharmaceutically acceptable carrier. In a particular embodiment, the weight ratio of the compound of formula (I) to the carrier is comprised from 1:99 to 99:1.

The carrier must be pharmaceutically "acceptable" in the sense of being compatible with the other ingredients of the invention, in particular with the compound of formula (I) present in the composition, and not injurious to the subject to be treated.

According to a particular embodiment, the invention relates to a pharmaceutical composition as described above, further comprising another pharmaceutically active drug.

The compounds are administered in a therapeutically effective amount. Dosages and dosage regimen in which the compounds of formula (I) are administered will vary according to the dosage form, mode of administration, the condition being treated and particulars of the patient being treated. Accordingly, optimal therapeutic concentrations will be best determined at the time and place through routine experimentation.

The compounds of formula (I) may be administered by different routes including oral, rectal, nasal, topical, vaginal or parenteral (e.g., subcutaneous, intramuscular, intravenous, intra-arterial, intradermal, intraperitoneal) administration. For oral administration, the compounds of formula (I) can be formulated into conventional oral dosage forms such as solid preparations (for examples capsules, tablets), and liquid preparations (for example as syrups, elixirs and concentrated drops).

They can be presented in unit dosage form and can be prepared by any method well known to those skilled in the art of pharmacy.

The amounts of various compounds encompassed by formula (I) to be administered can be determined by standard procedures taking into account factors such as the compound $IC_{50}$, $EC_{50}$, the biological half-life of the compound, the age, size and weight of the patient, and the disease or disorder associated with the patient. The importance of these and other factors to be considered are known to those of ordinary skill in the art. Amounts administered also depend on the routes of administration and the degree of oral bioavailability (should the compound be administered via the oral route). For example, for compounds with low oral bioavailability, relatively higher doses may have to be administered.

The compounds according to the invention can be used enterally or parenterally. Orally, the compounds according to the invention are suitably administered in the amount from about 0.1 mg per day to 1,000 mg per day. For parenteral, sublingual, intranasal, or intrathecal administration, the compounds according to the invention are suitably used in the amount from about 0.5 to about 100 mg/day; for depo administration and implants from about 0.5 mg/day to about 50 mg/day; for topical administration from about 0.5 mg/day to about 200 mg/day; for rectal administration from about 0.5 mg to about 500 mg. In a preferred aspect, the therapeutically effective amounts for oral administration is from about 1 mg/day to about 100 mg/day; and for parenteral administration from about 5 to about 50 mg daily. In a more preferred aspect, the therapeutically effective amounts for oral administration are from about 5 mg/day to about 50 mg/day.

Compound of the present invention can be administered orally using any pharmaceutically acceptable dosage form known in the art for such administration. The vehicle may be any solution, suspension, powder, gel, etc., including isotonic solution, buffered and saline solutions, such as syrups or aqueous suspensions, etc. The compounds may be administered by any suitable route, including systemic delivery, intra-venous, intra-arterial, intra-cerebral or intrathecal injections. Repeated injections may be performed, if desired. The dosage can vary within wide limits and will have to be adjusted to the individual requirements in each particular case, depending upon several factors known to those of ordinary skill in the art. Agents determining the dosage of dosage the active compounds can be the pharmacodynamic characteristics of the particular agent and its mode and route of administration; the age, health and weight of the recipient; the nature and extent of the symptoms; the kind of concurrent treatment; the frequency of treatment; and the effect desired. A daily dosage of active ingredient can be expected to be about 0.001 to about 1000 milligrams per kilogram of body weight, with the preferred dose being about 0.1 to about 30 mg/kg. The daily oral dosage can vary from about 0.01 mg to 1000 mg, 0.1 mg to 100 mg, or 10 mg to 500 mg per day of a compound. The daily dose may be administered as single dose or in divided doses and, in addition, the upper limit can also be exceeded when this is found to be indicated.

The compounds of the present invention can be administered in such oral dosage forms as tablets, capsules (each of which can include sustained release or timed release formulations), pills, powders, granules, elixirs, tinctures, suspensions, syrups, and emulsions. Likewise, they may also be administered in intravenous (bolus or infusion), intraperitoneal, subcutaneous, or intramuscular form, all using dosage forms well known to those of ordinary skill in the pharmaceutical arts. An effective but non-toxic amount of the compound desired can be employed to treat a disease state for which tubulin polymerisation plays a crucial role. Compounds can be administered by any means that produces contact of the active agent with the agent's site of action in the body of a host, such as a human or a mammal. They can be administered by any conventional means available for use in conjunction with pharmaceuticals, either as individual therapeutic agents or in a combination of therapeutic agents, either administered alone, or administered with a pharmaceutical carrier selected on the basis of the chosen route of administration and standard pharmaceutical practice.

The compound for the present invention can be administered in intranasal form via topical use of suitable intranasal vehicles, or via transdermal routes, using those forms of transdermal skin patches wall known to those of ordinary skill in that art.

Oral administration in the form of a tablet or capsule containing the active compound can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water, and the like. Moreover, when desired or necessary, suitable binders, lubricants, disintegrating agents, and coloring agents can also be incorporated into the mixture. Sweetening agents such as those set forth above, and flavoring agents may be added to provide a palatable oral preparation. These compositions may be preserved by the addition of an anti-oxidant such as butylated hydroxyanisol or alpha-tocopherol. Suitable binders include starch, gelatin, natural sugars such as glucose or beta-lactose, corn sweeteners, natural and synthetic gums such as acacia, tragacanth, or sodium alginate, carboxymethylcellulose, polyethylene glycol, waxes, and the like. Lubricants used in these dosage forms include sodium oleate, sodium stearate, magnesium stearate, sodium benzoate, sodium acetate, sodium chloride, and the like. Disintegrators include, without limitation, starch, methylcellulose, agar, bentonite, xanthan gum, and the like.

Compounds of the invention can also be administered in the form of liposomal particulate delivery systems, such as small unilamellar vesicles, large unilamellar vesicles, and multilamellar vesicles. Liposomes can be formed from a variety of phospholipids, such as cholesterol, stearylamine, or phosphatidylcholines. Alternatively, compounds of the present invention may also be coupled with soluble polymers as targetable drug carriers, such as polymers made of polyvinylpyrrolidone, pyran copolymer, polyhydroxypropylmethacrylamide- phenol, polyhydroxyethylaspartamide-phenol, or polyethyleneoxide-polylysine substituted with palmitoyl residues. Polymers may also belong to the class of biodegradable polymers useful in achieving controlled release of a drug, for example, polylactic acid, polyglycolic acid, copolymers of polylactic and polyglycolic acid, poly-epsilon caprolactone, polycyanoacylates, etc. or block copolymers of hydrogels.

Compounds of the present invention may be formulated into gelatin capsules with the addition of lactose, starch, cellulose derivatives, magnesium stearate, stearic acid, and the like as powdered carriers. Similar diluents can be used to make compressed tablets. Both tablets and capsules can be manufactured as sustained release products to provide for continuous release of medication over a period of hours. Compressed tablets can be sugar coated or film coated to mask any unpleasant taste and protect the tablet from the atmosphere, or enteric coated for selective disintegration in the gastrointestinal tract. Liquid dosage forms for oral administration can contain coloring and flavoring to increase patient acceptance. In general, water, a suitable oil, saline, aqueous dextrose (glucose), and related sugar solutions and glycols such as propylene glycol or polyethylene glycols are suitable carriers for parenteral solutions. Solutions for parenteral administration preferably contain a water soluble salt of the active ingredient, suitable stabilizing agents, and if necessary, buffer substances. Antioxidizing agents such as sodium bisulfite, sodium sulfite, or ascorbic acid, either alone or combined, are suitable stabilizing agents. Also used are citric acid and its salts and sodium EDTA. In addition, parenteral solutions can contain preservatives, such as benzalkonium chloride, methyl- or propyl-paraben, and chlorobutanol.

Methods of Use of the Compounds of the Invention

The present invention also relates to a compound of formula (I) as a medicament.

Compounds of formula (I) are DYRK1A and/or DYRK1B inhibitors. Accordingly, they can be used in a method for the inhibition of DYRK1A and/or DYRK1B. The method can be an in vivo or in vitro method. In vitro, the invention relates to a method for inhibiting DYRK1A and/or DYRK1B, either in isolated form or contained in a cell, comprising contacting DYRK1A and DYRK1B or a cell containing DYRK1A and/or DYRK1B with a compound Of formula (I). In vivo, the method is for inhibiting DYRK1A and/or DYRK1B in a sunject in need thereof, comprising administering to said subject a therapeutically effective amount of a compound of formula (I).

The invention further relates to a compound of formula (I), or a pharmaceutical composition comprising a compound of formula (I), for the inhibition of DYRK1A and/or DYRK1B. The invention further relates to a compound of formula (I) or a pharmaceutical composition comprising the same, for the treatment of a disease related to DYRK1A and/or DYRK1B expression or activity.

DYRK1A kinase has been shown to be involved in a number of diseases. In addition to the information provided above, a summary of different diseases and conditions involving DYRK1A is provided below. The present invention thus also relates to a method for the treatment of these specific diseases and conditions, comprising administering to a subject in need thereof an effective amount of a compound of formula (I). Of course, the summary provided below is not limiting the invention and compounds of formula (I) are expected to be useful for the treatment of any diseases mediated by or involving DYRK1A.

DYRK1A has been shown to phosphorylate the tau protein at multiple threonine and serine sites including Thr181, Ser202, Thr202, Thr217, Thr231, Ser396, Ser400, Ser404 and Ser422, both in vitro and in cultured cells. Evidence has been presented that hyperphosphorylation of Tau by DYRK1A is a causative factor in the early onset of Alzheimer disease (AD) in Down's syndrome (DS) patients. Increased DYRK1A immunoreactivity has been reported in the cytoplasm and nuclei of scattered neurons of the entorhinal cortex, hippocampus and neocortex in neurodegenerative diseases associated with tau phosphorylation, including AD, DS and Pick disease (Ferrer et al., Neurobiol. Dis., 2005, 20(2), 392-400). The elevated activity of DYRK1A contributes to the cognitive deficits in DS and the development of AD. Therefore, it is known that DYRK1A kinase can contribute to DS, AD and Pick disease. DYRK1A can also contribute to other forms of neurodegeneration, including α-synuclein aggregation and fibrillization in Lewy bodies, granulovacuolar degeneration (GVD) in the hippocampal pyramidal neurons, and neuronal and astrocyte degeneration with DYRK1A-positive corpora amylacea deposition in aging, AD, DS/AD and other diseases (Kim et al., J. Biol. Chem., 2006, 281(44), 33250-7). Therefore, compounds of formula (I) will be useful for the treatment of central nervous system diseases such as neurodegenerative and neurological diseases and disorders. The term "neurodegenerative diseases" includes but is not limited to DS, AD, Parkinson's disease, Huntington's disease, Pick's disease, Gerstmann-Straussler-Scheinker disease with tangles, amyotrophic-lateral sclerosis, AIDS-related dementia, fragile X-associated tremor/ataxia syndrome (FXTAS), progressive supranuclear palsy (PSP), and striatonigral degeneration (SND), which is included with olivopontocerebellar degeneration (OPCD) and Shy Drager syndrome (SDS) in a syndrome known as multiple syndrome atrophy (MSA), brain injury, amyotrophic lateral sclerosis and inflammatory pain, regenerative (recovery) treatment of CNS disorders such as spinal cord injury, acute neuronal injury (stroke, traumatic brain injury), guam-parkinsonism-dementia complex, corticobasal neurodegeneration, frontotemporal dementia, mood disorders. In a particular embodiment, the compound of formula (I) is used for treating early onset of AD in DS patients. Furthermore, the compounds of the invention can also be used to treat other forms of neurodegeneration, including α-synuclein aggregation and fibrillization in Lewy bodies, granulovacuolar degeneration (GVD) in the hippocampal pyramidal neurons, and neuronal and astrocyte degeneration. They can also be used to treat corpora amylacea deposition in aging, AD, DS/AD and other diseases.

The invention also relates to the use of a compound of formula (I) for decreasing Aβ production. In particular, the compounds of formula (I) are used to prevent APP cleavage. In particular a compound of formula (I) is use to inhibit the formation of Aβ peptide and consequently, to reduce beta amyloid plaque formation on the brain. A DYRK1A inhibitor of formula (I) thus can be useful for the treatment of AD and other amyloid-related disorders.

The expression of DYRK1A in mature brain and retinal neurons (Marti et al., Brain Res., 2003, 964(2), 250-63, Wegiel et al., Brain Res., 2004, 1010(1-2), 69-80, and Laguna et al., Dev. Cell., 2008, 15(6), 841-53) and the implication in synaptic activity of DYRK1A-regulated transcription factors, NFAT (Arron et al., Nature, 2006, 441 (7093), 595-600) and CREB (Yang et al., J. Biol. Chem., 2001, 276(43), 39819-24), indicate that altered DYRK1A expression in disease might alter adult neuronal activity in brain and retina. Compounds of formula (I) that inhibit DYRK1A will therefore be useful for improving learning and memory and for counteracting neurological disorders and diseases of the brain and retina. Neurological disorders and diseases of the retina includes but are not limited to retinitis pigmentosa (RP), glaucoma, retinopathies, age-related macular degeneration (ARMD), myopic macular degeneration and neurological complications associated with diabetes in a diabetic individual (i.e. diabetic neuropathy).

Alternative splicing is observed with >95% of the genes and constitutes the main source for protein diversity, generating different protein from the same pre-mRNA by the differential use of splice site. It is estimated that 70 to 95% of the alternative splicing events ultimately result in changes in the protein sequence and that on average, a given gene is subjected to 7 splicing events. This extensive contribution of splicing to the transcriptome's functional diversity also results in a clear implication of splicing dysregulations in the development of the pathophysiology of diseases, such as many human cancers (Venables JP., Cancer Res., 2004, 64(21), 7647-54), muscular dystrophies (Nishida A., Nat. Commun., 2011, 2, 308), premature aging disorders (Koshimizu E., PLoS One., 2011, 6(3), e17688) and Alzheimer's disease. Splicing diversity in AD brain has been recently associated with both the onset (Miller, J. A., S. Horvath, et al., 2010, Proc. Natl. Acad. Sci. USA, 107(28), 12698-12703) and risk of developing AD (Avramopoulos, D., M. Szymanski, et al., 2010, Neurobiol. Aging, Jun 4. [Epub ahead of print]). Therefore, by manipulation of the splicing machinery, it is anticipated that gene translation can be controlled to rectify abnormal splicing. Several kinases including DYRK1A alter the function of the splicesome, controlling the phosphorylation status and activity of splicing factors that control splicesome assembly and are implicated in constitutive and alternative splicing control and splicing site choice. Accordingly, the compounds of the present invention can be used for treating splicing dysregulations observed in diseases such as cancers, muscular dystrophies, premature aging disorders and AD. In particular, the compounds of the invention can be used for rescuing brain defects and for the treatment of diseases implicating deregulations of the splicing and phosphorylation of the tau protein which have been identified in certain neurodegenerative diseases and disorders called tauopathies. Tauopathies are disorders and diseases, and in particular neurological disorders and diseases, characterized by the presence of neuronal tau aggregation, in particular the presence of neurofibrillary tangles. The invention thus also relates to the treatment of tauopathies by administering a compound of formula (I) to a subject in need thereof.

Elevated DYRK1A may also be playing a pathological role in dividing cells, such as in cancer. In pancreatic endocrine neoplasms, microarray hybridization data showed up-regulation of DYRK1A in metastatic pancreatic endocrine neoplasms when compared with nonmetastatic pancreatic endocrine neoplasms, indicative of a role of the kinase in the disease (Hansel et al., Clin. Cancer Res., 2004, 10, 6152-8, 2004). Moreover, DYRK1A is a potent megakaryoblastic tumor-promoting gene that contributed to leukemogenesis through dysregulation of nuclear factor of activated T cells (NFAT) activation. Calcineurin/NFAT pathway inhibition has been implicated in the decreased tumor incidence in adults with DS, the same pathway can be both proleukemic in children and antitumorigenic in adults (Malinge S., et al., J. Clin. Invest., 2012, 122(3), 948-962). Accordingly, the invention also relates to a compound of formula (I) for use in the treatment of abnormal cell division, such as cancer and leukemias. In particular, the compound is used in the treatment of metastatic pancreatic endocrine neoplasms or megakaryoblastic leukemia.

Further applications include limiting viral infection, cancerous and neurological complications associated with viral infection. Immortalization is a critical event in virus-related oncogenesis. HPV16, a high-risk tumorigenic virus, has been identified as one of the causative agents for the development of cervical cancer. Subsequent to viral infection, the constitutive expression of the viral oncoproteins E6 and E7 plays a number of critical roles in maintaining the transformed phenotype. DYRK1A increases the transforming potential of HPV16-infected cells by stabilizing HPV16E7 oncoprotein through phosphorylation of the threonine 5 and threonine 7 residues (Liang et al., Int. J. Biochem. Cell. Biol., 2008, 40, 2431-41). Additionally, increased expression of DYRK1A in HPV16 immortalized keratinocytes and cervical lesions may serve as a candidate antiapoptotic factor in the Forkhead (FKHR) regulated pathway and initiate immortalization and tumorigenesis. Inversely, knockdown of DYRK1A in the HPV immortalized cells led to increased apoptosis (Chang et al., Int. J. Cancer., 2007, 120(11), 2377-85), indicating that potent and selective inhibitors of DYRK1A may be beneficial for HPV-related cancers. The compounds of formula (I) can thus also be used to limit viral infection and cancerous and neurological complications associated with viral infection. In particular, the compounds of formula (I) can be used to increase apoptosis in HPV-related cancers, in particular in HPV immortalized keratinocytes. Polymorphism (SNP) in DYRK1A was also found to be associated with HIV-1 replication in monocyte-derived macrophages, as well as with progression to AIDS in HIV-1-infected individuals (Bol et al., PLoS One., 2011, 6(2), e17190). Therefore, viral infection may include AIDS. In a particular embodiment, the compound of the present invention is used to reduce viral replication of HIV.

Transgenic mice overexpressing DYRK1A exhibit significantly reduced bone mass despite the decreased osteoclastogenesis, which is reminiscent of osteoporotic bone phenotype in Down syndrome patients (Lee et al., J. Biol. Chem., 2009, 284(48), 33343-51). Thus, further applications include pharmacological modulation of DYRK1A which might be used as a strategy to treat unregulated bone resorption. Therefore, the invention also relates to a compound of formula (I) for use in the treatment of bone resorption.

In addition, thanks to their activity on DYRK1B, the compounds of the present invention may be used for the treatment of cancer, in particular solid tumor cancers. The invention therefore also relates to a compound of formula (I), for use in inhibiting DYRK1B in a subject in need thereof. In particular, a compound of formula (I) is used for treating, ameliorating or controlling cancers, including specifically solid tumors, for example lung, pancreatic, colon, ovarian, breast, bone (such as osteosarcoma), prostate cancers and rhabdomyosarcoma in a mammal, specifically a human, comprising administering to said mammal a therapeutically effective amount of a compound according to the invention or a pharmaceutically acceptable salt thereof.

Further aspects and advantages of this invention will be disclosed in the following examples, which should be regarded as illustrative and not limiting the scope of this application.

EXAMPLES

Example 1

Production of Compounds of the Invention

General

All reactions were monitored by thin-layer chromatography with silica gel 60 $F_{254}$ pre-coated aluminium plates (0.25 mm).

Melting points of solid compounds were measured on a WME Köfler hot-stage with a precision of ±2° C. and are uncorrected.

IR spectra were recorded on a Perkin Elmer IRFT 1650 spectrometer. Liquids were applied as a film between KBr windows and solids were dispersed in a KBr pellet. Absorption bands are given in $cm^{-1}$.

$^1H$, $^{13}C$ and $^{19}F$ NMR spectra were recorded on a Brucker DXP 300 spectrometer at 300, 75 and 282 MHz respectively. Abbreviations used for peak multiplicities are s: singlet, d: doublet, t: triplet, q: quadruplet and m: multiplet. Coupling constants J are in Hz and chemical shifts are given in ppm and calibrated with DMSO-$d_6$ or $D_2O$ (residual solvent signals).

Mass spectra analysis was performed by the Mass Spectrometry Laboratory of the University of Rouen. Mass spectra (EI) were recorded with a Waters LCP $1^{er}$ XR spectrometer.

Microwave experiments were conducted in a commercial microwave reactor especially designed for synthetic chemistry.

RotoSYNTH (Milestone S.r.l. Italy) is a multimode cavity with a microwave power delivery system ranging from 0 to 1200W. Open vessel experiments were carried out in a 50-1000 mL round bottom flask fitted with a reflux condenser. The temperature was monitored via a fibre-optic contact thermometer protected in a Teflon coated ceramic well inserted directly in the reaction mixture. The vessel contents were stirred by means of an adjustable rotating magnetic plate located below the floor of the microwave cavity and a Teflon-coated magnetic stir bar inside the vessel. Temperature, pressure and power profiles were monitored in both cases through the EASYControl software provided by the manufacturer.

Preparation of Intermediates I to VII

Synthesis of tert-butyl 2-cyano-4-nitrophenylcarbamate I

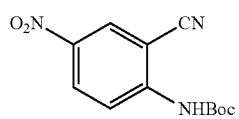

To a solution of 2-amino-5-nitrobenzonitrile (10.0 g, 61.3 mmol) in dichloromethane (100 mL) were added triethylamine (8.50 mL, 61.3 mmol), di-tert-butyl dicarbonate (26.8 g, 123 mmol), and 4-(dimethylamino) pyridine (7.50 g, 61.3 mmol). The solution was stirred for 4 h at room temperature under an argon atmosphere. The solvent was removed in vacuo and the crude residue was purified by flash chromatography (DCM-petroleum ether, 8:2) to afford the expected compound I (14.6 g, 91% yield) as a white solid; mp 134° C.; IR (KBr) $v_{max}/cm^{-1}$ 3412, 3072, 3012, 2982, 2935, 2229, 1735, 1617, 1582, 1543, 1508, 1473, 1455, 1420, 1372, 1350, 1320, 1303, 1257, 1234, 1176, 1143, 1052, 1028, 923, 915, 889, 853; $^1H$ NMR (300 MHz, DMSO-$d_6$) δ 10.04 (s, 1H, NH), 8.63 (d, 1H, J=2.7 Hz), 8.44-8.40 (dd, 1H, $J_1$=2.7 Hz, $J_2$=9.3 Hz), 7.85 (d, 1H, J=9.3 Hz), 1.49 (s, 9H); $^{13}C$ NMR (75 MHz, DMSO-$d_6$) δ 153.1, 146.6, 142.6, 129.3, 128.8, 123.4, 115.2, 105.3, 81.2, 27.3; HRMS calcd for $C_{12}H_{12}N_3O_4$ (M+H$^+$): 262.0828, found 262.0831.

Reduction of Compound I: synthesis of tert-butyl 4-amino-2-cyanophenylcarbamate II

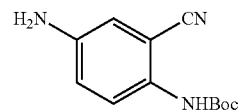

A stirred mixture of I (10.0 g, 37.9 mmol), 189.5 mmol of ammonium formate and a catalytic amount of 10% palladium charcoal in 300 mL of ethanol was irradiated under microwaves for 30 min. The irradiation was programmed to obtain a constant temperature (85° C.) with a power input of 600W. The catalyst was removed by filtration through Celite and washed with ethanol. The resulting filtrate was evaporated under reduced pressure. Then the residue was dissolved in EtOAc, washed with water, dried over $MgSO_4$ and concentrated under reduced pressure to give the reduced compound 2 (8.4 g, 95% yield) as a pale yellow solid; mp 126° C.; IR (KBr) $v_{max}/cm^{-1}$ 3476, 3431, 3365, 3398, 2988, 2934, 2222, 1697, 1628, 1587, 1521, 1443, 1429, 1392, 1367, 1324, 1294, 1274, 1250, 1230, 1161, 1053, 1028, 947, 902, 872, 849, 824; $^1H$ NMR (300 MHz, DMSO-$d_6$)δ8.82 (s, 1H, NH). 7.02(d, 1H, J=8.1 Hz), 6.81 (s, 1H), 6.78 (d, 1H,J=2.7 Hz), 5.44 (s, 2H, $NH_2$), 1.43 (s, 9H); $^{13}C$ NMR (75 MHz, DMSO-$d_6$) δ153.8, 146.7, 128.8, 127.9, 118.7, 117.5, 115.9, 109.8, 79.0, 28.0; HRMS calcd for $C_{12}H_{16}N_3O_2$ (M+H$^+$): 234.1243, found 234.1240.

Bromination of Compound II: synthesis of tert-butyl 4-amino-3-bromo-2-cyanophenylcarbamate III

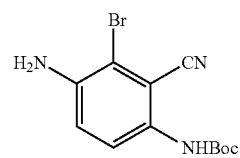

A solution of bromine (25.1 mmol) in dichloromethane (1.3 mL) was added dropwise, under an argon atmosphere, to a solution of amine II (27.9 mmol) in acetic acid (325 mL). After 2.5 h of stirring at room temperature, the solvent was removed in vacuo. The excess of acetic acid was co-evaporated with heptane to afford the expected compound III (10.1 g, quantitative yield) as a beige solid; mp 163° C.; IR (KBr) $v_{max}$/cm$^{-1}$ 3327, 2826, 2605, 2566, 2236, 1955, 1716, 1610, 1561, 1496, 1481, 1398, 1369, 1280, 1238, 1193, 1153, 1059, 963, 906, 838; $^1$H NMR (300 MHz, DMSO-d$_6$) δ 9.05 (s, 1H, NH), 7.11 (d, 1H, J=8.7 Hz), 7.05 (d, 1H, J=8.7 Hz), 6.01 (s, 2H, NH$_2$), 1.43 (s, 9H); $^{13}$C NMR (75 MHz, DMSO-d$_6$) δ 153.6, 144.1, 131.6, 126.9, 119.6, 116.1, 112.8, 107.8, 79.5, 28.1; HRMS calcd for C$_{12}$H$_{15}$N$_3$O$_2$Br (M+H$^+$): 312.0348, found 312.0354.

Condensation of Appel Salt: synthesis of (Z)-tert-butyl-3-bromo-4-(4-chloro-5H-1,2,3-dithiazol-5-ylideneamino)-2-cyanophenylcarbamate IV

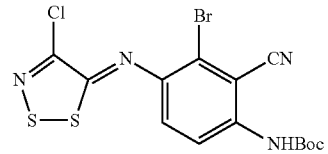 [SMILES: CC(C)(C)OC(=O)Nc1ccc(/N=c2\ssnc2Cl)c(Br)c1C#N]

A suspension of the ortho-brominated amine III (5.0 g, 16.0 mmol), 4,5-dichloro-1,2,3-dithiazolium chloride (7.34 g, 35.2 mmol) in dichloromethane (100 mL) was stirred at room temperature under an argon atmosphere. After 3 h of stirring at room temperature, pyridine (5.7 mL, 70.5 mmol) was added and the mixture was stirred again for 1 h at room temperature and the resulting solution was concentrated under reduced pressure. The obtained crude residue was purified by flash chromatography (DCM-petroleum ether, 5:5) to afford the expected compound IV (3.3 g, 46% yield) as an orange solid; mp 140-160° C.; IR (KBr) $v_{max}$/cm$^{-1}$ 3366, 2977, 2935, 2227, 1714, 1597, 1570, 1560, 1508, 1392, 1369, 1270, 1238, 1156, 1057, 971, 859, 846, 809; $^1$H NMR (300 MHz, DMSO-d$_6$) δ 9.64 (s, 1H, NH), 7.60 (d, 1H, J=8.7 Hz), 7.55 (d, 1H, J=8.7 Hz), 1.48 (s, 9H); $^{13}$C NMR (75 MHz, DMSO-d$_6$) δ 163.5, 152.9, 147.4, 146.0, 140.0, 126.1, 123.6, 117.7, 115.3, 112.2, 80.4, 27.9; HRMS calcd for C$_{14}$H$_{13}$N$_4$O$_2$S$_2$BrCl (M+H$^+$): 446.9352, found 446.9340.

Deprotection of Amino Group: synthesis of (Z)-6-amino-2-bromo-3-(4-chloro-5H-1,2,3-dithiazol-5-ylideneamino)benzonitrile V

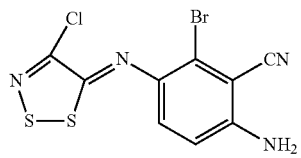 [SMILES: N#Cc1c(N)ccc(/N=c2\ssnc2Cl)c1Br]

A mixture of (Z)-tert-butyl-3-bromo-4-(4-chloro-5H-1,2,3-dithiazol-5-ylideneamino)-2-cyanophenylcarbamate IV (3.3 g, 7.4 mmol) and acetic acid (100 mL) was irradiated under microwaves at 118° C. for 2 h. After cooling, the resulting solution was concentrated under reduced pressure to give the desired compound V (2.8 g, quantitative yield) as an orange solid; mp 188-198° C.; IR (KBr) $v_{max}$/cm$^{-1}$ 3421, 3340, 3231, 2220, 1701, 1647, 1596, 1575, 1473, 1405, 1291, 1251, 1192, 1137, 973, 869, 847, 804; $^1$H NMR (300 MHz, DMSO-d$_6$) δ 7.36 (d, 1H, J=9.0 Hz), 6.91 (d, 1H, J=9.0 Hz), 6.55 (s, 2H, NH$_2$); $^{13}$C NMR (75 MHz, DMSO-d$_6$) δ 159.6, 151.7, 146.7, 137.8, 124.4, 119.0, 116.4, 115.7, 97.2; HRMS calcd for C$_9$H$_5$N$_4$S$_2$BrCl (M+H$^+$): 346.8828, found 346.8846.

Cyclisation in 6-aminobenzo[d]thiazole-2,7-dicarbonitrile VI

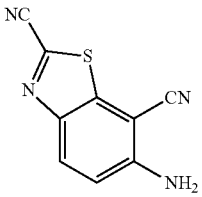 [SMILES: N#Cc1nc2ccc(N)c(C#N)c2s1]

A suspension of imine V (2.5 g, 7.2 mmol), copper iodide (2.7 g, 14.4 mmol) in pyridine (50 mL) was irradiated under microwaves at 130° C. (power input: 400 W) for 20 min. After cooling, the mixture was dissolved in EtOAc, washed with sodium thiosulfate solution. The organic layer was dried over MgSO$_4$, and the solvent was removed in vacuo. The crude residue was purified by flash chromatography (DCM-EtOAc, 9:1) to afford the expected compound VI (0.79 g, 55% yield) as a brown solid; mp 248° C.; IR (KBr) $v_{max}$/cm$^{-1}$ 3433, 3350, 3250, 2225, 1653, 1593, 1487, 1451, 1415, 1330, 1290, 1206, 1161, 1128, 821; $^1$H NMR (300 MHz, DMSO-d$_6$) δ8.11 (d, 1H, J =9.3 Hz), 7.31 (s, 2H, NH$_2$), 7.10 (d, 1H, J=9.3 Hz); $^{13}$C NMR (75 MHz, DMSO-d$_6$) δ154.6, 143.7, 141.6, 131.5, 130.9, 119.4, 116.9, 114.3, 83.6; HRMS calcd for C$_9$H$_3$N$_4$S (M+H$^+$): 199.0078, found 199.0076.

Synthesis of (E)-N'-(2,7-dicyanobenzo[d]thiazol-6-yl)-N,N-dimethylformimidamide VII

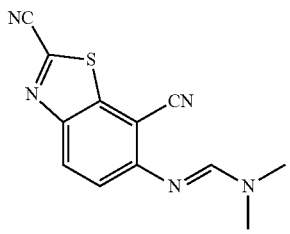 [SMILES: CN(C)/C=N/c1ccc2nc(C#N)sc2c1C#N]

A suspension of VI (0.47 g, 2.34 mmol) in dimethylformamide dimethyl acetal (6 mL) was irradiated under microwaves at 70° C. (power input: 600 W) during 2 min. After cooling, the brown precipitate formed was filtered, washed with Et$_2$O and dried to afford the expected compound 7 (0.41 g, 68% yield) as a brown solid; mp 185° C.; IR (KBr) $v_{max}$/cm$^{-1}$ 2932, 2901, 2224, 1622, 1566, 1500, 1450, 1410, 1387, 1368, 1272, 1229, 1173, 1099, 1058, 995, 964, 928, 874, 819; $^1$H NMR (300 MHz, DMSO-d$_6$) δ 8.33 (d, 2H, J=9.3 Hz), 7.62 (d, 1H, J=9.3 Hz), 3.15 (s, 3H), 3.07 (s, 3H); $^{13}$C NMR (75 MHz, DMSO-d$_6$) 157.3, 156.5, 145.9, 140.2, 133.0, 129.3, 120.3, 116.6, 113.3, 96.4, 34.3; HRMS calcd for C$_{12}$H$_{10}$N$_5$S (M+H$^+$): 256.0657, found 256.0644.

General Procedure for the Synthesis of thiazolo[5,4-f]quinazoline-2-carbonitriles VIIIaa-ib A mixture of (E)-N-(2,7-dicyanobenzo[d]thiazol-6-yl)-N,N-dimethylformimidamide VII (0.05 g, 0.19 mmol) and the appropriate amine (0.29 mmol, 1.5 equiv) in acetic acid (2 mL) was irradiated under microwaves at 118° C. (power input: 600 W). On completion (followed by TLC), the reaction was cooled to ambient temperature. The solvent was removed in vacuo and the crude residue was purified by flash chromatography to afford the expected compounds VIIIaa-ib.

9-(3-Chloro-4-fluorophenylamino)thiazolo[5,4-f]quinazoline-2-carbonitrile VIIIaa

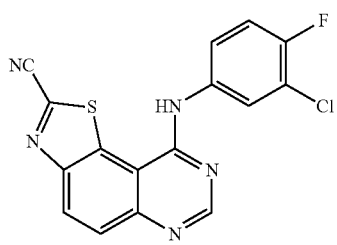 [SMILES: N#Cc1nc2ccc3ncnc(Nc4ccc(F)c(Cl)c4)c3c2s1]

Prepared from VII and 3-chloro-4-fluoroaniline. Flash chromatography eluent (DCM-EtOAc, 8:2). Yield: 64%; yellow solid; mp 252° C.; IR (KBr) $v_{max}$/cm$^{-1}$ 3456, 3015, 2970, 2946, 2229, 1642, 1441, 1153, 1129, 1051, 968, 903, 817, 774, 695; $^{19}$F NMR (282 MHz, DMSO-d$_6$) δ −123.8; $^1$H NMR (300 MHz, DMSO-d$_6$) δ 8.43 (d, 1H, J=9.0 Hz), 8.30 (s, 1H), 7.62 (m, 2H), 7.34 (m, 2H); HRMS calcd for C$_{16}$H$_7$N$_5$SClF (M+H$^+$): 356.0156, found 356.0167.

9-(4-Bromo-2-fluorophenylamino)thiazolo[5,4-f]quinazoline-2-carbonitrile VIIIba

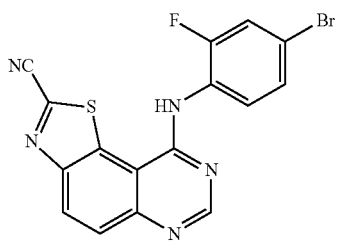 [SMILES: N#Cc1nc2ccc3ncnc(Nc4ccc(Br)cc4F)c3c2s1]

Prepared from VII and 4-bromo-2-fluoroaniline. Flash chromatography eluent (DCM-EtOAc, 8:2). Yield: 30%; brown solid; mp>260° C.; IR (KBr) $v_{max}$/cm$^{-1}$ 3325, 3053, 2230, 1649, 1614, 1582, 1556, 1499, 1462, 1380, 1351, 1250, 1154, 1132, 1052, 969, 904, 875, 817; $^{19}$F NMR (282 MHz, DMSO-d$_6$) δ −119.9; $^1$H NMR (300 MHz, DMSO-d$_6$) δ 8.55 (d, 1H, J=9.0 Hz), 8.26 (d, 1H, J=9.0 Hz), 7.78 (m, 1H), 7.55-7.52 (m, 1H), 7.38-7.25 (m, 2H); HRMS calcd for C$_{16}$H$_8$N$_5$SBrF (M+H$^+$): 399.9668, found 399.9662.

9-(3-Cyanophenylamino)thiazolo[5,4-f]quinazoline-2-carbonitrile VIIIca

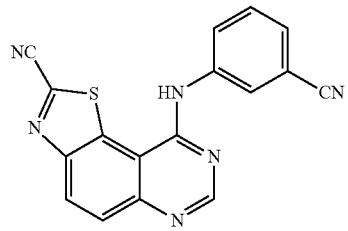 [SMILES: N#Cc1cccc(Nc2ncnc3ccc4nc(C#N)sc4c23)c1]

Prepared from VII and 3-aminobenzonitrile. Flash chromatography eluent (DCM-EtOAc, 5:5). Yield: 40%; yellow solid; mp>260° C.; IR (KBr) $v_{max}$/cm$^{-1}$ 3240, 3171, 3088, 2228, 1623, 1591, 1555, 1509, 1465, 1393, 1273, 1229, 1149, 969, 919, 825; $^1$H NMR (300 MHz, DMSO-d$_6$) δ 8.54 (d, 1H, J=9.0 Hz), 8.43 (s, 1H), 7.74 (m, 2H), 7.55-7.53 (m, 3H); HRMS calcd for C$_{17}$H$_9$N$_6$S (M+H$^+$): 329.0609, found 329.0600.

9-(4-Methoxyphenylamino)thiazolo[5,4-f]quinazoline-2-carbonitrile VIIIda

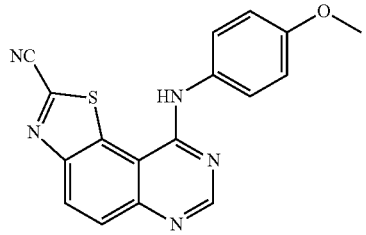 [SMILES: COc1ccc(Nc2ncnc3ccc4nc(C#N)sc4c23)cc1]

Prepared from VII and 4-methoxyaniline. Flash chromatography eluent (DCM-EtOAc, 8:2). Yield: 20%; orange solid, mp>260° C.; IR (KBr) $v_{max}$/cm$^{-1}$ 3346, 2977, 2361, 2227, 1644, 1609, 1581, 1503, 1460, 1377, 1354, 1303, 1239, 1164, 1129, 1051, 1032, 975, 829; $^1$H NMR (300 MHz, DMSO-d$_6$) δ 8.44 (s, 1H), 7.95 (d, 1H, J=9.0 Hz), 7.70 (d, 1H, J=9.0 Hz), 7.45 (d, 2H, J=9.0 Hz), 6.99 (d, 2H, J=9.0 Hz), 3.76 (s, 3H); HRMS calcd for C$_{17}$H$_{12}$N$_5$OS (M+H$^+$): 334.0763, found 334.0758.

9-(3,4,5-Trimethoxyphenylamino)thiazolo[5,4-f]quinazoline-2-carbonitrile VIIIea

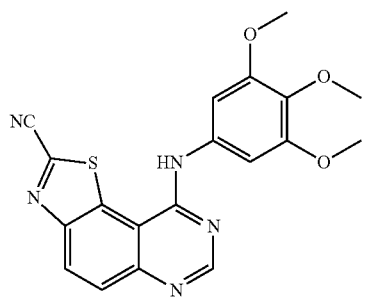 [SMILES: COc1cc(Nc2ncnc3ccc4nc(C#N)sc4c23)cc(OC)c1OC]

Prepared from VII and 3,4,5-trimethoxyaniline. Flash chromatography eluent (DCM-EtOAc, 5:5). Yield: 94%; pale yellow solid, mp 230° C.; IR (KBr) $v_{max}$/cm$^{-1}$ 3255, 3089, 3001, 2947, 2837, 2230, 1735, 1637, 1613, 1581, 1498, 1458, 1412, 1381, 1352, 1307, 1270, 1229, 1193, 1165, 1122, 1037, 1002, 991, 970, 952, 852, 830; $^1$H NMR (300 MHz, DMSO-d$_6$) δ 8.51 (d, 1H, J=9.0 Hz), 8.05 (s, 1H), 7.80 (d, 1H, J=9.0 Hz), 6.46 (s, 2H), 3.77 (s, 6H), 3.67 (s, 3H); HRMS calcd for C$_{19}$H$_{16}$N$_5$O$_3$S (M+H$^+$): 394.0974, found 394.0987.

9-(Benzo[d][1,3]dioxol-5-ylamino)thiazolo[5,4-f]quinazoline-2-carbonitrile VIIfa

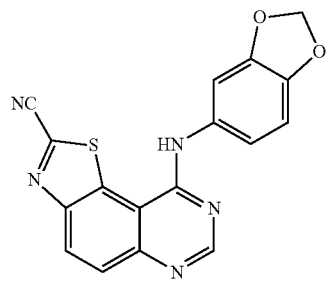 [SMILES: N#Cc1nc2ccc3ncnc(Nc4ccc5c(c4)OCO5)c3c2s1]

Prepared from VII and 3,4-(methylenedioxy)aniline. Flash chromatography eluent (DCM-EtOAc, 9:1). Yield: 49%; orange solid; mp>260° C.; IR (KBr) $v_{max}$/cm$^{-1}$ 2894, 2226, 1734, 1706, 1645, 1609, 1581, 1555, 1499, 1471, 1377, 1354, 1304, 1264, 1236, 1211, 1188, 1162, 1125, 1086, 1037, 972, 938, 924, 859, 829, 809; $^1$H NMR (300 MHz, DMSO-d$_6$) δ 8.51 (d, 1H, J=9.0 Hz), 8.14 (m, 1H), 7.76 (m, 1H), 6.94 (d, 2H, J=9.0 Hz), 6.72 (m, 1H), 6.02 (s, 2H); HRMS calcd for C$_{17}$H$_9$N$_5$O$_2$S (M+H$^+$): 348.0555, found 348.0566.

9-(4-Bromobenzo[d][1,3]dioxol-5-ylamino)thiazolo[5,4-f]quinazoline-2-carbonitrile VIIIga

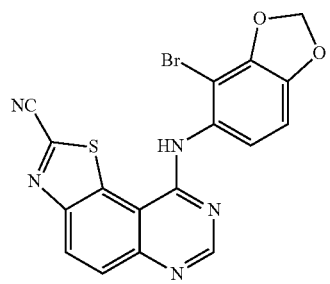 [SMILES: N#Cc1nc2ccc3ncnc(Nc4ccc5c(c4Br)OCO5)c3c2s1]

Prepared from VII and 2-bromo-3,4-(methylenedioxy)aniline. Flash chromatography eluent (DCM-EtOAc, 5:5). Yield: 21%; yellow solid, mp>260° C.; IR (KBr) $v_{max}$/cm$^{-1}$ 2887, 2233, 1632, 1610, 1581, 1501, 1484, 1465, 1379, 1348, 1303, 1267, 1232, 1161, 1116, 1034, 970, 929, 829; $^1$H NMR (300 MHz, DMSO-d$_6$) δ 8.49 (d, 1H, J=9.0 Hz), 8.06 (s, 1H), 7.77 (d, 1H, J=9.0 Hz), 7.25 (s, 1H), 6.83 (s, 1H), 6.06 (s, 2H); HRMS calcd for C$_{17}$H$_9$N$_5$O$_2$SBr (M+H$^+$): 425.9660, found 425.9646.

9-(2,3-Dihydrobenzo[b][1,4]dioxin-6-ylamino)thiazolo[5,4-f]quinazoline-2-carbonitrile VIIIha

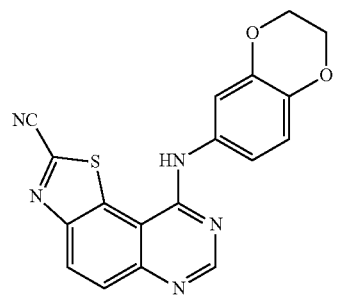 [SMILES: N#Cc1nc2ccc3ncnc(Nc4ccc5c(c4)OCCO5)c3c2s1]

Prepared from VII and 1,4-benzodioxan-6-amine. Flash chromatography eluent (DCM-EtOAc, 8:2). Yield: 33%; yellow solid; mp 180-190° C.; IR (KBr) $v_{max}$/cm$^{-1}$ 3055, 2978, 2932, 2875, 2230, 1709, 1638, 1609, 1578, 1496, 1460, 1376, 1299, 1281, 1239, 1200, 1151, 1063, 916, 885, 814; $^1$H NMR (300 MHz, DMSO-d$_6$) δ 8.37 (d, 1H, J=8.4 Hz), 7.85 (m, 1H), 7.76 (m, 1H), 6.88 (d, 1H, J=8.4 Hz), 6.56 (m, 2H), 4.25 (s, 4H); HRMS calcd for C$_{18}$H$_{12}$N$_5$O$_2$S (M+H$^+$): 362.0712, found 362.0696.

9-(3,4-Dimethoxyphenylamino)thiazolo[5,4-f]quinazoline-2-carbonitrile VIIIia

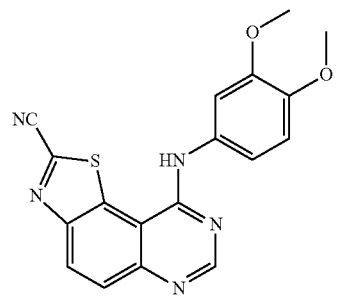 [SMILES: COc1ccc(Nc2ncnc3ccc4nc(C#N)sc4c23)cc1OC]

Prepared from VII and 3,4-dimethoxyaniline. Flash chromatography eluent (DCM-EtOAc, 8:2). Yield: 74%; yellow solid; mp>260° C.; IR (KBr) $v_{max}$/cm$^{-1}$ 3267, 2839, 2226, 1644, 1610, 1583, 1507, 1460, 1443, 1379, 1308, 1260, 1227, 1201, 1166, 1150, 1129, 1020, 967, 935, 861, 839; $^1$H NMR (300 MHz, DMSO-d$_6$) δ 8.34 (m, 1H), 7.79 (m, 1H), 7.71 (m, 1H), 6.90 (d, 1H, J=8.1 Hz), 6.54 (m, 2H), 4.26 (s, 6H); HRMS calcd for C$_{18}$H$_{14}$N$_5$O$_2$S (M+H$^+$): 364.0868, found 364.0850.

9-(4-Hydroxyphenylamino)thiazolo[5,4-f]quinazoline-2-carbonitrile VIIIja

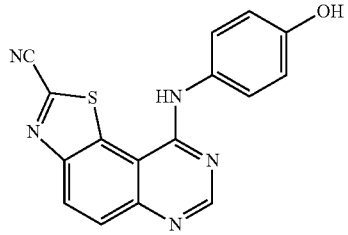

Prepared from VII and 4-aminophenol. Flash chromatography eluent (EtOAc). Yield: 80%; orange solid; mp 236° C.; IR (KBr) $v_{max}$/cm$^{-1}$ 3072, 2225, 1641, 1615, 1577, 1503, 1464, 1378, 1350, 1307, 1230, 1212, 1159, 1097, 972, 832; $^1$H NMR (300 MHz, DMSO-d$_6$) δ 8.48 (d, 1H, J=8.7 Hz), 8.08 (m, 1H), 7.76 (d, 1H, J=8.7 Hz), 7.15 (m, 2H), 6.79 (m, 2H); HRMS calcd for $C_{16}H_{10}N_5OS$ (M+H$^+$): 320.0606, found 320.0619.

9-(3-Hydroxy-4-methoxyphenylamino)thiazolo[5,4-f]quinazoline-2-carbonitrile VIIIka

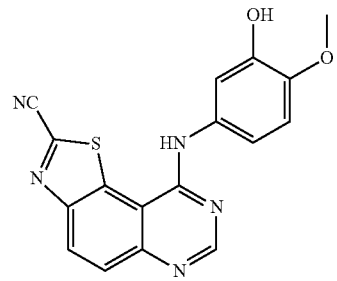 [SMILES: COc1ccc(Nc2ncnc3ccc4nc(C#N)sc4c23)cc1O]

Prepared from VII and 5-amino-2-methoxyphenol. Flash chromatography eluent (EtOAc). Yield: 54%; yellow solid; mp 248° C.; IR (KBr) $v_{max}$/cm$^{-1}$ 2921, 2851, 2227, 1724, 1647, 1616, 1583, 1509, 1460, 1334, 1287, 1263, 1218, 1172, 1148, 1120, 1036, 973, 953, 864, 833; $^1$H NMR (300 MHz, DMSO-d$_6$) δ 8.49 (d, 1H, J=8.7 Hz), 8.05 (m, 1H), 7.77 (d, 1H, J=8.7 Hz), 7.94 (d, 2H, J=8.7 Hz), 6.65 (m, 1H), 3.77 (s, 3H); HRMS calcd for $C_{17}H_{12}N_5O_2S$ (M+H$^+$): 350.0712, found 350.0715.

9-(2,3-Dihydrobenzofuran-5-ylamino)thiazolo[5,4-f]quinazoline-2-carbonitrile VIIIla

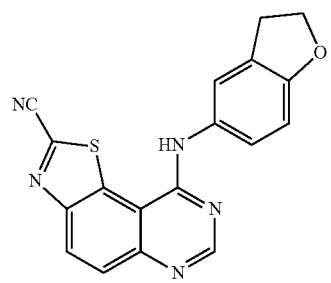 [SMILES: N#Cc1nc2ccc3ncnc(Nc4ccc5c(c4)CCO5)c3c2s1]

Prepared from VII and 2,3-dihydro-1-benzofuran-5-amine. Flash chromatography eluent (EtOAc). Yield: 95%; yellow solid; mp 216° C.; IR (KBr) $v_{max}$/cm$^{-1}$ 2894, 2853, 2228, 1643, 1609, 1579, 1484, 1467, 1376, 1353, 1306, 1269, 1219, 1192, 1164, 1123, 978, 941, 881, 814; $^1$H NMR (300 MHz, DMSO-d$_6$) δ 8.49 (d, 1H, J=8.7 Hz), 8.10 (s, 1H), 7.75 (d, 1H, J=8.7 Hz), 7.22 (m, 1H), 7.04 (s, 1H), 6.78 (m, 1H), 4.53 (t, 2H, J=8.7 Hz), 3.20 (t, 1H, J=8.7 Hz); HRMS calcd for $C_{18}H_{12}N_5OS$ (M+H$^+$): 346.0763, found 346.0762.

9-(4-Chlorophenylamino)thiazolo[5,4-f]quinazoline-2-carbonitrile VIIIma

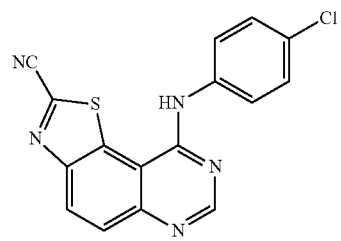 [SMILES: N#Cc1nc2ccc3ncnc(Nc4ccc(Cl)cc4)c3c2s1]

Prepared from VII and 4-chloroaniline. Flash chromatography eluent (DCM-EtOAc, 5:5). Yield: 89%; yellow solid; mp>260° C.; IR (KBr) $v_{max}$/cm$^{-1}$ 2850, 2229, 1643, 1609, 1583, 1550, 1491, 1480, 1457, 1377, 1355, 1307, 1270, 1214, 1164, 1130, 1092, 1010, 980, 831; $^1$H NMR (300 MHz, DMSO-d$_6$) δ 8.51 (d, 1H, J=8.7 Hz), 8.18 (s, 1H), 7.76 (d, 1H, J=8.7 Hz), 7.38 (m, 2H), 7.04 (m, 2H); HRMS calcd for $C_{16}H_9N_5SCl$ (M+H$^+$): 338.0267, found 338.0274.

9-(3,4-Dichlorophenylamino)thiazolo[5,4-f]quinazoline-2-carbonitrile VIIIna

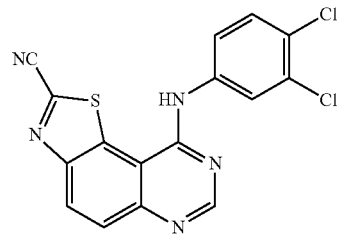 [SMILES: N#Cc1nc2ccc3ncnc(Nc4ccc(Cl)c(Cl)c4)c3c2s1]

Prepared from VII and 3,4-dichloroaniline. Flash chromatography eluent (DCM-EtOAc, 7:3). Yield: 42%; yellow solid; mp>260° C.; IR (KBr) $v_{max}$/cm$^{-1}$ 2851, 2225, 1644, 1612, 1579, 1456, 1378, 1355, 1308, 1270, 1241, 1168, 1122, 1026, 971, 879, 834, 816; $^1$H NMR (300 MHz, DMSO-d$_6$) δ 8.55 (d, 1H, J=8.7 Hz), 8.30 (s, 1H), 7.78 (d, 1H, J=8.7 Hz), 7.63-7.53 (m, 2H), 7.30 (m, 2H); HRMS calcd for $C_{16}H_8N_5SCl_2$ (M+H$^+$): 371.9877, found 371.9882.

9-(3-Ethynylphenylamino)thiazolo[5,4-f]quinazoline-2-carbonitrile VIIIoa

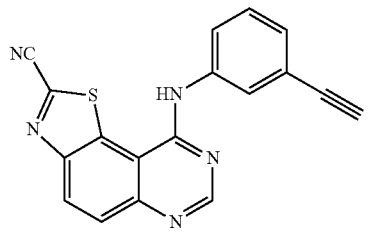 [SMILES: C#Cc1cccc(Nc2ncnc3ccc4nc(C#N)sc4c23)c1]

Prepared from VII and 3-ethynylaniline. Flash chromatography eluent (DCM-EtOAc, 7:3). Yield: 84%; yellow solid; mp 182° C.; IR (KBr) $v_{max}$/cm$^{-1}$ 3295, 3062, 2846, 2225, 1642, 1612, 1581, 1566, 1458, 1404, 1376, 1348, 1306, 1263, 1229, 1165, 1148, 1126, 971, 910, 888, 835; $^1$H NMR (300 MHz, DMSO-d$_6$) δ 8.53 (d, 1H, J=8.7 Hz), 8.20 (s, 1H), 7.78 (d, 1H, J=8.7 Hz), 7.40-7.35 (m, 2H), 7.29 (m, 1H), 7.20 (m, 1H), 4.17 (s, 1H); HRMS calcd for C$_{18}$H$_{10}$N$_5$S (M+H$^+$): 328.0657, found 328.0659.

9-(1H-Benzo[d]imidazol-6-ylamino)thiazolo[5,4-f]quinazoline-2-carbonitrile VIIIpa

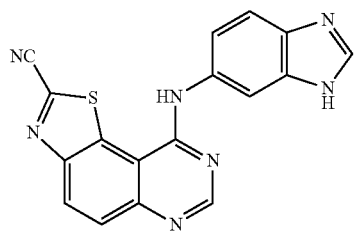 [SMILES: N#Cc1nc2ccc3ncnc(Nc4ccc5nc[nH]c5c4)c3c2s1]

Prepared from VII and 6-aminobenzimidazole. Flash chromatography eluent (DCM-MeOH 8:2). Yield: 98%; yellow solid; mp>260° C.; IR (KBr) $v_{max}$/cm$^{-1}$ 3084, 2226, 1615, 1557, 1464, 1376, 1347, 1248, 1147, 967, 939, 809; $^1$H NMR (300 MHz, DMSO-d$_6$) δ 8.48 (d, 1H, J=8.7 Hz), 8.15-8.10 (m, 2H), 8.02 (m, 1H), 7.75 (d, 1H, J=8.7 Hz), 7.56 (m, 1H), 7.04 (m, 1H); HRMS calcd for C$_{17}$H$_{10}$N$_7$S (M+H$^+$): 344.0718, found 344.0705.

9-(4-Hydroxy-3-nitrophenylamino)thiazolo[5,4-f]quinazoline-2-carbonitrile VIIIqa

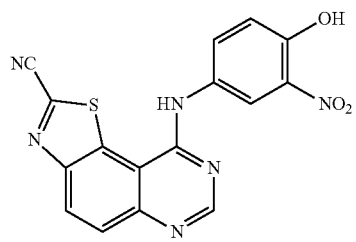 [SMILES: N#Cc1nc2ccc3ncnc(Nc4ccc(O)c([N+](=O)[O-])c4)c3c2s1]

Prepared from VII and 4-amino-2-nitrophenol. Flash chromatography eluent (DCM-EtOAc, 5:5). Yield: 60%; brown solid; mp>260° C.; IR (KBr) $v_{max}$/cm$^{-1}$ 3334, 3081, 2926, 2225, 1627, 1591, 1569, 1525, 1465, 1419, 1395, 1305, 1237, 1171, 1132, 1070, 966, 930, 834, 819; $^1$H NMR (300 MHz, DMSO-d$_6$) δ 8.52 (d, 1H, J=8.7 Hz), 8.28 (m, 1H), 8.03 (m, 1H), 7.75 (d, 1H, J=8.7 Hz), 7.61 (m, 1H), 7.15 (d, 1H, J=9.0 Hz); HRMS calcd for C$_{16}$H$_9$N$_6$O$_3$S (M+H$^+$): 365.0457, found 365.0441.

9-(2,4-Dimethoxyphenylamino)thiazolo[5,4-f]quinazoline-2-carbonitrile VIIIra

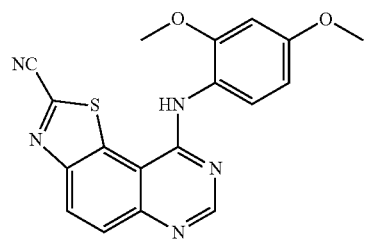 [SMILES: COc1ccc(Nc2ncnc3ccc4nc(C#N)sc4c23)c(OC)c1]

Prepared from VII and 2,4-dimethoxyaniline. Flash chromatography eluent (DCM-EtOAc, 5:5). Yield: 59%; orange solid; mp 255-257° C.; IR (KBr) $v_{max}$/cm$^{-1}$ 3401, 3081, 2948, 2837, 2233, 1600, 1565, 1540, 1525, 1505, 1443, 1417, 1329, 1278, 1231, 1203, 1159, 1132, 1088, 1030, 959, 915; $^1$H NMR (300 MHz, DMSO-d$_6$) δ 8.51 (d, 1H, J=9.0 Hz), 7.98 (s, 1H), 7.83 (d, 1H, J=9.0 Hz), 6.95 (m, 1H), 6.67 (s, 1H), 6.58 (d, 1H, J=9.0 Hz), 3.78 (s, 3H), 3.73 (s, 3H); HRMS calcd for C$_{18}$H$_{14}$N$_5$O$_2$S (M+H$^+$): 364.0868, found 364.0856.

9-(3,5-Dimethoxyphenylamino)thiazolo[5,4-f]quinazoline-2-carbonitrile VIIIsa

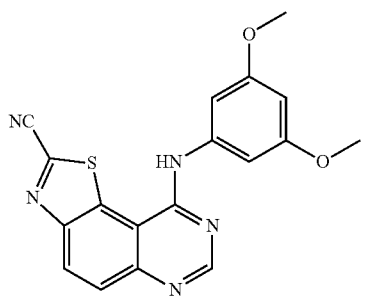 [SMILES: COc1cc(Nc2ncnc3ccc4nc(C#N)sc4c23)cc(OC)c1]

Prepared from VII and 3,5-dimethoxyaniline. Flash chromatography eluent (DCM-EtOAc, 5:5). Yield: 98%; yellow solid; mp 248° C.; IR (KBr) $v_{max}$/cm$^{-1}$ 3242, 2940, 2837, 2223, 1711, 1647, 1578, 1455, 1419, 1383, 1357, 1306, 1265, 1205, 1144, 1058, 1046, 968, 943, 917, 833, 806; $^1$H NMR (300 MHz, DMSO-d$_6$) δ 8.51 (d, 1H, J=9.0 Hz), 8.06 (s, 1H), 7.79 (d, 1H, J=9.0 Hz), 6.31 (m, 3H), 3.74 (s, 6H); HRMS calcd for C$_{18}$H$_{14}$N$_5$O$_2$S (M+H$^+$): 364.0868, found 364.0856.

9-(Phenylamino)thiazolo[5,4-f]quinazoline-2-carbonitrile VIIIta

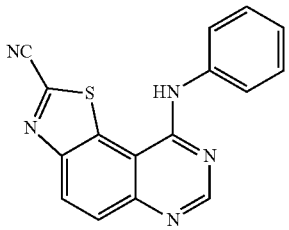 [SMILES: N#Cc1nc2ccc3ncnc(Nc4ccccc4)c3c2s1]

Prepared from VII and aniline. Flash chromatography eluent (DCM-EtOAc, 5:5). Yield: 67%; yellow solid; mp>260° C.; IR (KBr) $v_{max}$/cm$^{-1}$ 3395, 3057, 2228, 1731, 1644, 1608, 1577, 1491, 1459, 1378, 1352, 1301, 1255, 1214, 1147, 1128, 1106, 1071, 967, 896, 827; $^1$H NMR (300 MHz, DMSO-d$_6$) δ 8.51 (d, 1H, J=9.0 Hz), 8.11 (s, 1H), 7.78 (d, 1H, J=9.0 Hz), 7.40 (t, 2H, J=7.5 Hz), 7.20 (m, 2H), 7.11 (t, 1H, J=7.5 Hz); HRMS calcd for $C_{16}H_{10}N_5S$ (M+H$^+$): 304.0657, found 304.0657.

9-(p-Tolylamino)thiazolo[5,4-f]quinazoline-2-carbonitrile VIIIua

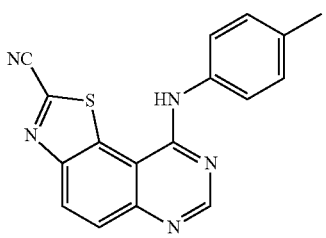 [SMILES: Cc1ccc(Nc2ncnc3ccc4nc(C#N)sc4c23)cc1]

Prepared from VII and 4-toluidine. Flash chromatography eluent (DCM-EtOAc, 7:3). Yield: 64%; yellow solid; mp>260° C.; IR (KBr) $v_{max}$/cm$^{-1}$ 3016, 2853, 2228, 1731, 1641, 1605, 1581, 1554, 1505, 1458, 1376, 1353, 1304, 1268, 1215, 1165, 1130, 976, 831, 811; $^1$H NMR (300 MHz, DMSO-d$_6$) δ 8.49 (d, 1H, J=9.0 Hz), 8.07 (s, 1H), 7.76 (d, 1H, J=9.0 Hz), 7.20-7.17 (m, 2H), 7.12-7.05 (m, 2H), 2.32 (s, 3H); HRMS calcd for $C_{17}H_{12}N_5S$ (M+H$^+$): 318.0813, found 318.0811.

9-(4-Fluorophenylamino)thiazolo[5,4-f]quinazoline-2-carbonitrile VIIIva

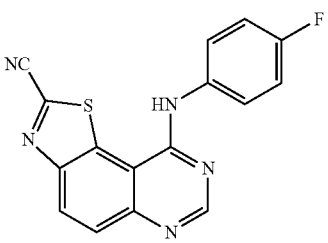 [SMILES: N#Cc1nc2ccc3ncnc(Nc4ccc(F)cc4)c3c2s1]

Prepared from VII and 4-fluoroaniline. Flash chromatography eluent (DCM-EtOAc, 5:5). Yield: 92%; yellow solid; mp>260° C.; IR (KBr) $v_{max}$/cm$^{-1}$ 3049, 2840, 2226, 1722, 1643, 1610, 1581, 1557, 1502, 1377, 1355, 1305, 1269, 1227, 1208, 1166, 1130, 1090, 981, 846, 829, 818; $^{19}$F NMR (282 MHz, DMSO-d$_6$) δ −120.31; $^1$H NMR (300 MHz, DMSO-d$_6$) δ 8.51 (d, 1H, J=9.0 Hz), 8.16 (s, 1H), 7.76 (d, 1H, J=9.0 Hz), 7.26-7.08 (m, 4H); HRMS calcd for $C_{16}H_9N_5SF$ (M+H$^+$): 322.0563, found 322.0551.

9-(2-Bromo-4-fluorophenylamino)thiazolo[5,4-f]quinazoline-2-carbonitrile VIIIwa

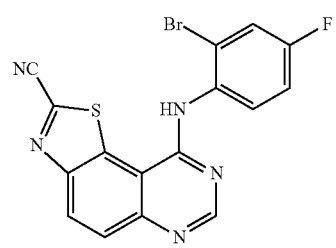 [SMILES: N#Cc1nc2ccc3ncnc(Nc4ccc(F)cc4Br)c3c2s1]

Prepared from VII and 2-bromo-4-fluoroaniline. Flash chromatography eluent (DCM-EtOAc, 95:5). Yield: 44%; yellow solid; mp>260° C.; IR (KBr) $v_{max}$/cm$^{-1}$ 3068, 2853, 2228, 1736, 1644, 1611, 1582, 1497, 1474, 1459, 1380, 1353, 1309, 1252, 1188, 1171, 1127, 1050, 1031, 980, 881, 860, 826; $^{19}$F NMR (282 MHz, DMSO-d$_6$) δ −119.33; $^1$H NMR (300 MHz, DMSO-d$_6$) δ 8.56 (d, 1H, J=9.0 Hz), 8.18 (s, 1H), 7.81 (d, 1H, J=9.0 Hz), 7.63 (d, 1H, J=7.8 Hz) 7.24-7.17 (m, 2H); HRMS calcd for $C_{16}H_8N_5SBrF$ (M+H$^+$): 399.9668, found 399.9675.

9-(2-Fluoro-4-methoxyphenylamino)thiazolo[5,4-f]quinazoline-2-carbonitrile VIIIxa

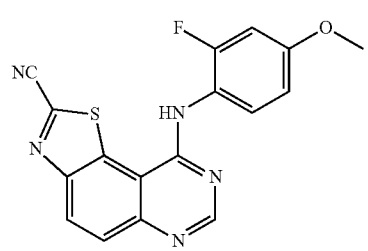 [SMILES: COc1ccc(Nc2ncnc3ccc4nc(C#N)sc4c23)c(F)c1]

Prepared from VII and 2-fluoro-4-methoxyaniline. Flash chromatography eluent (DCM-EtOAc, 5:5). Yield: 85%; yellow solid; mp>260° C.; IR (KBr) $v_{max}$/cm$^{-1}$ 2844, 2226, 1731, 1649, 1613, 1583, 1507, 1493, 1460, 1445, 1379, 1356, 1305, 1263, 1212, 1168, 1153, 1129, 1090, 1027, 980, 947, 841, 830, 818; $^{19}$F NMR (282 MHz, DMSO-d$_6$) δ −120.02; $^1$H NMR (300 MHz, DMSO-d$_6$) δ 8.51 (d, 1H, J=9.0 Hz), 8.15 (s, 1H), 7.77 (d, 1H, J=9.0 Hz), 7.30 (s, 1H), 6.92 (m, 1H), 6.80 (d, 2H, J=9.0 Hz); HRMS calcd for $C_{17}H_{11}N_5OSF$ (M+H$^+$): 352.0668, found 352.0658.

9-(4-Cyanophenylamino)thiazolo[5,4-f]quinazoline-2-carbonitrile VIIIya

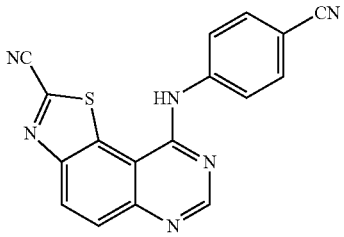

Prepared from VII and 4-aminobenzonitrile. Flash chromatography eluent (DCM-EtOAc, 5:5). Yield: 36%; yellow solid; mp>260° C.; IR (KBr) $v_{max}$/cm$^{-1}$ 3293, 2225, 2218, 1722, 1628, 1590, 1562, 1495, 1461, 1387, 1261, 1228, 1132, 966, 847, 814; $^1$H NMR (300 MHz, DMSO-d$_6$) δ 8.54 (d, 1H, J=9.0 Hz), 8.28 (s, 1H), 7.77 (m, 3H), 7.40 (d, 2H, J=9.0 Hz); HRMS calcd for C$_{17}$H$_9$N$_6$S (M+H$^+$): 329.0609, found 329.0612.

9-(4-Chloro-2-fluorophenylamino)thiazolo[5,4-f]quinazoline-2-carbonitrile VIIIza

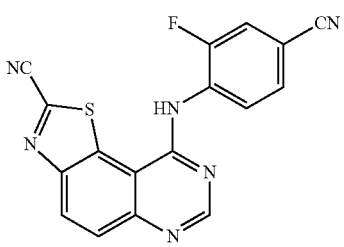 [SMILES: N#Cc1ccc(Nc2ncnc3ccc4nc(C#N)sc4c23)c(F)c1]

Prepared from VII and 4-chloro-2-fluoroaniline. Flash chromatography eluent (DCM-EtOAc, 8:2). Yield: 56%; yellow solid; mp>260° C.; IR (KBr) $v_{max}$/cm$^{-1}$ 2231, 1638, 1614, 1583, 1476, 1413, 1380, 1356, 1309, 1273, 1200, 1170, 1120, 982, 901, 838, 820; $^1$H NMR (300 MHz, DMSO-d$_6$) δ 8.55 (d, 1H, J=9.0 Hz), 8.24 (s, 1H), 7.79 (d, 1H, J=9.0 Hz), 7.45 (d, 1H, J=9.0 Hz), 7.34 (t, 1H, J=8.4 Hz), 7.26 (d, 1H, J=9.0 Hz); HRMS calcd for C$_{16}$H$_8$N$_5$SClF (M+H$^+$): 356.0173, found 356.0160.

9-(2,4-Dichlorophenylamino)thiazolo[5,4-f]quinazoline-2-carbonitrile VIIIab

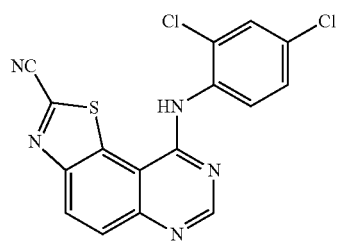 [SMILES: N#Cc1nc2ccc3ncnc(Nc4ccc(Cl)cc4Cl)c3c2s1]

Prepared from VII and 2,4-dichloroaniline. Flash chromatography eluent (DCM-EtOAc, 5:5). Yield: 32%; yellow solid; mp>260° C.; IR (KBr) $v_{max}$/cm$^{-1}$ 3063, 2231, 1736, 1644, 1611, 1577, 1459, 1380, 1355, 1310, 1242, 1173, 1098, 1051, 983, 830, 818; $^1$H NMR (300 MHz, DMSO-d$_6$) δ 8.56 (d, 1H, J=9.0 Hz), 8.21 (s, 1H), 7.80 (d, 1H, J=9.0 Hz), 7.63 (s, 1H), 7.39 (d, 1H, J=8.1 Hz), 7.25 (d, 1H, J=8.1 Hz); HRMS calcd for C$_{16}$H$_8$N$_5$SCl$_2$ (M+H$^+$): 371.9877, found 371.9877.

9-(4-Methoxy-3-nitrophenylamino)thiazolo[5,4-f]quinazoline-2-carbonitrile VIIIbb

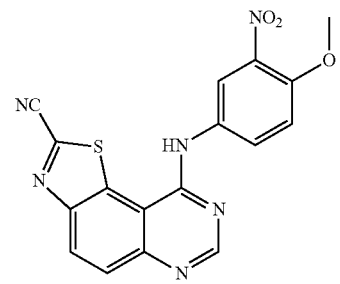 [SMILES: COc1ccc(Nc2ncnc3ccc4nc(C#N)sc4c23)cc1[N+](=O)[O-]]

Prepared from VII and 3-nitro-4-methoxyaniline. Flash chromatography eluent (DCM-EtOAc, 7:3). Yield: 61%; yellow solid; mp 200-260° C.; IR (KBr) $v_{max}$/cm$^{-1}$ 2226, 1644, 1523, 1459, 1346, 1267, 1191, 1155, 1075, 1015, 970, 928, 890, 822; $^1$H NMR (300 MHz, DMSO-d$_6$) δ 8.47 (d, 1H, J=9.0 Hz), 8.26 (s, 1H), 7.97 (d, 1H, J=9.0 Hz), 7.70 (s, 2H), 7.32 (d, 1H, J=9.0 Hz), 3.93 (s, 3H); HRMS calcd for C$_{17}$H$_{11}$N$_6$O$_3$S (M+H$^+$): 379.0613, found 379.0614.

9-(4-tert-Butylbenzylamino)thiazolo[5,4-f]quinazoline-2-carbonitrile VIIIcb

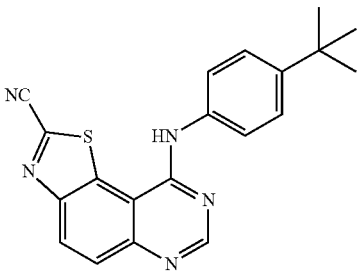 [SMILES: CC(C)(C)c1ccc(Nc2ncnc3ccc4nc(C#N)sc4c23)cc1]

Prepared from VII and 4-tert-butylaniline. Flash chromatography eluent (DCM-EtOAc, 7:3). Yield: 99%; yellow solid; mp 154° C.; IR (KBr) $v_{max}$/cm$^{-1}$ 2958, 2235, 1693, 1649, 1582, 1505, 1466, 1408, 1349, 1288, 1219, 1155, 1125, 989, 968, 894, 831; $^1$H NMR (300 MHz, DMSO-d$_6$) δ 8.49 (d, 1H, J=9.0 Hz), 8.07 (s, 1H), 7.76 (d, 1H, J=9.0 Hz), 7.40 (d, 2H, J=7.8 Hz), 7.12 (m, 2H), 1.31 (s, 9H); HRMS calcd for C$_{20}$H$_{18}$N$_5$S (M+H$^+$): 360.1283, found 360.1273.

9-(3-Chlorophenylamino)thiazolo[5,4-f]quinazoline-2-carbonitrile VIIIdb

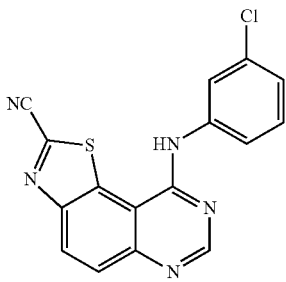 [SMILES: N#Cc1nc2ccc3ncnc(Nc4cccc(Cl)c4)c3c2s1]

Prepared from VII and 3-chloroaniline. Flash chromatography eluent (DCM-EtOAc, 7:3). Yield: 74%; pale yellow solid; mp>260° C.; IR (KBr) $\nu_{max/cm}^{-1}$ 2849, 2226, 1643, 1611, 1577, 1461, 1377, 1354, 1306, 1218, 1161, 1128, 1070, 974, 875, 833; $^1$H NMR (300 MHz, DMSO-$d_6$) δ 8.49 (d, 1H, J=9.0 Hz), 8.21 (s, 1H), 7.74 (d, 1H, J=9.0 Hz), 7.40-7.35 (m, 2H), 7.19-7.11 (m, 2H); HRMS calcd for $C_{16}H_9N_5SCl$ (M+H$^+$): 338.0267, found 338.0259.

9-(4-(Dimethylamino)phenylamino)thiazolo[5,4-f]quinazoline-2-carbonitrile VIIIeb

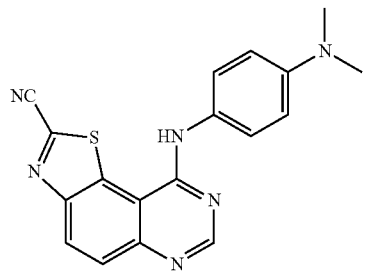 [SMILES: CN(C)c1ccc(Nc2ncnc3ccc4nc(C#N)sc4c23)cc1]

Prepared from VII and N,N-dimethyl-p-phenylene-diamine. Flash chromatography eluent (DCM-EtOAc, 8:2). Yield: 25%; yellow solid; mp>260° C.; IR (KBr) $\nu_{max}/cm^{-1}$ 3293, 2228, 1609, 1572, 1523, 1460, 1368, 1274, 1229, 1204, 1188, 1163, 1141, 1058, 1009, 948, 842, 811; $^1$H NMR (300 MHz, DMSO-$d_6$) δ 8.52 (d, 1H, J=9.0 Hz), 8.16 (s, 1H), 7.86 (d, 1H, J=9.0 Hz), 7.37 (d, 2H, J=8.7 Hz), 6.92 (d, 2H, J=8.7 Hz), 3.00 (s, 6H); HRMS calcd for $C_{18}H_{15}N_6S$ (M+H$^+$): 347.1079, found 347.1066.

9-(4-(Pyrrolidin-1-yl)phenylamino)thiazolo[5,4-f]quinazoline-2-carbonitrile VIIIfb

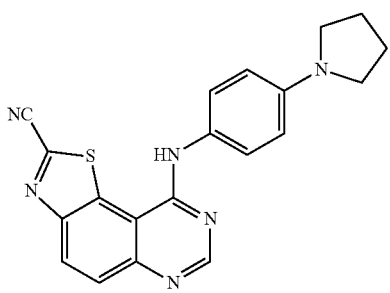 [SMILES: N#Cc1nc2ccc3ncnc(Nc4ccc(N5CCCC5)cc4)c3c2s1]

Prepared from VII and 4-(pyrrolidin-1-yl)aniline. Flash chromatography eluent (DCM-EtOAc, 8:2). Yield: 48%; yellow solid; mp>260° C.; IR (KBr) $\nu_{max}/cm^{-1}$ 3303, 2842, 2233, 1709, 1629, 1613, 1583, 1522, 1466, 1388, 1347, 1275, 1219, 1185, 1166, 1060, 1014, 989, 828, 809; $^1$H NMR (300 MHz, DMSO-$d_6$) δ 8.54 (d, 1H, J=9.0 Hz), 8.15 (s, 1H), 7.88 (d, 1H, J=9.0 Hz), 7.35 (d, 2H, J=8.1 Hz), 6.73 (d, 2H, J=8.1 Hz), 3.17 (m, 4H), 1.99 (m, 4H); HRMS calcd for $C_{20}H_{17}N_6S$ (M+H$^+$): 373.1235, found 373.1218.

9-(2,4-Difluorophenylamino)thiazolo[5,4-f]quinazoline-2-carbonitrile VIIIgb

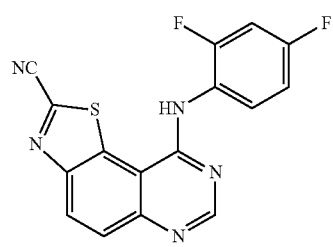 [SMILES: N#Cc1nc2ccc3ncnc(Nc4ccc(F)cc4F)c3c2s1]

Prepared from VII and 2,4-difluoroaniline. Flash chromatography eluent (DCM-EtOAc, 7:3). Yield: 68%; yellow solid; mp>260° C.; IR (KBr) $\nu_{max}/cm^{-1}$ 2228, 1645, 1611, 1583, 1557, 1488, 1460, 1378, 1357, 1311, 1276, 1260, 1172, 1138, 1091, 962, 854, 831, 818; $^{19}$F NMR (282 MHz, DMSO-$d_6$) δ −117.6, −118.7; $^1$H NMR (300 MHz, DMSO-$d_6$) δ 8.54 (d, 1H, J=9.0 Hz), 8.22 (s, 1H), 7.78 (d, 1H, J=9.0 Hz), 7.35-7.24 (m, 2H), 7.06 (t, 1H, J=7.8 Hz); HRMS calcd for $C_{16}H_8N_5SF_2$ (M+H$^+$): 340.0468, found 340.0458.

9-(3-Fluoro-4-hydroxyphenylamino)thiazolo[5,4-f]quinazoline-2-carbonitrile VIIIhb

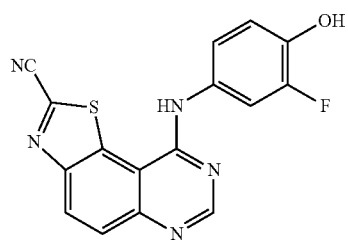 [SMILES: N#Cc1nc2ccc3ncnc(Nc4ccc(O)c(F)c4)c3c2s1]

Prepared from VII and 4-amino-2-fluorophenol. Flash chromatography eluent (DCM-EtOAc, 5:5). Yield: 58%; orange solid; mp>260° C.; IR (KBr) $\nu_{max}/cm^{-1}$ 3375, 2228, 1731, 1649, 1619, 1578, 1512, 1470, 1373, 1347, 1292, 1241, 1204, 1150, 1111, 978, 943, 856, 836; $^{19}$F NMR (282 MHz, DMSO-$d_6$) δ −136.8; $^1$H NMR (300 MHz, DMSO-$d_6$) δ 8.46 (d, 1H, J=9.0 Hz), 8.15 (s, 1H), 7.69 (d, 1H, J=9.0 Hz), 6.97-6.81 (m, 3H); HRMS calcd for $C_{16}H_9N_5OSF$ (M+H$^+$): 338.0512, found 338.0516.

9-(4-(Trifluoromethyl)phenylamino)thiazolo[5,4-f]quinazoline-2-carbonitrile VIIIib

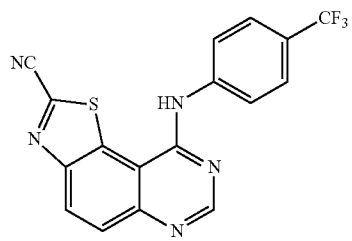 [SMILES: N#Cc1nc2ccc3ncnc(Nc4ccc(C(F)(F)F)cc4)c3c2s1]

Prepared from VII and 4-aminobenzotrifluoride. Flash chromatography eluent (DCM-EtOAc, 7:3). Yield: 61%; yellow solid; mp>260° C.; IR (KBr) $v_{max}$/cm$^{-1}$ 2851, 2229, 1649, 1604, 1582, 1512, 1457, 1382, 1318, 1272, 1252, 1221, 1165, 1117, 1101, 1062, 1011, 979, 863, 830; $^{19}$F NMR (282 MHz, DMSO-d$_6$) δ −60.01; $^1$H NMR (300 MHz, DMSO-d$_6$) δ 8.53 (d, 1H, J=9.0 Hz), 8.22 (s, 1H), 7.77 (d, 1H, J=9.0 Hz), 7.70 (d, 2H, J=8.4 Hz), 7.39 (d, 2H, J=8.4 Hz); HRMS calcd for C$_{17}$H$_9$N$_5$SF$_3$ (M+H$^+$): 372.0529, found 372.0535.

General Procedure for the Synthesis of N-methylated-thiazolo[5,4-f]quinazoline-2-carbonitriles IXa-c Methyl iodide (0.90 mmol) was added dropwise to a stirred suspension of carbonitrile VIIIia, VIIIda, VIIIha (0.60 mmol) and sodium hydride (0.90 mmol, 60% dispersion in mineral oil) in dimethylformamide (4 mL). The mixture was stirred for 1 h at 0° C. and then for 2 h at room temperature. After cooling, the resulting mixture was concentrated under reduced pressure. The crude residue obtained was purified by flash chromatography (DCM-ethyl acetate, 1:9) to give IXa-c.

9-((3,4-Dimethoxyphenyl)(methyl)amino)thiazolo[5,4-f]quinazoline-2-carbonitrile IXa

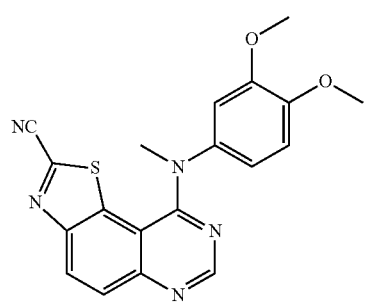 [SMILES: COc1ccc(N(C)c2ncnc3ccc4nc(C#N)sc4c23)cc1OC]

Prepared from carbonitrile VIIIia. Flash chromatography eluent (EtOAc). Yield: 74%; orange solid; mp 224° C.; IR (KBr) $v_{max}$/cm$^{-1}$ 3040, 2988, 2957, 2828, 2225, 1621, 1553, 1501, 1442, 1409, 1392, 1366, 1255, 1227, 1201, 1173, 1142, 1123, 1023, 936, 872, 803; $^1$H NMR (300 MHz, DMSO-d$_6$) δ 8.56 (d, 1H, J=9.0 Hz), 8.29 (s, 1H), 7.85 (d, 1H, J=9.0 Hz), 7.17 (d, 1H, J=2.1 Hz), 7.08 (dd, 1H, J$_1$=2.1 Hz, J$_2$=8.7 Hz), 6.93 (d, 1H, J=8.7 Hz), 3.77 (m, 9H); HRMS calcd for C$_{19}$H$_{16}$N$_5$O$_2$S (M+H$^+$): 378.1025, found 378.1008.

9-((4-Methoxyphenyl)(methyl)amino)thiazolo[5,4-f]quinazoline-2-carbonitrile IXb

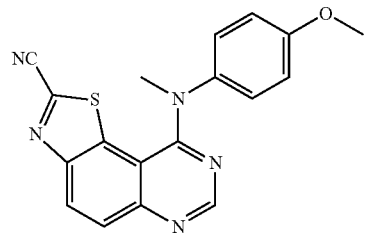 [SMILES: COc1ccc(N(C)c2ncnc3ccc4nc(C#N)sc4c23)cc1]

Prepared from carbonitrile VIIIda. Flash chromatography eluent (EtOAc). Yield: 60%; orange solid; mp>260° C.; IR (KBr) $v_{max}$/cm$^{-1}$ 3073, 2949, 2908, 2835, 2225, 1615, 1551, 1497, 1481, 1461, 1452, 1436, 1362, 1235, 1153, 1060, 1031, 974, 839, 825, 801; $^1$H NMR (300 MHz, DMSO-d$_6$) δ 8.49 (d, 1H, J=9.0 Hz), 8.23 (s, 1H), 7.88 (d, 1H, J=9.0 Hz), 7.48 (d, 1H, J=8.7 Hz), 6.92 (d, 1H, J=8.7 Hz), 3.77 (s, 3H), 3.73 (s, 3H); HRMS calcd for C$_{18}$H$_{14}$N$_5$OS (M+H$^+$): 348.0919, found 348.0908.

9-((2,3-Dihydrobenzo[b][1,4]dioxin-6-yl)(methyl)amino)thiazolo[5,4-f]quinazoline-2-carbonitrile IXc

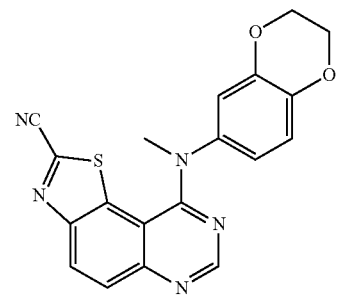 [SMILES: CN(c1ccc2c(c1)OCCO2)c1ncnc2ccc3nc(C#N)sc3c12]

Prepared from carbonitrile VIIIha. Flash chromatography eluent (EtOAc). Yield: 30%; orange solid; mp>260° C.; IR (KBr) $v_{max}$/cm$^{-1}$ 3422, 2932, 2875, 2220, 1612, 1547, 1487, 1455, 1360, 1299, 1253, 1201, 1149, 1065, 914, 877, 811; $^1$H NMR (300 MHz, DMSO-d$_6$) δ 8.54 (d, 1H, J=9.0 Hz), 8.28 (s, 1H), 7.84 (d, 1H, J=9.0 Hz), 7.12 (d, 1H, J=2.4 Hz), 6.98 (dd, 1H, J$_1$=2.4 Hz, J$_2$=8.7 Hz), 6.82 (d, 1H, J=8.7 Hz), 4.24 (s, 4H), 3.76 (s, 3H); HRMS calcd for C$_{18}$H$_{14}$N$_5$OS (M+H$^+$): 348.0919, found 348.0908.

Methods for the Synthesis of 2-substituted thiazolo-[5,4-f]quinazolines

1) General Procedure for the Preparation of Amidines 1 to 34

A stirred mixture of carbonitrile (1 mmol) and appropriate amine (1.2 mmol) in dry THF (7 mL) under argon was stirred overnight at room temperature. The solvent was removed in vacuo and the crude residue purified by flash chromatography to afford the amidines 1 to 36.

9-(3-Chloro-4-fluorophenylamino)-N-(2-morpholinoethyl)thiazolo[5,4-f]quinazoline-2-carboximidamide 1

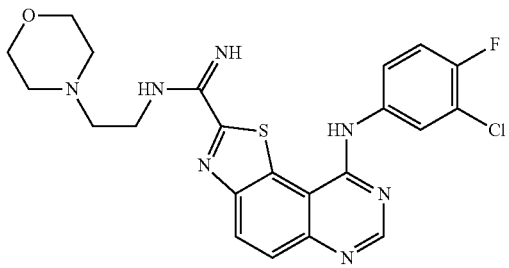 [SMILES: N=C(NCCN1CCOCC1)c1nc2ccc3ncnc(Nc4ccc(F)c(Cl)c4)c3c2s1]

Prepared from carbonitrile VIIIaa and N-aminoethylmorpholine. Flash chromatography eluent (DCM-MeOH, 5:5). Yield: 71%; yellow solid; mp 158° C.; IR (KBr) $v_{max}$/cm$^{-1}$ 2956, 2816, 1797, 1614, 1561, 1485, 1256, 1199, 1113, 1069, 966, 916, 816; $^{19}$F NMR (282 MHz, DMSO-d$_6$) δ −119.1; $^1$H NMR (300 MHz, DMSO-d$_6$) δ 8.87 (s, 1H, NH), 8.43 (d, 1H, J=7.2 Hz), 8.03 (m, 1H), 7.90 (m, 1H), 7.52 (m, 1H), 7.39 (m, 1H), 7.18 (m, 1H), 3.78-3.75 (m, 4H), 3.52 (m, 2H), 2.76-2.72 (m, 2H), 2.60 (m, 4H); HRMS calcd for $C_{22}H_{22}N_7OSClF$ (M+H$^+$): 486.1279, found 486.1292.

9-(3-Chloro-4-fluorophenylamino)-N-(2-(piperidin-1-yl)ethyl)thiazolo[5,4-f]quinazoline-2-carboximidamide 2

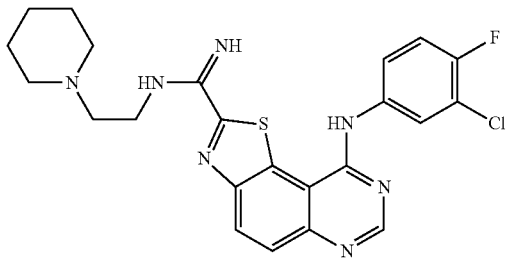 [SMILES: N=C(NCCN1CCCCC1)c1nc2ccc3ncnc(Nc4ccc(F)c(Cl)c4)c3c2s1]

Prepared from carbonitrile VIIIaa and N-aminoethylpiperidine. Flash chromatography eluent (DCM-MeOH, 3:7). Yield: 82%; orange solid; mp 147° C.; IR (KBr) $v_{max}$/cm$^{-1}$ 2928, 2361, 1572, 1483, 1380, 1255, 1201, 1121, 1086, 1051, 964, 879, 818; $^{19}$F NMR (282 MHz, CDCl$_3$) δ −123.8; $^1$H NMR (300 MHz, CDCl$_3$) δ 8.62 (s, 1H), 8.35 (d, 1H, J=9.0 Hz), 7.90 (d, 1H, J=9.0 Hz), 7.70 (m, 1H), 7.32 (m, 1H), 7.12 (t, 1H, J=9.0 Hz), 3.50 (m, 2H), 2.63 (t, 2H, J=5.7 Hz), 2.49 (m, 4H), 1.63-1.58 (m, 4H), 1.48 (m, 2H); HRMS calcd for $C_{23}H_{24}N7SClF$ (M+H$^+$): 484.1486, found 484.1501.

9-(3-Chloro-4-fluorophenylamino)-N-(2-(pyrrolidin-1-yl)ethyl)thiazolo[5,4-f]quinazoline-2-carboximidamide 3

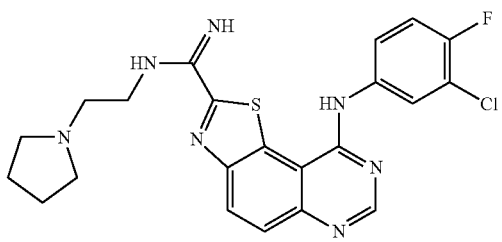 [SMILES: N=C(NCCN1CCCC1)c1nc2ccc3ncnc(Nc4ccc(F)c(Cl)c4)c3c2s1]

Prepared from carbonitrile VIIIaa and N-aminoethylpyrrolidine. Flash chromatography eluent (DCM-MeOH, 5:5). Yield: 69%; orange solid; mp 166° C.; IR (KBr) $v_{max}$/cm$^{-1}$ 3381, 3146, 2965, 2803, 1641, 1617, 1562, 1486, 1383, 1341, 1253, 1200, 1127, 1050, 965, 876, 816; $^{19}$F NMR (282 MHz, MeOD-d$_4$) δ −125.6; $^1$H NMR (300 MHz, MeOD-d$_4$) δ 8.22 (d, 1H, J=9.0 Hz), 7.95 (s, 1H), 7.59 (d, 1H, J=9.0 Hz), 7.31 (m, 1H), 7.18 (t, 1H, J=9.0 Hz), 7.15-7.12 (m, 1H), 3.45 (m, 2H), 2.85 (m, 2H), 2.67 (m, 4H), 1.83 (m, 4H); HRMS calcd for $C_{22}H_{22}N7SClF$ (M+H$^+$): 470.1330, found 470.1340.

9-(3-Chloro-4-fluorophenylamino)-N-(2-(dimethylamino)ethyl)thiazolo[5,4-f]quinazoline-2-carboximidamide 4

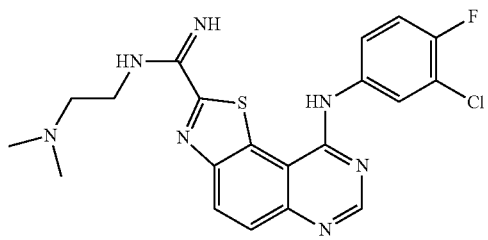 [SMILES: CN(C)CCNC(=N)c1nc2ccc3ncnc(Nc4ccc(F)c(Cl)c4)c3c2s1]

Prepared from carbonitrile VIIIaa and 2-dimethylaminoethylamine. Flash chromatography eluent (DCM-MeOH, 5:5). Yield: 50%; pale yellow solid; mp 173° C.; IR (KBr) $v_{max}$/cm$^{-1}$ 3224, 3038, 2950, 2861, 2824, 2773, 1618, 1560, 1488, 1386, 1323, 1254, 1195, 1127, 1086, 1052, 967, 816; $^{19}$F NMR (282 MHz, MeOD-d$_4$) δ −125.5; $^1$H NMR (300 MHz, MeOD-d$_4$) δ 8.34 (d, 1H, J=9.0 Hz), 7.93 (s, 1H), 7.67 (d, 1H, J=9.0 Hz), 7.29 (m, 1H), 7.18 (t, 1H, J=9.0 Hz), 7.10-7.06 (m, 1H), 3.64 (t, 2H, J=6.0 Hz), 3.27 (t, 2H, J=6.0 Hz), 2.80 (s, 6H); HRMS calcd for $C_{20}H_{20}N7SClF$ (M+H$^+$): 444.1173, found 444.1155.

9-(3-Chloro-4-fluorophenylamino)-N-(2-(diethylamino)ethyl)thiazolo[5,4-f]quinazoline-2-carboximidamide 5

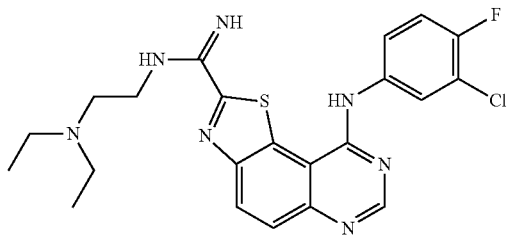 [SMILES: CCN(CC)CCNC(=N)c1nc2ccc3ncnc(Nc4ccc(F)c(Cl)c4)c3c2s1]

Prepared from carbonitrile VIIIaa and diethylethylenediamine. Flash chromatography eluent (DCM-MeOH, 5:5). Yield: 50%; orange solid; mp 140° C.; IR (KBr) $v_{max}$/cm$^{-1}$ 3295, 2969, 2812, 1671, 1618, 1560, 1489, 1386, 1346, 1254, 1196, 1127, 1052, 966, 817; $^{19}$F NMR (282 MHz, MeOD-d$_4$) δ −125.3; $^1$H NMR (300 MHz, MeOD-d$_4$) δ 8.29 (d, 1H, J=9.0 Hz), 7.94 (s, 1H), 7.63 (d, 1H, J=9.0 Hz), 7.29-7.20 (m, 2H), 7.09 (m, 1H), 3.60-3.56 (m, 2H), 2.90-2.83 (m, 2H), 2.77-2.74 (m, 4H), 1.17-1.06 (m, 6H); HRMS calcd for C$_{22}$H$_{24}$N$_7$SClF (M+H$^+$): 472.1486, found 472.1502.

N-Benzyl-9-(3-chloro-4-fluorophenylamino)thiazolo[5,4-f]quinazoline-2-carboximidamide 6

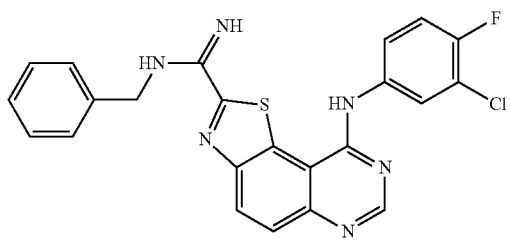 [SMILES: N=C(NCc1ccccc1)c1nc2ccc3ncnc(Nc4ccc(F)c(Cl)c4)c3c2s1]

Prepared from carbonitrile VIIIaa and benzylamine. Flash chromatography eluent (DCM-EtOAc, 2:8). Yield: 69%; yellow solid; mp 232° C.; IR (KBr) $v_{max}$/cm$^{-1}$ 3057, 1725, 1639, 1490, 1377, 1341, 1252, 1202, 1151, 1121, 1086, 1050, 965, 818; $^{19}$F NMR (282 MHz, MeOD-d$_4$) δ −125.3; $^1$H NMR (300 MHz, MeOD-d$_4$) δ 8.29 (d, 1H, J=9.0 Hz), 7.94 (s, 1H), 7.63 (d, 1H, J=9.0 Hz), 7.43 (m, 2H), 7.35-7.17 (m, 5H), 7.10 (m, 1H), 4.53 (s, 2H); HRMS calcd for C$_{23}$H$_{17}$N$_6$SClF (M+H$^+$): 463.0908, found 463.0916.

9-(3-Chloro-4-fluorophenylamino)-N,N-dimethylthiazolo[5,4-f]quinazoline-2-carboximidamide 7

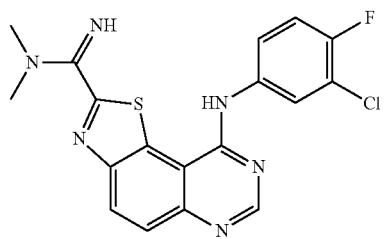 [SMILES: CN(C)C(=N)c1nc2ccc3ncnc(Nc4ccc(F)c(Cl)c4)c3c2s1]

Prepared from carbonitrile VIIIaa and dimethylamine. Flash chromatography eluent (DCM-MeOH, 5:5). Yield: 43%; yellow solid; mp>260° C.; IR (KBr) $v_{max}$/cm$^{-1}$ 3411, 3051, 1663, 1623, 1559, 1488, 1383, 1254, 1202, 1150, 1051, 966, 819; $^{19}$F NMR (282 MHz, MeOD-d$_4$) δ −125.9; $^1$H NMR (300 MHz, MeOD-d$_4$) δ 8.45 (d, 1H, J=9.0 Hz), 7.98 (s, 1H), 7.75 (d, 1H, J=9.0 Hz), 7.30-7.21 (m, 2H), 7.12 (t, 1H, J=9.0 Hz), 3.39 (s, 6H); HRMS calcd for C$_{18}$H$_{15}$N$_6$SClF (M+H$^+$): 401.0751, found 401.0742.

9-(4-Bromo-2-fluorophenylamino)-N-(2-morpholinoethyl)thiazolo[5,4-f]quinazoline-2-carboximidamide 8

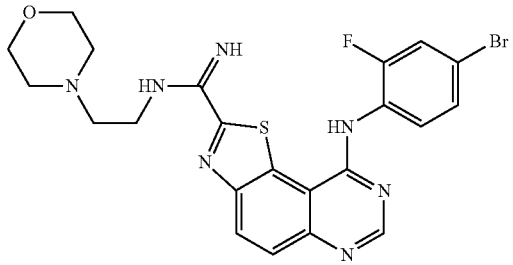 [SMILES: N=C(NCCN1CCOCC1)c1nc2ccc3ncnc(Nc4ccc(Br)cc4F)c3c2s1]

Prepared from carbonitrile VIIIba and N-aminoethylmorpholine. Flash chromatography eluent (DCM-MeOH, 5:5). Yield: 85%; yellow solid; mp 190° C.; IR (KBr) $v_{max}$/cm$^{-1}$ 3374, 2975, 2361, 1645, 1585, 1381, 1265, 1227, 1090, 1053, 973, 916, 882, 825; $^{19}$F NMR (282 MHz, DMSO-d$_6$) δ −120.0; $^1$H NMR (300 MHz, DMSO-d$_6$) δ 8.52 (d, 1H, J=9.0 Hz), 8.26 (m, 1H), 7.78 (m, 1H), 7.57 (m, 1H), 7.36 (m, 1H), 7.16 (m, 1H), 3.66 (t, 4H, J=4.5 Hz), 3.48-3.42 (m, 2H), 2.69 (t, 2H, J=6.0 Hz), 2.61 (m, 4H); HRMS calcd for C$_{22}$H$_{22}$N$_7$OSBrF (M+H$^+$): 530.0774, found 530.0782.

9-(4-Bromo-2-fluorophenylamino)-N-(2-(piperidin-1-yl)ethyl)thiazolo[5,4-f]quinazoline-2-carboximidamide 9

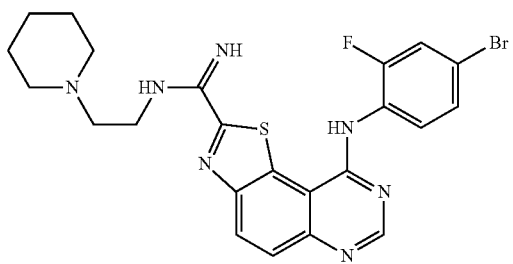 [SMILES: N=C(NCCN1CCCCC1)c1nc2ccc3ncnc(Nc4ccc(Br)cc4F)c3c2s1]

Prepared from carbonitrile VIIIba and N-aminoethylpiperidine. Flash chromatography eluent (DCM-MeOH, 5:5). Yield: 72%; yellow solid; mp 143° C.; IR (KBr) $v_{max}$/cm$^{-1}$ 3340, 2975, 2930, 2361, 1615, 1561, 1476, 1380, 1348, 1262, 1197, 1153, 1114, 1052, 881, 821; $^{19}$F NMR (282 MHz, CDCl$_3$) δ −123.8; $^1$H NMR (300 MHz, CDCl$_3$) δ 8.25

(d, 1H, J=9.0 Hz), 8.09 (s, 1H), 7.55 (d, 1H, J=9.0 Hz), 7.50-7.45 (m, 1H), 7.29 (t, 1H, J=9.0 Hz), 7.12-7.06 (m, 1H), 3.54 (m, 2H), 2.67 (t, 2H, J=5.7 Hz), 2.54 (m, 4H), 1.66-1.60 (m, 4H), 1.49 (m, 2H); HRMS calcd for $C_{23}H_{24}N_7SBrF$ (M+H$^+$): 528.0981, found 528.0986.

9-(4-Bromo-2-fluorophenylamino)-N-(2-(dimethylamino)ethyl)thiazolo[5,4-f]quinazoline-2-carboximidamide 10

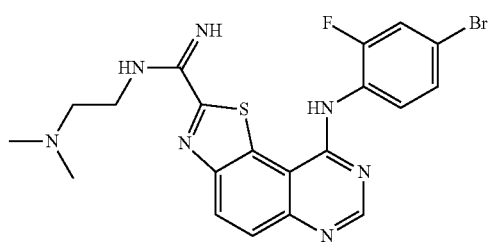 [SMILES: CN(C)CCNC(=N)c1nc2ccc3ncnc(Nc4ccc(Br)cc4F)c3c2s1]

Prepared from carbonitrile VIIIba and 2-dimethylaminoethylamine. Flash chromatography eluent (DCM-MeOH, 5:5). Yield: 64%; orange solid; mp 128° C.; IR (KBr) $v_{max}$/cm$^{-1}$ 3274, 3058, 2940, 2861, 2822, 2773, 1618, 1560, 1478, 1380, 1341, 1262, 1197, 1155, 1112, 1038, 965, 881, 823; $^{19}$F NMR (282 MHz, MeOD-d$_4$) δ −122.3; $^1$H NMR (300 MHz, MeOD-d$_4$) δ 8.33 (d, 1H, J=9.0 Hz), 7.92 (s, 1H), 7.68 (d, 1H, J=9.0 Hz), 7.41-7.36 (m, 2H), 7.15 (t, 1H, J=9.0 Hz), 3.46 (t, 2H, J=6.6 Hz), 2.76 (t, 2H, J=6.6 Hz), 2.37 (s, 6H); HRMS calcd for $C_{20}H_{20}N_7SBrF$ (M+H$^+$): 488.0668, found 488.0688.

9-(4-Bromo-2-fluorophenylamino)-N-(2-(diethylamino)ethyl)thiazolo[5,4-f]quinazoline-2-carboximidamide 11

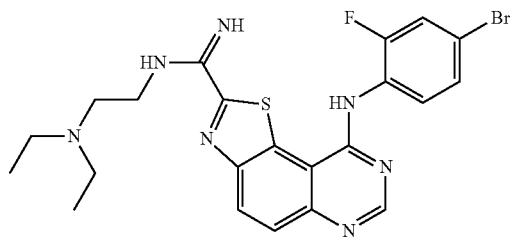 [SMILES: CCN(CC)CCNC(=N)c1nc2ccc3ncnc(Nc4ccc(Br)cc4F)c3c2s1]

Prepared from carbonitrile VIIIba and diethylethylenediamine. Flash chromatography eluent (DCM-MeOH, 5:5). Yield: 86%; orange solid; mp 88° C.; IR (KBr) $v_{max}$/cm$^{-1}$ 2965, 2360, 1793, 1619, 1520, 1477, 1378, 1265, 1198, 1067, 966, 880, 822; $^{19}$F NMR (282 MHz, MeOD-d$_4$) δ −122.1; $^1$H NMR (300 MHz, MeOD-d$_4$) δ 8.30 (d, 1H, J=9.0 Hz), 7.93 (s, 1H), 7.66 (d, 1H, J=9.0 Hz), 7.38-7.33 (m, 2H), 7.13 (t, 1H, J=9.0 Hz), 3.58 (t, 2H, J=6.6 Hz), 2.82 (t, 2H, J=6.6 Hz), 2.68 (m, 4H), 1.09 (m, 6H); HRMS calcd for $C_{22}H_{24}N_7SBrF$ (M+H$^+$): 516.0981, found 516.0988.

9-(4-Bromo-2-fluorophenylamino)-N-(2-(pyrrolidin-1-yl)ethyl)thiazolo[5,4-f]quinazoline-2-carboximidamide 12

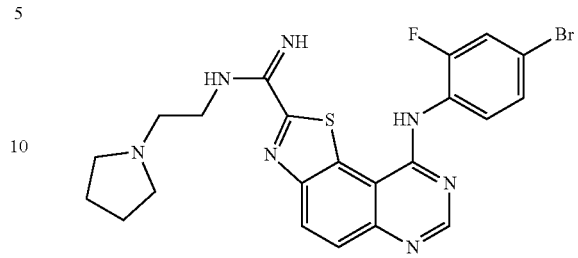

Prepared from carbonitrile VIIIba and N-aminoethylpyrrolidine. Flash chromatography eluent (DCM-MeOH, 5:5). Yield: 68%; orange solid; mp 139° C.; IR (KBr) $v_{max}$/cm$^{-1}$ 2968, 2361, 1563, 1476, 1380, 1262, 1223, 1067, 965, 880, 822; $^{19}$F NMR (282 MHz, MeOD-d$_4$) δ −123.6; $^1$H NMR (300 MHz, MeOD-d$_4$) δ 8.29 (d, 1H, J=9.0 Hz), 7.89 (s, 1H), 7.63 (d, 1H, J=9.0 Hz), 7.35-7.29 (m, 2H), 7.09 (t, 1H, J=9.0 Hz), 3.46 (t, 2H, J=6.6 Hz), 2.87 (t, 2H, J=6.6 Hz), 2.69 (m, 4H), 1.89 (m, 4H); HRMS calcd for $C_{22}H_{22}N_7SBrF$ (M+H$^+$): 514.0825, found 514.0825.

N-Benzyl-9-(4-bromo-2-fluorophenylamino)thiazolo[5,4-f]quinazoline-2-carboximidamide 13

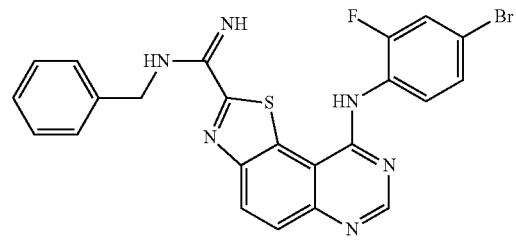 [SMILES: N=C(NCc1ccccc1)c1nc2ccc3ncnc(Nc4ccc(Br)cc4F)c3c2s1]

Prepared from carbonitrile VIIIba and benzylamine. Flash chromatography eluent (DCM-EtOAc, 2:8). Yield: 68%; yellow solid; mp 130° C.; IR (KBr) $v_{max}$/cm$^{-1}$ 2964, 2903, 2360, 1815, 1614, 1477, 1379, 1262, 1153, 1113, 1069, 966, 880, 821; $^{19}$F NMR (282 MHz, MeOD-d$_4$) δ −122.2; $^1$H NMR (300 MHz, MeOD-d$_4$) δ 8.35 (d, 1H, J=9.0 Hz), 7.92 (s, 1H), 7.69 (d, 1H, J=9.0 Hz), 7.43 (m, 3H), 7.39-7.30 (m, 3H), 7.25 (m, 1H), 7.15 (t, 1H, J=9.0 Hz), 4.53 (s, 2H); HRMS calcd for $C_{23}H_{17}N_6SBrF$ (M+H$^+$): 507.0403, found 507.0412.

9-(4-Bromo-2-fluorophenylamino)-N-(2-(dimethylamino)ethyl)thiazolo[5,4-f]quinazoline-2-carboximidamide 14

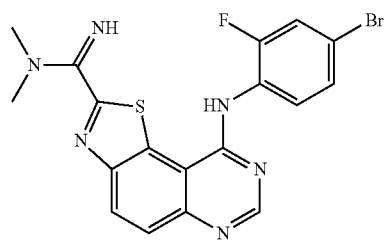 [SMILES: CN(C)C(=N)c1nc2ccc3ncnc(Nc4ccc(Br)cc4F)c3c2s1]

Prepared from carbonitrile VIIIba and dimethylamine. Flash chromatography eluent (DCM-MeOH, 5:5). Yield: 40%; orange solid; mp 222° C.; IR (KBr) $v_{max}$/cm$^{-1}$ 3270, 3154, 3061, 2923, 1634, 1584, 1519, 1492, 1410, 1346, 1291, 1226, 1201, 1152, 1116, 1049, 964, 881, 863, 831; $^{19}$F NMR (282 MHz, MeOD-d$_4$) δ −121.6; $^1$H NMR (300 MHz, MeOD-d$_4$) δ 8.18 (d, 1H, J=9.0 Hz), 7.87 (s, 1H), 7.53 (d, 1H, J=9.0 Hz), 7.28-7.19 (m, 2H), 7.12 (t, 1H, J=9.0 Hz), 3.11 (s, 6H); HRMS calcd for C$_1$H$_{15}$N$_6$SBrF (M+H$^+$): 445.0246, found 445.0264.

9-(4-Bromo-2-fluorophenylamino)-N-isopropylthiazolo[5,4-f]quinazoline-2-carboximidamide 15

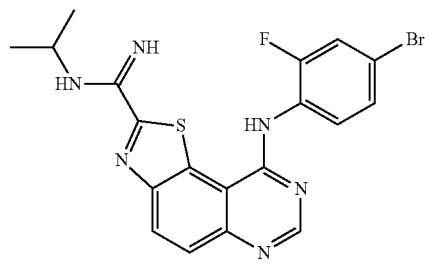 [SMILES: CC(C)NC(=N)c1nc2ccc3ncnc(Nc4ccc(Br)cc4F)c3c2s1]

Prepared from carbonitrile VIIIba and isopropylamine. Flash chromatography eluent (DCM-MeOH, 5:5). Yield: 60%; pale yellow solid; mp>260° C.; IR (KBr) $v_{max}$/cm$^{-1}$ 3326, 3144, 2962, 2864, 2460, 1643, 1585, 1530, 1498, 1482, 1406, 1384, 1351, 1306, 1258, 1226, 1173, 1150, 1121, 1062, 967, 880, 824; $^{19}$F NMR (282 MHz, MeOD-d$_4$) δ −122.3; $^1$H NMR (300 MHz, MeOD-d$_4$) δ 8.44 (d, 1H, J=9.0 Hz), 7.97 (s, 1H), 7.76 (d, 1H, J=9.0 Hz), 7.43-7.34 (m, 2H), 7.13 (t, 1H, J=9.0 Hz), 3.64 (s, 1H), 1.35 (s, 6H); HRMS calcd for C$_{19}$H$_{17}$N$_6$SBrF (M+H$^+$): 459.0403, found 459.0382.

9-(4-Bromo-2-fluorophenylamino)-N-(4-fluorobenzyl)thiazolo[5,4-f]quinazoline-2-carboximidamide 16

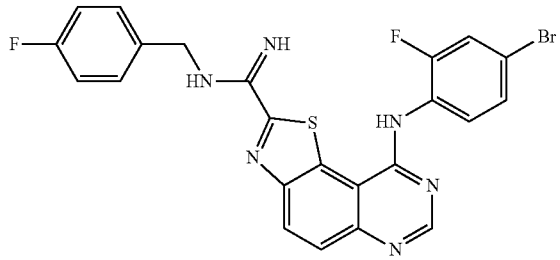 [SMILES: N=C(NCc1ccc(F)cc1)c1nc2ccc3ncnc(Nc4ccc(Br)cc4F)c3c2s1]

Prepared from carbonitrile VIIIba and 4-fluorobenzylamine. Flash chromatography eluent (DCM-EtOAc, 2:8). Yield: 28%; pale yellow solid; mp 150-160° C.; IR (KBr) $v_{max}$/cm$^{-1}$ 3403, 3165, 2853, 1617, 1596, 1570, 1509, 1478, 1413, 1382, 1350, 1300, 1262, 1224, 1181, 1152, 1112, 1085, 962, 879, 815; $^{19}$F NMR (282 MHz, MeOD-d$_4$) δ −118.5, −122.8; $^1$H NMR (300 MHz, MeOD-d$_4$) δ 8.36 (d, 1H, J=9.0 Hz), 7.92 (s, 1H), 7.69 (d, 1H, J=9.0 Hz), 7.46-7.31 (m, 4H), 7.15-7.02 (m, 3H), 4.50 (s, 2H); HRMS calcd for C$_{23}$H$_{16}$N$_6$SBrF$_2$ (M+H$^+$): 525.0309, found 525.0303.

9-(4-Bromo-2-fluorophenylamino)-N-(3-fluorobenzyl)thiazolo[5,4-f]quinazoline-2-carboximidamide 17

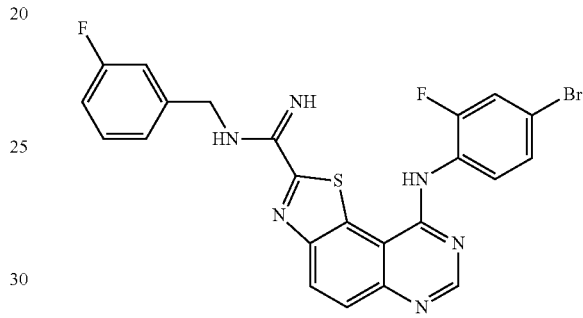

Prepared from carbonitrile VIIIba and 3-fluorobenzylamine. Flash chromatography eluent (DCM-EtOAc, 2:8). Yield: 24%; orange solid; mp 168° C.; IR (KBr) $v_{max}$/cm$^{-1}$ 3165, 3050, 2926, 2853, 2355, 1618, 1594, 1523, 1479, 1446, 1409, 1382, 1350, 1306, 1263, 1185, 1113, 1088, 1067, 962, 879, 834, 811; $^{19}$F NMR (282 MHz, MeOD-d$_4$) δ −115.6, −122.2; $^1$H NMR (300 MHz, MeOD-d$_4$) δ 8.37 (d, 1H, J=9.0 Hz), 7.92 (s, 1H), 7.68 (d, 1H, J=9.0 Hz), 7.41-7.31 (m, 3H), 7.25 (m, 1H), 7.19-7.11 (m, 2H), 6.96 (t, 1H, J=9.0 Hz), 4.52 (s, 2H); HRMS calcd for C$_{23}$H$_{16}$N$_6$SBrF$_2$ (M+H$^+$): 525.0309, found 525.0317.

9-(4-Bromo-2-fluorophenylamino)-N-(cyclohexylmethyl)thiazolo[5,4-f]quinazoline-2-carboximidamide 18

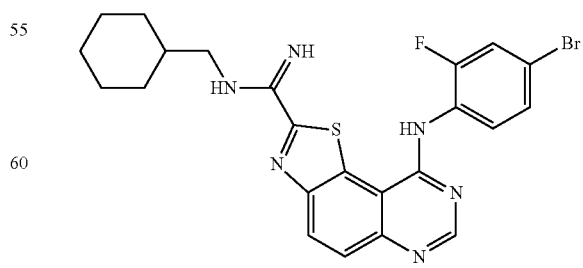

Prepared from carbonitrile VIIIba and cyclohexanemethylamine. Flash chromatography eluent (DCM-EtOAc, 2:8).

Yield: 60%; yellow solid; mp 226° C.; IR (KBr) $v_{max}$/cm$^{-1}$ 2922, 2848, 2519, 1643, 1598, 1529, 1501, 1477, 1447, 1414, 1383, 1350, 1307, 1258, 1198, 1158, 1123, 1062, 1005, 966, 879, 835, 822; $^{19}$F NMR (282 MHz, MeOD-d$_4$) δ −122.1; $^1$H NMR (300 MHz, MeOD-d$_4$) δ 8.44 (d, 1H, J=9.0 Hz), 7.97 (s, 1H), 7.76 (d, 1H, J=9.0 Hz), 7.43-7.34 (m, 2H), 7.13 (t, 1H, J=9.0 Hz), 4.50 (s, 2H), 3.15 (m, 2H), 2.01 (m, 1H), 1.89-1.85 (m, 4H), 1.26-1.23 (m, 4H); HRMS calcd for C$_{23}$H$_{23}$N$_6$SBrF (M+H$^+$): 513.0872, found 513.0896.

9-(4-Bromo-2-fluorophenylamino)-N-(pyridin-4-ylmethyl)thiazolo[5,4-f]quinazoline-2-carboximidamide 19

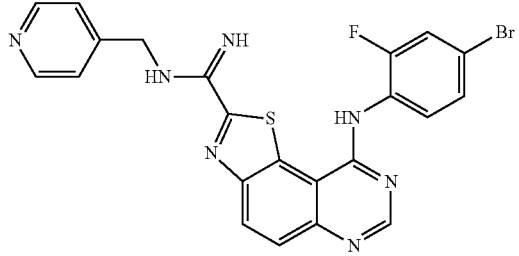 [SMILES: N=C(NCc1ccncc1)c1nc2ccc3ncnc(Nc4ccc(Br)cc4F)c3c2s1]

Prepared from carbonitrile VIIIba and 4-picolylamine. Flash chromatography eluent (DCM-MeOH, 5:5). Yield: 17%; pale yellow solid; mp>260° C.; IR (KBr) $v_{max}$/cm$^{-1}$ 3165, 3050, 2925, 2843, 1644, 1607, 1503, 1479, 1418, 1382, 1311, 1263, 1224, 1199, 1154, 1112, 1063, 1002, 965, 881, 826; $^{19}$F NMR (282 MHz, MeOD-d$_4$) δ −123.8; $^1$H NMR (300 MHz, MeOD-d$_4$) δ 8.47 (d, 1H, J=9.0 Hz), 8.31 (s, 1H), 7.91 (d, 1H, J=9.0 Hz), 7.65 (m, 1H), 7.51 (m, 2H), 7.39-7.29 (m, 3H), 7.17 (t, 1H, J=9.0 Hz), 4.57 (s, 2H); HRMS calcd for C$_{22}$H$_{16}$N7SBrF (M+H$^+$): 508.0355, found 508.0361.

9-(3-Cyanophenylamino)-N-(2-morpholinoethyl)thiazolo[5,4-f]quinazoline-2-carboximidamide 20

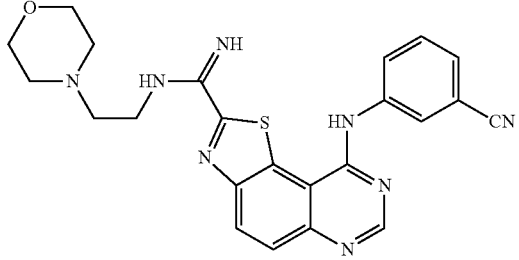 [SMILES: N#Cc1cccc(Nc2ncnc3ccc4nc(C(=N)NCCN5CCOCC5)sc4c23)c1]

Prepared from carbonitrile VIIIca and N-aminoethylmorpholine. Flash chromatography eluent (DCM-MeOH, 3:7). Yield: 56%; yellow solid; mp 183° C.; IR (KBr) $v_{max}$/cm$^{-1}$ 3051, 2922, 2234, 1646, 1572, 1307, 1262, 1140, 1072, 971, 915; $^1$H NMR (300 MHz, CDCl$_3$) δ 8.26 (d, 1H, J=9.0 Hz), 8.01 (d, 1H, J=9.0 Hz), 7.74-7.71 (m, 2H), 7.64-7.54 (m, 2H), 7.47-7.44 (m, 1H), 3.76 (t, 4H, J=4.5 Hz), 3.52-3.48 (m, 2H), 2.73 (t, 2H, J=6.0 Hz), 2.60 (m, 4H); HRMS calcd for C$_{23}$H$_{23}$N$_8$OS (M+H$^+$): 459.1716, found 459.1713.

9-(3-Cyanophenylamino)-N-(2-(piperidin-1-yl)ethyl)thiazolo[5,4-f]quinazoline-2-carboximidamide 21

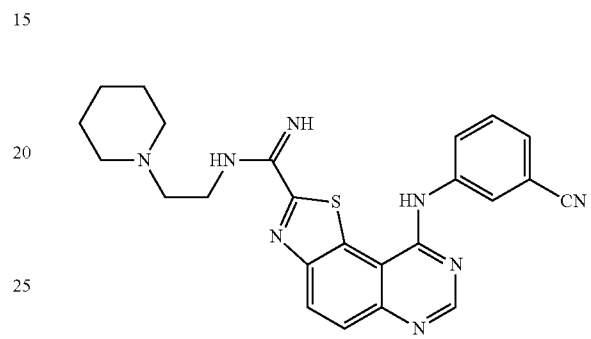

Prepared from carbonitrile VIIIca and N-aminoethylpiperidine. Flash chromatography eluent (DCM-MeOH, 3:7). Yield: 38%; yellow solid; mp 159° C.; IR (KBr) $v_{max}$/cm$^{-1}$ 2923, 2853, 2360, 2226, 1550, 1472, 1378, 1259, 1228, 1074, 966; $^1$H NMR (300 MHz, CDCl$_3$) δ 8.44 (d, 1H, J=9.0 Hz), 8.01 (d, 1H, J=9.0 Hz), 7.74-7.71 (m, 2H), 7.64-7.54 (m, 2H), 7.47-7.44 (m, 1H), 3.54 (m, 2H), 2.67 (t, 2H, J=5.7 Hz), 2.54 (m, 4H), 1.66-1.60 (m, 4H), 1.49 (m, 2H); HRMS calcd for C$_{24}$H$_{25}$N$_8$S (M+H$^+$): 457.1923, found 457.1933.

N-(2-(Dimethylamino)ethyl)-9-(4-methoxyphenylamino)thiazolo[5,4-f]quinazoline-2-carboximidamide 22

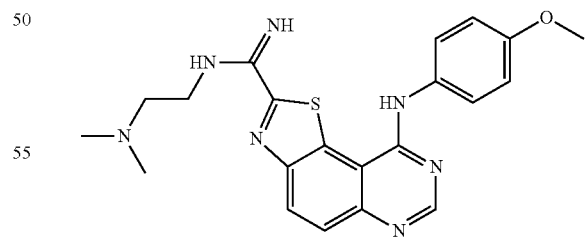

Prepared from carbonitrile VIIIda and 2-dimethylaminoethylamine. Flash chromatography eluent (DCM-MeOH, 5:5). Yield: 53%; yellow solid; mp 154° C.; IR (KBr) $v_{max}$/cm$^{-1}$ 2945, 2827, 2773, 1643, 1614, 1572, 1505, 1464, 1379, 1341, 1237, 1177, 1033, 962, 832; $^1$H NMR (300 MHz, MeOD-d$_4$) δ 8.30 (d, 1H, J=9.0 Hz), 8.06 (s, 1H), 7.69

(d, 1H, J=9.0 Hz), 7.22 (d, 2H, J=9.0 Hz), 6.97 (d, 2H, J=9.0 Hz), 3.81 (s, 3H), 3.43 (t, 2H, J=7.0 Hz), 2.70 (t, 2H, J=7.0 Hz), 2.34 (s, 6H); HRMS calcd for $C_{21}H_{24}N_7OS$ (M+H$^+$): 422.1763, found 422.1766.

N-(2-(Diethylamino)ethyl)-9-(4-methoxyphenylamino)thiazolo[5,4-f]quinazoline-2-carboximidamide 23

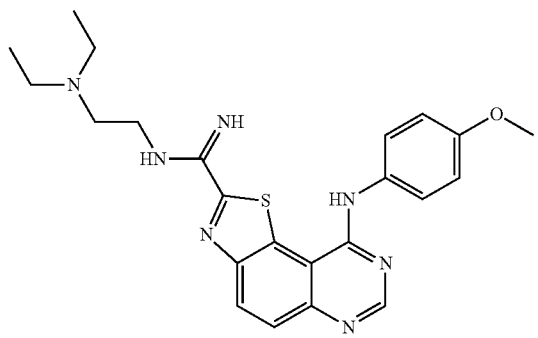 [SMILES: CCN(CC)CCNC(=N)c1nc2ccc3ncnc(Nc4ccc(OC)cc4)c3c2s1]

Prepared from carbonitrile VIIIda and diethylethylenediamine. Flash chromatography eluent (DCM-MeOH, 5:5). Yield: 50%; yellow solid; mp 103° C.; IR (KBr) $v_{max}$/cm$^{-1}$ 2967, 2832, 1641, 1614, 1572, 1507, 1378, 1341, 1285, 1237, 1178, 1086, 1034, 962, 834; $^1$H NMR (300 MHz, MeOD-d$_4$) δ 8.35 (d, 1H, J=9.0 Hz), 8.08 (s, 1H), 7.74 (d, 1H, J=9.0 Hz), 7.23 (d, 2H, J=9.0 Hz), 7.01 (d, 2H, J=9.0 Hz), 3.82 (s, 3H), 3.43 (t, 2H, J=7.0 Hz), 2.86 (t, 2H, J=7.0 Hz), 2.71 (q, 4H, J=7.0 Hz), 1.11 (t, 6H, J=7.0 Hz); HRMS calcd for $C_{23}H_{28}N_7OS$ (M+H$^+$): 450.2076, found 450.2058.

9-(4-Methoxyphenylamino)-N-(2-(pyrrolidin-1-yl)ethyl)thiazolo[5,4-f]quinazoline-2-carboximidamide 24

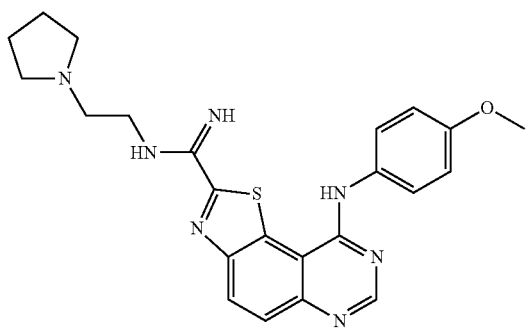 [SMILES: COc1ccc(Nc2ncnc3ccc4nc(C(=N)NCCN5CCCC5)sc4c23)cc1]

Prepared from carbonitrile VIIda and N-aminoethylpyrrolidine. Flash chromatography eluent (DCM-MeOH, 5:5). Yield: 47%; orange solid; mp 134° C.; IR (KBr) $v_{max}$/cm$^{-1}$ 2957, 2798, 1643, 1615, 1573, 1504, 1379, 1341, 1284, 1237, 1147, 1086, 1033, 962, 880, 833; $^1$H NMR (300 MHz, MeOD-d$_4$) δ 8.34 (d, 1H, J=9.0 Hz), 8.08 (s, 1H), 7.73 (d, 1H, J=9.0 Hz), 7.23 (d, 2H, J=9.0 Hz), 6.99 (d, 2H, J=9.0 Hz), 3.82 (s, 3H), 3.49 (t, 2H, J=7.0 Hz), 2.88 (t, 2H, J=7.0 Hz), 2.67 (m, 4H), 1.85 (m, 4H); HRMS calcd for $C_{23}H_{26}N_7OS$ (M+H$^+$): 448.1920, found 448.1926.

N-benzyl-9-(4-methoxyphenylamino)thiazolo[5,4-f]quinazoline-2-carboximidamide 25

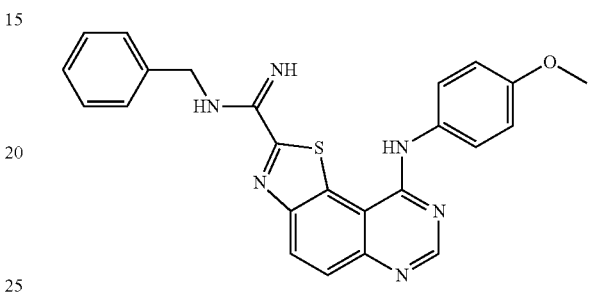

Prepared from carbonitrile VIIIda and benzylamine. Flash chromatography eluent (DCM-EtOAc, 2:8). Yield: 28%; yellow solid; mp 130° C.; IR (KBr) $v_{max}$/cm$^{-1}$ 3362, 3028, 2832, 1640, 1598, 1572, 1509, 1377, 1356, 1299, 1238, 1177, 1084, 1030, 962, 833; $^1$H NMR (300 MHz, MeOD-d$_4$) δ 8.34 (d, 1H, J=9.0 Hz), 8.08 (s, 1H), 7.73 (d, 1H, J=9.0 Hz), 7.35 (m, 4H), 7.26 (m, 3H), 6.99 (d, 2H, J=9.0 Hz), 4.55 (s, 2H), 3.83 (s, 3H); HRMS calcd for $C_{24}H_{21}N_6OS$ (M+H$^+$): 441.1498, found 441.1507.

9-(4-Methoxyphenylamino)-N-(2-morpholinoethyl)thiazolo[5,4-f]quinazoline-2-carboximidamide 26

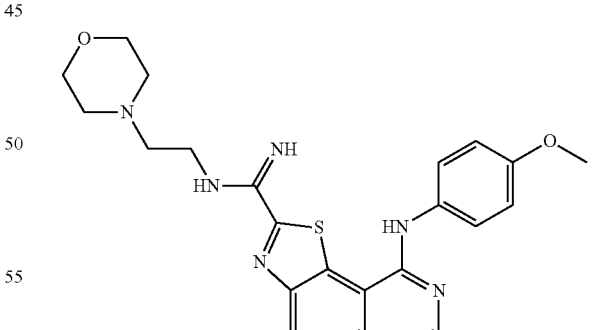

Prepared from carbonitrile VIIIda and N-aminoethylmorpholine. Flash chromatography eluent (DCM-MeOH, 5:5). Yield: 41%; yellow solid; mp 131° C.; IR (KBr) $v_{max}$/cm$^{-1}$ 3362, 3175, 2920, 2852, 1643, 1567, 1504, 1469, 1386, 1234, 1111, 1032, 964, 836; $^1$H NMR (300 MHz, MeOD-d$_4$) δ 8.37 (d, 1H, J=9.0 Hz), 8.11 (s, 1H), 7.75 (d, 1H, J=9.0

Hz), 7.26 (d, 2H, J=9.0 Hz), 7.01 (d, 2H, J=9.0 Hz), 3.82 (s, 3H), 3.73 (m, 4H), 3.48 (t, 2H, J=7.0 Hz), 2.76 (t, 2H, J=7.0 Hz), 2.62 (m, 4H); HRMS calcd for $C_{23}H_{26}N_7O_2S$ (M+H$^+$): 464.1869, found 464.1874.

9-(4-Methoxyphenylamino)-N-(2-(piperidin-1-yl)ethyl)thiazolo[5,4-f]quinazoline-2-carboximidamide 27

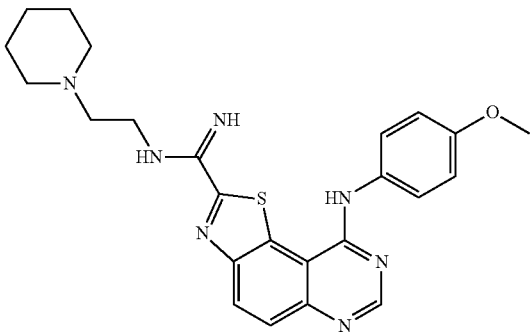 [SMILES: COc1ccc(Nc2ncnc3ccc4nc(C(=N)NCCN5CCCCC5)sc4c23)cc1]

Prepared from carbonitrile VIIIda and N-aminoethylpiperidine. Flash chromatography eluent (DCM-MeOH, 3:7). Yield: 43%; yellow solid; mp 132° C.; IR (KBr) $v_{max}$/cm$^{-1}$ 2933, 2852, 1640, 1613, 1572, 1507, 1376, 1349, 1302, 1283, 1237, 1155, 1124, 1035, 962, 833; $^1$H NMR (300 MHz, MeOD-d$_4$) δ 8.34 (d, 1H, J=9.0 Hz), 8.08 (s, 1H), 7.73 (d, 1H, J=9.0 Hz), 7.23 (d, 2H, J=9.0 Hz), 6.99 (d, 2H, J=9.0 Hz), 3.82 (s, 3H), 3.49 (t, 2H, J=7.0 Hz), 2.73 (t, 2H, J=7.0 Hz), 2.56 (m, 4H), 1.66 (m, 4H), 1.52 (m, 2H); HRMS calcd for $C_{24}H_{28}N_7OS$ (M+H$^+$): 462.2076, found 462.2098.

9-(4-Methoxyphenylamino)-N,N-dimethylthiazolo[5,4-f]quinazoline-2-carboximidamide 28

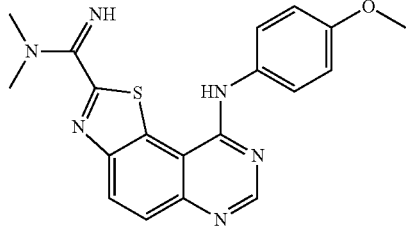

Prepared from carbonitrile VIIIda and dimethylamine. Flash chromatography eluent (DCM-MeOH, 5:5). Yield: 67%; pale yellow solid; mp 152° C.; IR (KBr) $v_{max}$/cm$^{-1}$ 3139, 2924, 1681, 1644, 1571, 1509, 1383, 1347, 1286, 1237, 1176, 1031, 966, 834; $^1$H NMR (300 MHz, MeOD-d$_4$) δ 8.15 (d, 1H, J=9.0 Hz), 7.84 (s, 1H), 7.53 (d, 1H, J=9.0 Hz), 7.08 (d, 2H, J=9.0 Hz), 6.89 (d, 2H, J=9.0 Hz), 3.77 (s, 3H), 3.13 (s, 6H); HRMS calcd for $C_{19}H_{19}N_6OS$ (M+H$^+$): 379.1341, found 379.1333.

9-(Benzo[d][1,3]dioxol-5-ylamino)-N-(2-morpholinoethyl)thiazolo[5,4-f]quinazoline-2-carboximidamide 29

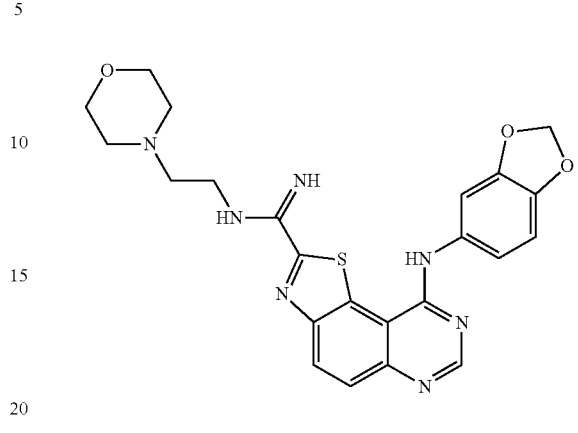

Prepared from carbonitrile VIIIfa and N-aminoethylmorpholine. Flash chromatography eluent (DCM-MeOH, 5:5). Yield: 41%; yellow solid; mp 169° C.; IR (KBr) $v_{max}$/cm$^{-1}$ 3324, 2965, 2901, 2861, 2812, 1641, 1616, 1587, 1503, 1468, 1382, 1353, 1304, 1271, 1232, 1180, 1148, 1114, 1067, 1036, 969, 935, 839; $^1$H NMR (300 MHz, MeOD-d$_4$) 88.33 (d, 1H, J=9 Hz), 7.96 (s, 1H), 7.71 (d, 1H, J=9 Hz), 6.87 (d, 1H, J=9 Hz), 6.74 (s, 1H), 6.64 (d, 1H, J=9 Hz), 5.96 (s, 2H), 3.74 (m, 4H), 3.55 (t, 2H, J=7 Hz), 2.75 (t, 2H, J=7 Hz), 2.61 (m, 4H); HRMS calcd for $C_{23}H_{24}N_7O_3S$ (M+H$^+$): 478.1661, found 478.1649.

9-(Benzo[d][1,3]dioxol-5-ylamino)-N-(2-(piperidin-1-yl)ethyl)thiazolo[5,4-f]quinazoline-2-carboximidamide 30

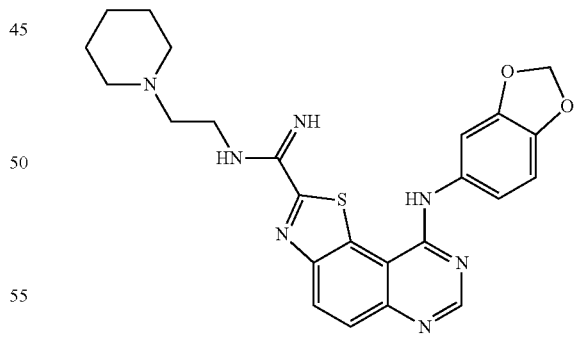

Prepared from carbonitrile VIIIfa and N-aminoethylpiperidine. Flash chromatography eluent (DCM-MeOH, 3:7). Yield: 34%; yellow solid; mp 170° C.; IR (KBr) $v_{max}$/cm$^{-1}$ 3350, 2936, 2773, 2482, 2061, 1641, 1613, 1585, 1503, 1462, 1374, 1337, 1304, 1229, 1176, 1141, 1121, 1037, 983, 962, 931, 855, 832; $^1$H NMR (300 MHz, MeOD-d$_4$) δ 8.33 (d, 1H, J=9 Hz), 7.89 (s, 1H), 7.69 (d, 1H, J=9 Hz), 6.86 (d, 1H, J=9 Hz), 6.75 (s, 1H), 6.63 (d, 1H, J=9 Hz), 5.99 (s, 2H), 3.46 (t, 2H, J=7 Hz), 2.71 (t, 2H, J=7 Hz), 2.57 (m, 4H), 1.64 (m, 4H), 1.50 (m, 2H); HRMS calcd for $C_{24}H_{26}N_7O_2S$ (M+H$^+$): 476.1869, found 476.1883.

9-(Benzo[d][1,3]dioxol-5-ylamino)-N-(2-(pyrrolidin-1-yl)ethyl)thiazolo[5,4-f]quinazoline-2-carboximidamide 31

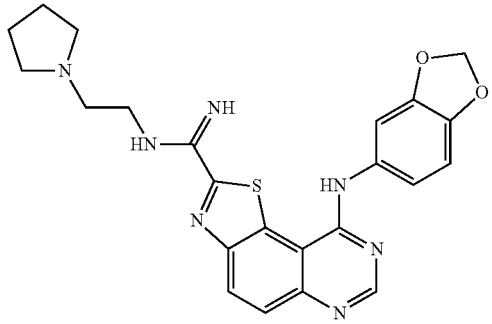 [SMILES: N=C(NCCN1CCCC1)c1nc2ccc3ncnc(Nc4ccc5c(c4)OCO5)c3c2s1]

Prepared from carbonitrile VIIIfa and N-aminoethylpyrrolidine. Flash chromatography eluent (DCM-MeOH, 5:5). Yield: 48%; yellow solid; mp 172° C.; IR (KBr) $v_{max}$/cm$^{-1}$ 2906, 2803, 1643, 1614, 1573, 1500, 1467, 1377, 1347, 1305, 1265, 1228, 1175, 1121, 1036, 966, 933, 833; $^1$H NMR (300 MHz, MeOD-d$_4$) δ 8.27 (d, 1H, J=9 Hz), 7.90 (s, 1H), 7.65 (d, 1H, J=9 Hz), 6.86 (d, 1H, J=9 Hz), 6.75 (s, 1H), 6.63 (d, 1H, J=9 Hz), 5.97 (s, 2H), 3.46 (t, 2H, J=7 Hz), 2.85 (t, 2H, J=7 Hz), 2.67 (m, 4H), 1.83 (m, 4H); HRMS calcd for $C_{23}H_{24}N_7O_2S$ (M+H$^+$): 462.1712, found 462.1736.

9-(Benzo[d][1,3]dioxol-5-ylamino)-N-benzylthiazolo[5,4-f]quinazoline-2-carboximidamide 32

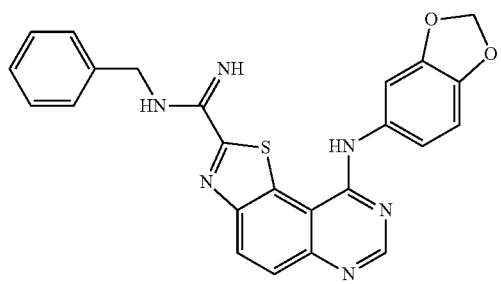 [SMILES: N=C(NCc1ccccc1)c1nc2ccc3ncnc(Nc4ccc5c(c4)OCO5)c3c2s1]

Prepared from carbonitrile VIIIfa and benzylamine. Flash chromatography eluent (DCM-EtOAc, 2:8). Yield: 21%; yellow solid; mp>260° C.; IR (KBr) $v_{max}$/cm$^{-1}$ 2886, 2447, 1641, 1597, 1497, 1466, 1413, 1384, 1353, 1307, 1266, 1229, 1178, 1122, 1105, 1036, 967, 934, 861, 833; $^1$H NMR (300 MHz, MeOD-d$_4$) δ 8.27 (d, 1H, J=9 Hz), 7.90 (s, 1H), 7.65 (d, 1H, J=9 Hz), 6.86 (m, 4H), 6.75 (m, 3H), 6.63 (d, 1H, J=9 Hz), 5.97 (s, 2H), 4.58 (s, 2H); HRMS calcd for $C_{24}H_{19}N_6O_2S$ (M+H$^+$): 455.1290, found 455.1287.

9-(Benzo[d][1,3]dioxol-5-ylamino)-N-(2-(dimethylamino)ethyl)thiazolo[5,4-f]quinazoline-2-carboximidamide 33

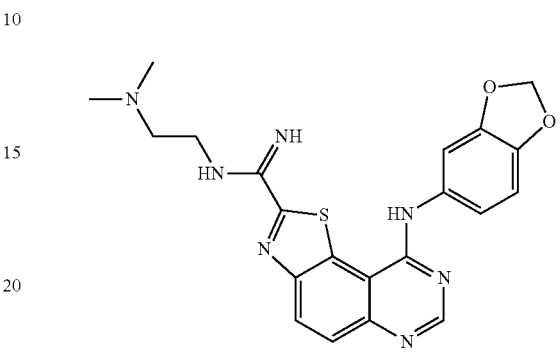

Prepared from carbonitrile VIIIfa and 2-dimethylaminoethylamine. Flash chromatography eluent (DCM-MeOH, 5:5). Yield: 10%; yellow solid; mp>260° C.; IR (KBr) $v_{max}$/cm$^{-1}$ 3391, 2923, 2852, 1643, 1615, 1538, 1498, 1467, 1383, 1346, 1302, 1263, 1229, 1178, 1118, 1035, 965, 933, 856, 835; $^1$H NMR (300 MHz, MeOD-d$_4$) δ 8.17 (d, 1H, J=9 Hz), 7.90 (s, 1H), 7.56 (d, 1H, J=9 Hz), 6.86 (d, 1H, J=9 Hz), 6.75 (s, 1H), 6.63 (d, 1H, J=9 Hz), 5.91 (s, 2H), 3.43 (t, 2H, J=7 Hz), 2.69 (t, 2H, J=7 Hz), 2.33 (s, 6H); HRMS calcd for $C_{21}H_{22}N_7O_2S$ (M+H$^+$): 436.1556, found 436.1549.

9-(Benzo[d][1,3]dioxol-5-ylamino)-N-(2-(diethylamino)ethyl)thiazolo[5,4-f]quinazoline-2-carboximidamide 34

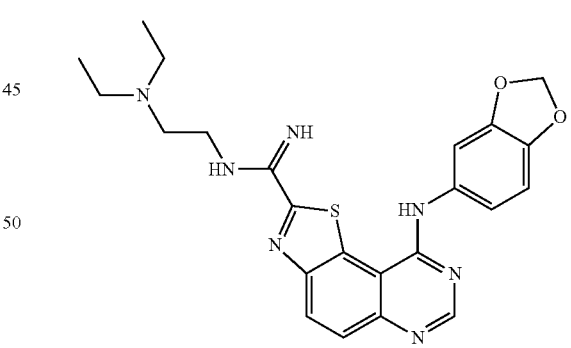

Prepared from carbonitrile VIIIfa and diethylethylenediamine. Flash chromatography eluent (DCM-MeOH, 5:5). Yield: 66%; yellow solid; mp 144° C.; IR (KBr) $v_{max}$/cm$^{-1}$ 3333, 2970, 2920, 2832, 1641, 1614, 1585, 1502, 1463, 1421, 1378, 1348, 1303, 1231, 1179, 1145, 1122, 1088, 1037, 965, 933, 858, 831; $^1$H NMR (300 MHz, MeOD-d$_4$) δ 8.23 (d, 1H, J=9 Hz), 7.89 (s, 1H), 7.62 (d, 1H, J=9 Hz), 6.86 (d, 1H, J=9 Hz), 6.75 (s, 1H), 6.63 (d, 1H, J=9 Hz), 5.94 (s, 2H), 3.42 (t, 2H, J=7 Hz), 2.83 (t, 2H, J=7 Hz), 2.68 (q, 4H, J=7 Hz), 1.10 (t, 6H, J=7 Hz); HRMS calcd for $C_{23}H_{26}N_7O_2S$ (M+H$^+$): 464.1869, found 464.1896.

2) General Procedure for the Synthesis of Amides 35 to 40

A stirred mixture of carbonitrile (0.13 mmol) and NaOH (2.5 N sol., 50 μL) in butanol (2.5 mL) was irradiated under microwaves at 117° C. for 30 min. The solvent was removed in vacuo and the crude residue purified by flash chromatography to afford the amides 37 to 43.

9-(3-Chloro-4-fluorophenylamino)thiazolo[5,4-f]quinazoline-2-carboxamide 35

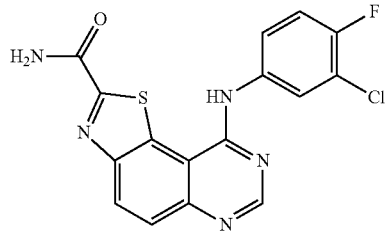 [SMILES: NC(=O)c1nc2ccc3ncnc(Nc4ccc(F)c(Cl)c4)c3c2s1]

Prepared from carbonitrile VIIIaa. Flash chromatography eluent (DCM-EtOAc, 5:5). Yield: 98%; orange solid; mp>260° C.; IR (KBr) $v_{max}$/cm$^{-1}$ 3453, 1684, 1624, 1601, 1576, 1534, 1506, 1487, 1376, 1348, 1282, 1260, 1209, 1124, 1085, 1057, 993, 969, 825, 810; $^{19}$F NMR (282 MHz, DMSO-d$_6$) δ −129.1; $^1$H NMR (300 MHz, DMSO-d$_6$) δ 8.26-8.21 (m, 2H), 8.12 (d, 1H, J=9.0 Hz), 8.02-7.99 (m, 1H), 7.80 (s, 1H), 7.53 (d, 1H, J=9.0 Hz), 7.47 (m, 1H), 7.18 (t, 1H, J=9.0 Hz); HRMS calcd for C$_{16}$H$_{10}$N$_5$OSClF (M+H$^+$): 374.0279, found 374.0280.

9-(4-Bromo-2-fluorophenylamino)thiazolo[5,4-f]quinazoline-2-carboxamide 36

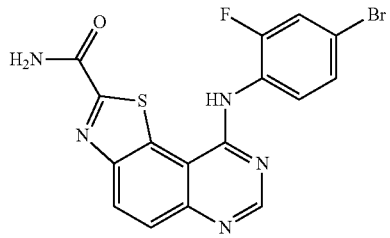 [SMILES: NC(=O)c1nc2ccc3ncnc(Nc4ccc(Br)cc4F)c3c2s1]

Prepared from carbonitrile VIIIba. Flash chromatography eluent (DCM-EtOAc, 5:5). Yield: 71%; yellow solid; mp>260° C.; IR (KBr) $v_{max}$/cm$^{-1}$ 1682, 1645, 1615, 1575, 1557, 1486, 1347, 1254, 1200, 1158, 1118, 1074, 993, 967, 941, 865, 819; $^{19}$F NMR (282 MHz, DMSO-d$_6$) δ −120.5; $^1$H NMR (300 MHz, DMSO-d$_6$) δ 8.47 (s, 1H), 8.41 (d, 1H, J=9.0 Hz), 8.39 (s, 1H), 8.14 (s, 1H), 8.03 (d, 1H, J=9.0 Hz), 7.53 (m, 1H), 7.36 (m, 1H), 7.21 (t, 1H, J=9.0 Hz); HRMS calcd for C$_{16}$H$_{10}$N$_5$OSBrF (M+H$^+$): 417.9769, found 417.9769.

9-(4-Methoxyphenylamino)thiazolo[5,4-f]quinazoline-2-carboxamide 37

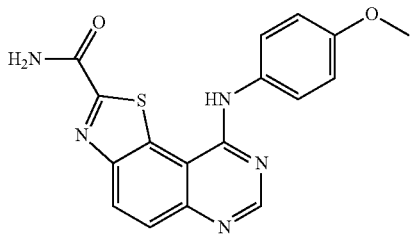 [SMILES: COc1ccc(Nc2ncnc3ccc4nc(C(N)=O)sc4c23)cc1]

Prepared from carbonitrile VIIIda. Flash chromatography eluent (DCM-EtOAc, 5:5). Yield: 98%; orange solid; mp 213° C.; IR (KBr) $v_{max}$/cm$^{-1}$ 3409, 1691, 1638, 1600, 1572, 1509, 1431, 1380, 1349, 1325, 1301, 1237, 1177, 1123, 1085, 1032, 964, 835, 814; $^1$H NMR (300 MHz, DMSO-d$_6$) δ 8.37 (s, 1H), 8.24 (d, 1H, J=9.0 Hz), 8.06 (s, 1H), 7.92 (s, 1H), 7.61 (d, 1H, J=9.0 Hz), 7.31 (d, 2H, J=9.0 Hz), 6.89 (d, 2H, J=9.0 Hz), 3.74 (s, 3H); HRMS calcd for C$_{17}$H$_{14}$N$_5$O$_2$S (M+H$^+$): 352.0868, found 352.0879.

9-(3,4,5-Trimethoxyphenylamino)thiazolo[5,4-f]quinazoline-2-carboxamide 38

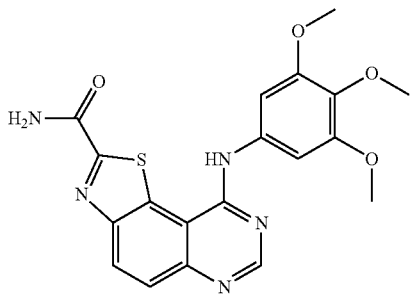 [SMILES: COc1cc(Nc2ncnc3ccc4nc(C(N)=O)sc4c23)cc(OC)c1OC]

Prepared from carbonitrile VIIIea. Flash chromatography eluent (DCM-EtOAc, 5:5). Yield: 98%; orange solid; mp 202° C.; IR (KBr) $v_{max}$/cm$^{-1}$ 3466, 2938, 1692, 1641, 1582, 1503, 1413, 1352, 1306, 1225, 1123, 1003, 952, 826; $^1$H NMR (300 MHz, MeOD-d$_4$) δ 8.17 (d, 1H, J=9.0 Hz), 7.99 (s, 1H), 7.56 (d, 1H, J=9.0 Hz), 6.59 (m, 2H), 3.85 (s, 6H), 3.76 (s, 3H); HRMS calcd for C$_{19}$H$_{18}$N$_5$O$_4$S (M+H$^+$): 412.1080, found 412.1076.

9-(Benzo[d][1,3]dioxol-5-ylamino)thiazolo[5,4-f]quinazoline-2-carboxamide 39

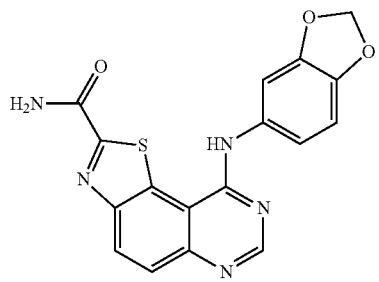 [SMILES: NC(=O)c1nc2ccc3ncnc(Nc4ccc5c(c4)OCO5)c3c2s1]

Prepared from carbonitrile VIIIfa. Flash chromatography eluent (DCM-EtOAc, 5:5). Yield: 31%; yellow solid; mp>260° C.; IR (KBr) $v_{max}$/cm$^{-1}$ 3291, 2915, 1648, 1576, 1532, 1497, 1476, 1376, 1351, 1323, 1272, 1191, 1104, 1035, 965, 923, 830, 815; $^1$H NMR (300 MHz, DMSO-d$_6$) δ 8.05-7.98 (m, 2H), 7.49 (d, 1H, J=2 Hz), 7.37-7.31 (m, 1H), 6.96 (dd, 1H, J=2 Hz, J$_2$=9 Hz), 6.73 (dd, 1H, J=2 Hz, J$_2$=9 Hz), 5.88 (s, 2H); HRMS calcd for C$_{17}$H$_{12}$N$_5$O$_3$S (M+H$^+$): 366.0661, found 366.0658.

9-(3,4-Dimethoxyphenylamino)thiazolo[5,4-f]quinazoline-2-carboxamide 40

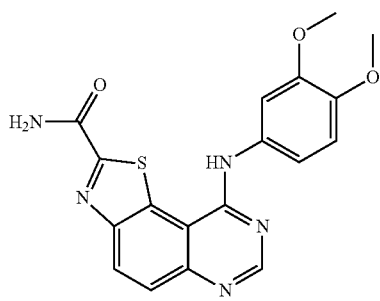 [SMILES: COc1ccc(Nc2ncnc3ccc4nc(C(N)=O)sc4c23)cc1OC]

Prepared from carbonitrile VIIIia. Flash chromatography eluent (DCM-MeOH, 9:1). Yield: 5%; yellow solid; mp>260° C.; IR (KBr) $v_{max}$/cm$^{-1}$ 3442, 3275, 2932, 2833, 1638, 1582, 1504, 1463, 1377, 1260, 1226, 1126, 1023, 966, 934, 848, 803; $^1$H NMR (300 MHz, DMSO-d$_6$) δ 8.48 (s, 1H, NH), 8.38 (d, 1H, J=9 Hz), 8.03 (m, 2H, NH$_2$), 7.72 (d, 1H, J=9 Hz), 6.99 (d, 2H, J=8.4 Hz), 6.81 (m, 2H, NH$_2$), 3.76 (s, 6H); HRMS calcd for C$_{18}$H$_{16}$N$_5$O$_3$S (M+H$^+$): 382.0974, found 382.0958.

3) Synthesis of imidazoline: N-(3-Chloro-4-fluorophenyl)-2-(4,5-dihydro-1H-imidazol-2-yl)thiazolo[5,4-f]quinazolin-9-amine 41

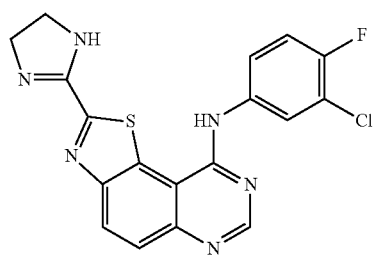 [SMILES: Fc1ccc(Nc2ncnc3ccc4nc(C5=NCCN5)sc4c23)cc1Cl]

A stirred mixture of carbonitrile VIIIaa (0.14 mmol) and ethylene diamine (5.6 mmol) in dry THF (7 mL) was irradiated under microwaves at 116° C. for 30 min. The mixture was dissolved in dichloromethane, washed with water. The organic layer was dried over MgSO$_4$, and the solvent was removed in vacuo to afford the expected compound 41 (31.1 mg, 57% yield) as a yellow solid; mp>260° C.; IR (KBr) $v_{max}$/cm$^{-1}$ 2924, 1629, 1587, 1493, 1349, 1286, 1258, 1205, 1149, 1080, 1052, 966, 883, 836, 814; $^{19}$F NMR (282 MHz, DMSO-d$_6$) δ -125.6; $^1$H NMR (300 MHz, DMSO-d$_6$) δ 8.30 (d, 1H, J=9.0 Hz), 8.15 (s, 1H), 7.62 (d, 1H, J=9.0 Hz), 7.58-7.55 (m, 1H), 7.33 (t, 1H, J=9.0 Hz), 7.36-7.21 (m, 1H) 3.69 (s, 4H); HRMS calcd for C$_{18}$H$_{13}$N6SClF (M+H$^+$): 399.0595, found 399.0602.

4) Synthesis of oxazole: 2-(4,5-dihydrooxazol-2-yl)-N-(4-methoxyphenyl)thiazolo[5,4-f]quinazolin-9-amine 42

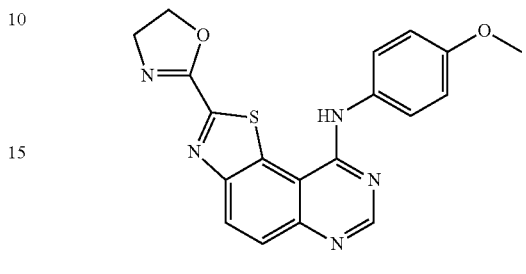

A stirred mixture of carbonitrile VIIIda (0.15 mmol) and ethanolamine (6.0 mmol) in dry THF (2 mL) was irradiated under microwaves at 170° C. for 30 min. The solvent was removed in vacuo and the crude residue was purified by flash chromatography (DCM-MeOH, 8:2) to afford the expected compound 42 (49.0 mg, 87% yield) as an orange solid; mp 162° C.; IR (KBr) $v_{max}$/cm$^{-1}$ 3150, 1639, 1617, 1571, 1500, 1376, 1236, 1166, 1030, 967, 825; $^1$H NMR (300 MHz, MeOD-d$_4$) δ 8.29 (d, 1H, J=9.0 Hz), 7.99 (s, 1H), 7.67 (d, 1H, J=9.0 Hz), 7.13 (m, 2H), 6.97 (d, 2H, J=8.4 Hz), 3.86-3.81 (m, 5H) 3.59 (t, 2H, J=5.4 Hz); HRMS calcd for C$_{19}$H$_{16}$N$_5$O$_2$S (M+H$^+$): 378.1025, found 378.1024.

5) General Procedure for the Synthesis of Imidates 43 to 80

A stirred mixture of carbonitrile (0.13 mmol) and NaOCH$_3$ (0.5 M sol. in MeOH, 130 μL) in methanol (4 mL) was irradiated under microwaves at 65° C. for 30 min. The solvent was removed in vacuo and the crude residue purified by flash chromatography to afford the imidate 43 to 80.

Methyl 9-(3-chloro-4-fluorophenylamino)thiazolo[5,4-f]quinazoline-2-carbimidate 43

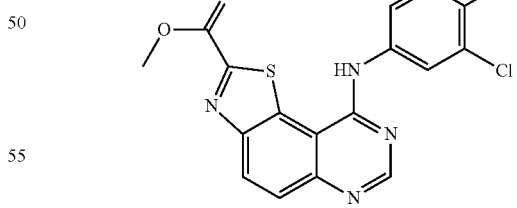

Prepared from carbonitrile VIIaa. Flash chromatography eluent (DCM-EtOAc, 5:5). Yield: 98%; orange solid; mp 212° C.; IR (KBr) $v_{max}$/cm$^{-1}$ 1642, 1559, 1479, 1352, 1260, 1201, 1156, 1073, 942, 817; $^{19}$F NMR (282 MHz, DMSO-d$_6$) δ -126.9; $^1$H NMR (300 MHz, DMSO-d$_6$) δ 8.29 (d, 1H, J=9.0 Hz), 8.18 (s, 1H), 7.73 (m, 1H), 7.61 (d, 1H, J=9.0 Hz), 7.30 (m, 1H), 7.27 (t, 1H, J=9.0 Hz), 3.95 (s, 3H); HRMS calcd for C$_{17}$H$_2$N$_5$OSClF (M+H$^+$): 388.0435, found 388.0447.

Methyl 9-(4-bromo-2-fluorophenylamino)thiazolo[5,4-f]quinazoline-2-carbimidate 44

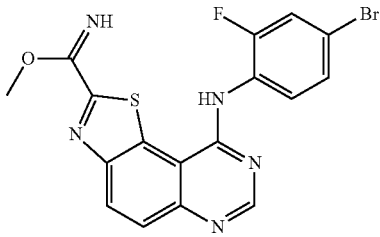 [SMILES: COC(=N)c1nc2ccc3ncnc(Nc4ccc(Br)cc4F)c3c2s1]

Prepared from carbonitrile VIIIba. Flash chromatography eluent (DCM-EtOAc, 2:8). Yield: 94%; pale yellow solid; mp>260° C.; IR (KBr) $v_{max}$/cm$^{-1}$ 2950, 1638, 1617, 1595, 1555, 1507, 1479, 1434, 1398, 1352, 1325, 1288, 1224, 1197, 1159, 1115, 1070, 988, 965, 942, 882, 818; $^{19}$F NMR (282 MHz, DMSO-d$_6$) δ −119.8; $^1$H NMR (300 MHz, DMSO-d$_6$) δ 8.46 (d, 1H, J=9.0 Hz), 8.02 (s, 1H), 7.69 (d, 1H, J=9.0 Hz), 7.53 (m, 1H), 7.35 (m, 1H), 7.20 (t, 1H, J=9.0 Hz), 3.94 (s, 3H); HRMS calcd for C$_{17}$H$_{12}$N$_5$OSBrF (M+H$^+$): 431.9930, found 431.9937.

Methyl 9-(4-methoxyphenylamino)thiazolo[5,4-f]quinazoline-2-carbimidate 45

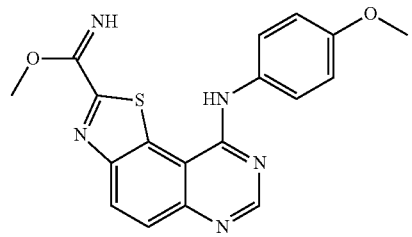

Prepared from carbonitrile VIIIda. Flash chromatography eluent (DCM-MeOH, 5:5). Yield: 82%; orange solid; mp 241° C.; IR (KBr) $v_{max}$/cm$^{-1}$ 2833, 2354, 1644, 1614, 1567, 1504, 1439, 1397, 1373, 1349, 1325, 1286, 1240, 1215, 1181, 1155, 1104, 1069, 1033, 965, 935, 859, 832, 814; $^1$H NMR (300 MHz, MeOD-d$_4$) δ 8.09 (d, 1H, J=9.0 Hz), 7.93 (s, 1H), 7.50 (d, 1H, J=9.0 Hz), 7.14 (d, 2H, J=9.0 Hz), 6.82 (d, 2H, J=9.0 Hz), 3.98 (s, 3H), 3.74 (s, 3H); HRMS calcd for C$_{18}$H$_{16}$N$_5$O$_2$S (M+H$^+$): 366.1025, found 366.1034.

Methyl 9-((4-methoxyphenyl)(methyl)amino)thiazolo[5,4-f]quinazoline-2-carbimidate 46

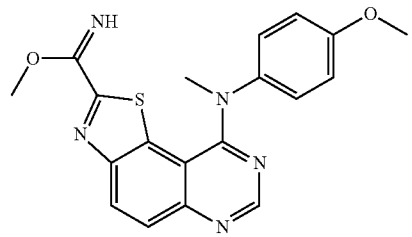

Prepared from carbonitrile IXb. Flash chromatography eluent (DCM-MeOH, 9:1). Yield: 93%; yellow solid; mp 248° C.; IR (KBr) $v_{max}$/cm$^{-1}$ 3267, 3057, 2929, 2837, 1736, 1654, 1613, 1555, 1493, 1434, 1404, 1369, 1330, 1268, 1240, 1219, 1146, 1100, 1058, 1033, 982, 939, 886, 835, 811; $^1$H NMR (300 MHz, MeOD-d$_4$) δ 8.42 (d, 1H, J=9.0 Hz), 8.18 (s, 1H), 7.71 (d, 1H, J=9.0 Hz), 7.34 (d, 2H, J=9.0 Hz), 6.91 (d, 2H, J=9.0 Hz), 3.96 (s, 3H), 3.75 (s, 3H), 3.73 (s, 3H); HRMS calcd for C$_{19}$H$_{18}$N$_5$O$_2$S (M+H$^+$): 380.1181, found 380.1179.

Methyl 9-(7-bromobenzo[d][1,3]dioxol-5-ylamino)thiazolo[5,4-f]quinazoline-2-carbimidate 47

Prepared from carbonitrile VIIIga. Flash chromatography eluent (DCM-EtOAc, 5:5). Yield: 77%; yellow solid; mp>260° C.; IR (KBr) $v_{max}$/cm$^{-1}$ 3248, 2919, 2406, 1647, 1617, 1575, 1560, 1519, 1504, 1487, 1424, 1375, 1334, 1300, 1264, 1178, 1147, 1114, 1036, 960, 925, 843; $^1$H NMR (300 MHz, DMSO-d$_6$) δ 8.44 (d, 1H, J=9.0 Hz), 8.02 (s, 1H), 7.72 (d, 1H, J=9.0 Hz), 7.26 (s, 1H), 6.77 (s, 1H), 5.06 (s, 2H), 3.94 (s, 3H); HRMS calcd for C$_{18}$H$_{13}$N$_5$O$_3$SBr (M+H$^+$): 457.9922, found 457.9937.

Methyl 9-(benzo[d][1,3]dioxol-5-ylamino)thiazolo[5,4-f]quinazoline-2-carbimidate 48

Prepared from carbonitrile VIIIha. Flash chromatography eluent (DCM-EtOAc, 5:5). Yield: 92%; yellow solid; mp 232° C.; IR (KBr) $v_{max}$/cm$^{-1}$ 3287, 2902, 1648, 1617, 1575, 1528, 1499, 1483, 1452, 1432, 1385, 1322, 1272, 1196, 1125, 1043, 936, 885, 834, 817; $^1$H NMR (300 MHz, DMSO-d$_6$) δ 8.36 (d, 1H, J=9 Hz), 7.96 (s, 1H), 7.71 (d, 1H, J=9 Hz), 6.87 (d, 1H, J=8 Hz), 6.74 (m, 1H), 6.63 (d, 1H, J=8 Hz), 5.96 (s, 2H), 4.05 (s, 3H); HRMS calcd for C$_{18}$H$_{14}$N$_5$O$_3$S (M+H$^+$): 380.0817, found 380.0805.

Methyl 9-(2,3-dihydrobenzo[b][1,4]dioxin-6-ylamino)thiazolo[5,4-f]quinazoline-2-carbimidate 49

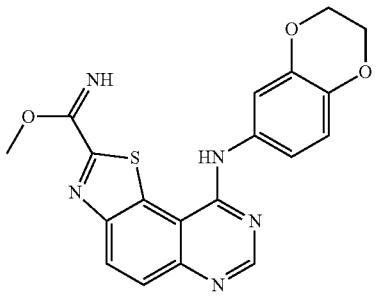 [SMILES: COC(=N)c1nc2ccc3ncnc(Nc4ccc5c(c4)OCCO5)c3c2s1]

Prepared from carbonitrile VIIIha. Flash chromatography eluent (EtOAc). Yield: 80%; yellow solid; mp 194° C.; IR (KBr) $v_{max}$/cm$^{-1}$ 3575, 3063, 1647, 1578, 1499, 1439, 1347, 1302, 1241, 1199, 1156, 1122, 1062, 948, 915, 836; $^1$H NMR (300 MHz, DMSO-d$_6$) δ 8.40 (d, 1H, J=9 Hz), 8.01 (s, 1H), 7.69 (d, 1H, J=9 Hz), 6.87 (d, 1H, J=2.1 Hz), 6.67 (m, 2H), 4.24 (s, 4H), 3.94 (s, 3H); HRMS calcd for C$_{19}$H$_{16}$N$_5$O$_3$S (M+H$^+$): 394.0974, found 394.0954.

Methyl 9-((2,3-dihydrobenzo[b][1,4]dioxin-6-yl)(methyl)amino)thiazolo[5,4-f]quinazoline-2-carbimidate 50

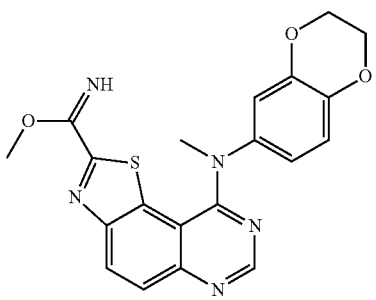 [SMILES: COC(=N)c1nc2ccc3ncnc(N(C)c4ccc5c(c4)OCCO5)c3c2s1]

Prepared from carbonitrile IXc. Flash chromatography eluent (DCM-MeOH, 9:1). Yield: 66%; yellow solid; mp>260° C.; IR (KBr) $v_{max}$/cm$^{-1}$ 3298, 2973, 2875, 1642, 1620, 1555, 1484, 1435, 1408, 1360, 1298, 1273, 1242, 1203, 1162, 1146, 1065, 939, 878, 847; $^1$H NMR (300 MHz, DMSO-d$_6$) δ 8.45 (d, 1H, J=9 Hz), 8.21 (s, 1H), 7.74 (d, 1H, J=9 Hz), 6.97 (d, 1H, J=2.1 Hz), 6.83 (m, 2H), 4.24 (s, 4H), 3.96 (s, 3H), 3.75 (s, 3H); HRMS calcd for C$_{20}$H$_{18}$N$_5$O$_3$S (M+H$^+$): 408.1130, found 408.1111.

Methyl 9-(3,4-dimethoxyphenylamino)thiazolo[5,4-f]quinazoline-2-carbimidate 51

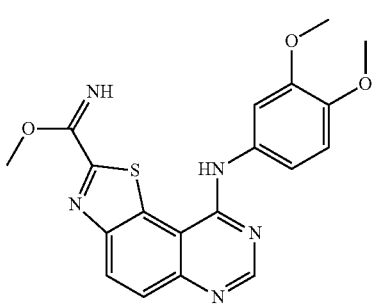

Prepared from carbonitrile VIIIia. Flash chromatography eluent (EtOAc). Yield: 89%; yellow solid; mp 218° C.; IR (KBr) $v_{max}$/cm$^{-1}$ 3289, 2921, 2852, 1651, 1613, 1583, 1505, 1466, 1432, 1376, 1348, 1309, 1261, 1226, 1195, 1164, 1146, 1128, 1075, 1027, 968, 945, 924, 854, 832; $^1$H NMR (300 MHz, DMSO-d$_6$) δ 8.44 (d, 1H, J=9 Hz), 7.92 (s, 1H), 7.72 (d, 1H, J=9 Hz), 6.99 (d, 1H, J=2.1 Hz), 6.83 (d, 1H, J=8.4 Hz), 6.75 (dd, 1H, J$_1$=2.1 Hz, J$_2$=8.4 Hz), 3.94 (s, 3H), 3.76 (s, 6H); HRMS calcd for C$_{19}$H$_{18}$N$_5$O$_3$S (M+H$^+$): 396.1130, found 396.1119.

Methyl 9-((3,4-dimethoxyphenyl)(methyl)amino)thiazolo[5,4-f]quinazoline-2-carbimidate 52

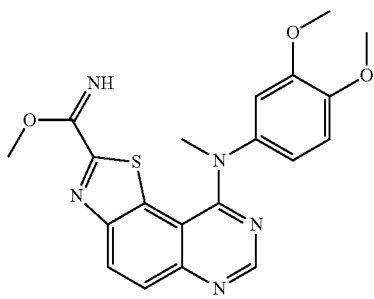

Prepared from carbonitrile IXa. Flash chromatography eluent (DCM-MeOH, 9:1). Yield: 73%; yellow solid; mp 220° C.; IR (KBr) $v_{max}$/cm$^{-1}$ 3298, 2986, 2832, 1644, 1619, 1555, 1492, 1434, 1361, 1253, 1228, 1162, 1142, 1127, 1069, 1026, 953, 927, 832, 800; $^1$H NMR (300 MHz, DMSO-d$_6$) δ 8.46 (d, 1H, J=9 Hz), 8.21 (s, 1H), 7.75 (d, 1H, J=9 Hz), 7.03 (d, 1H, J=2.1 Hz), 6.93 (d, 1H, J=8.4 Hz), 6.84 (dd, 1H, J=2.1 Hz, J$_2$=8.4 Hz), 3.96 (s, 3H), 3.75 (s, 9H); HRMS calcd for C$_{19}$H$_{18}$N$_5$O$_3$S (M+H$^+$): 396.1130, found 396.1119.

Methyl 9-(4-hydroxyphenylamino)thiazolo[5,4-f]quinazoline-2-carbimidate 53

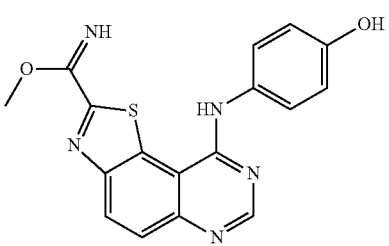

Prepared from carbonitrile VIIIja. Flash chromatography eluent (EtOAc). Yield: 81%; yellow solid; mp 196° C.; IR (KBr) $v_{max}$/cm$^{-1}$ 2953, 2852, 1644, 1619, 1573, 1508, 1477, 1372, 1326, 1235, 1164, 1100, 1077, 968, 940, 835; $^1$H NMR (300 MHz, DMSO-d$_6$) δ 8.38 (d, 1H, J=9 Hz), 8.02 (s, 1H), 7.69 (d, 1H, J=9 Hz), 7.04 (m, 2H), 6.80-6.73 (m, 2H), 3.94 (s, 3H); HRMS calcd for C$_{17}$H$_{14}$N$_5$O$_2$S (M+H$^+$): 352.0868, found 352.0873.

Methyl 9-(3-hydroxy-4-methoxyphenylamino)thiazolo[5,4-f]quinazoline-2-carbimidate 54

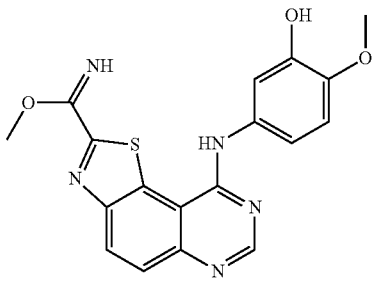

Prepared from carbonitrile VIIIka. Flash chromatography eluent (EtOAc). Quantitative yield; yellow solid; mp 216° C.; IR (KBr) $v_{max}$/cm$^{-1}$ 3289, 2921, 2852, 1643, 1611, 1578, 1505, 1441, 1379, 1348, 1281, 1245, 1154, 1128, 1077, 1027, 957, 834; $^1$H NMR (300 MHz, DMSO-d$_6$) δ 8.40 (d, 1H, J=9 Hz), 7.99 (s, 1H), 7.71 (d, 1H, J=9 Hz), 6.94 (d, 1H, J=8.4 Hz), 6.65-6.55 (m, 2H), 3.94 (s, 3H), 3.77 (s, 3H); HRMS calcd for C$_{18}$H$_{16}$N$_5$O$_3$S (M+H$^+$): 382.0974, found 382.0957.

Methyl 9-(2,3-dihydrobenzofuran-5-ylamino)thiazolo[5,4-f]quinazoline-2-carbimidate 55

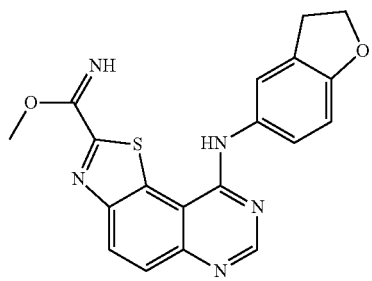 [SMILES: COC(=N)c1nc2ccc3ncnc(Nc4ccc5c(c4)CCO5)c3c2s1]

Prepared from carbonitrile VIIIa. Flash chromatography eluent (EtOAc). Yield: 66%; yellow solid; mp 202° C.; IR (KBr) $v_{max}$/cm$^{-1}$ 3291, 3053, 2911, 1641, 1611, 1573, 1508, 1482, 1437, 1355, 1333, 1287, 1226, 1196, 1158, 1092, 1067, 985, 942, 821; $^1$H NMR (300 MHz, DMSO-d$_6$) δ 8.39 (d, 1H, J=9 Hz), 8.01 (s, 1H), 7.69 (d, 1H, J=9 Hz), 7.12 (m, 1H), 6.92 (m, 1H), 6.78-6.73 (m, 1H), 4.53 (t, 2H, J=8.7 Hz), 3.95 (s, 3H), 3.19 (t, 2H, J=8.7 Hz); HRMS calcd for C$_{19}$H$_{16}$N$_5$O$_2$S (M+H$^+$): 378.1025, found 378.1006.

Methyl 9-(4-chlorophenylamino)thiazolo[5,4-f]quinazoline-2-carbimidate 56

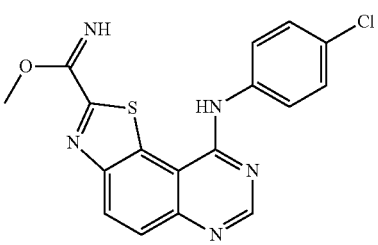 [SMILES: COC(=N)c1nc2ccc3ncnc(Nc4ccc(Cl)cc4)c3c2s1]

Prepared from carbonitrile VIIIma. Flash chromatography eluent (EtOAc). Yield: 62%; yellow solid; mp>260° C.; IR (KBr) $v_{max}$/cm$^{-1}$ 2948, 1644, 1604, 1557, 1509, 1481, 1435, 1401, 1356, 1285, 1240, 1159, 1094, 1074, 992, 943, 816; $^1$H NMR (300 MHz, DMSO-d$_6$) δ 8.42 (d, 1H, J=9 Hz), 8.08 (s, 1H), 7.70 (d, 1H, J=9 Hz), 7.41 (d, 2H, J=8.1 Hz), 7.20 (m, 2H), 3.95 (s, 3H); HRMS calcd for C$_{17}$H$_{13}$N$_5$OSCl (M+H$^+$): 370.0529, found 370.0521.

Methyl 9-(3,4-dichlorophenylamino)thiazolo[5,4-f]quinazoline-2-carbimidate 57

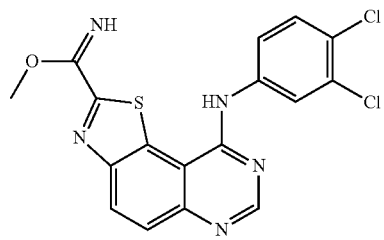

Prepared from carbonitrile VIIIna. Flash chromatography eluent (DCM-EtOAc, 5:5). Yield: 45%; yellow solid; mp 230° C.; IR (KBr) $v_{max}$/cm$^{-1}$ 3296, 2920, 1640, 1608, 1588, 1551, 1507, 1491, 1469, 1437, 1397, 1356, 1284, 1158, 1129, 1073, 1023, 942, 860, 821; $^1$H NMR (300 MHz, DMSO-d$_6$) δ 8.42 (d, 1H, J=9 Hz), 8.19 (s, 1H), 7.69 (d, 1H, J=9 Hz), 7.56 (d, 2H, J=9 Hz), 7.22 (m, 1H), 3.95 (s, 3H); HRMS calcd for C$_{17}$H$_{12}$N$_5$OSCl$_2$ (M+H$^+$): 404.0140, found 404.0135.

Methyl 9-(3-ethynylphenylamino)thiazolo[5,4-f]quinazoline-2-carbimidate 58

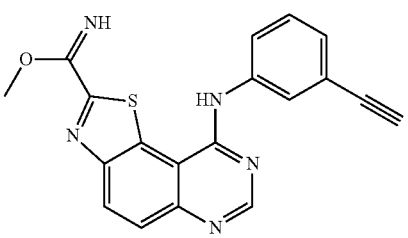 [SMILES: C#Cc1cccc(Nc2ncnc3ccc4nc(C(=N)OC)sc4c23)c1]

Prepared from carbonitrile VIIIoa. Flash chromatography eluent (EtOAc). Yield: 68%; yellow solid; mp 220° C.; yellow solid; mp 220° C.; IR (KBr) $v_{max}$/cm$^{-1}$ 3293, 2950, 1731, 1644, 1613, 1552, 1489, 1437, 1353, 1286, 1157, 1070, 968, 941, 871, 822; $^1$H NMR (300 MHz, DMSO-d$_6$) δ 8.43 (d, 1H, J=9 Hz), 8.11 (s, 1H), 7.70 (d, 1H, J=9 Hz), 7.37 (t, 1H, J=7.8 Hz), 7.26-7.16 (m, 3H), 4.16 (s, 1H), 3.95 (s, 3H); HRMS calcd for C$_{19}$H$_{14}$N$_5$OS (M+H$^+$): 360.0919, found 360.0908.

Methyl 9-(1H-benzo[d]imidazol-6-ylamino)thiazolo[5,4-f]quinazoline-2-carbimidate 59

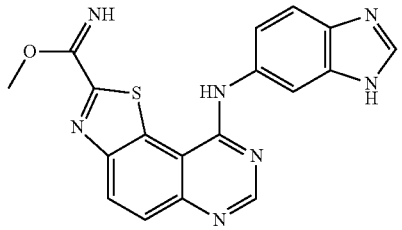 [SMILES: COC(=N)c1nc2ccc3ncnc(Nc4ccc5nc[nH]c5c4)c3c2s1]

Prepared from carbonitrile VIIIpa. Flash chromatography eluent (DCM-MeOH, 8:2). Yield: 57%; yellow solid; mp>260° C.; IR (KBr) $v_{max}$/cm$^{-1}$ 3094, 1641, 1615, 1573, 1479, 1380, 1343, 1294, 1199, 1141, 1070, 947, 824; $^1$H NMR (300 MHz, DMSO-d$_6$) δ 8.46-8.36 (m, 2H), 8.18 (m, 1H), 8.02 (d, 1H, J=9 Hz), 7.73 (d, 1H, J=8.1 Hz), 7.65 (d, 1H, J=8.1 Hz), 7.54 (m, 1H), 3.95 (s, 3H); HRMS calcd for C$_8$H$_{14}$N$_7$OS (M+H$^+$): 376.0981, found 376.0974.

Methyl 9-(4-hydroxy-3-nitrophenylamino)thiazolo[5,4-f]quinazoline-2-carbimidate 60

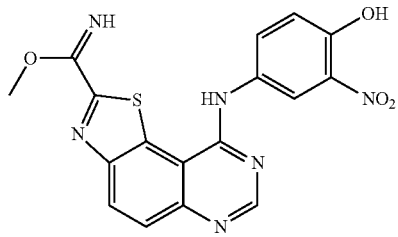 [SMILES: COC(=N)c1nc2ccc3ncnc(Nc4ccc(O)c([N+](=O)[O-])c4)c3c2s1]

Prepared from carbonitrile VIIIqa. Flash chromatography eluent (EtOAc). Yield: 34%; orange solid; mp 210° C.; IR (KBr) $v_{max}$/cm$^{-1}$ 2957, 2911, 1724, 1622, 1560, 1520, 1476, 1379, 1310, 1243, 1156, 1070, 971, 945, 820; $^1$H NMR (300 MHz, DMSO-d$_6$) δ 8.30 (d, 1H, J=8.7 Hz), 8.18 (m, 1H), 7.67 (m, 2H), 7.16 (d, 1H, J=8.7 Hz), 3.96 (s, 3H); HRMS calcd for C$_{17}$H$_{13}$N$_6$O$_4$S (M+H): 397.0719, found 397.0710.

Methyl 9-(3,4,5-trimethoxyphenylamino)thiazolo[5,4-f]quinazoline-2-carbimidate 61

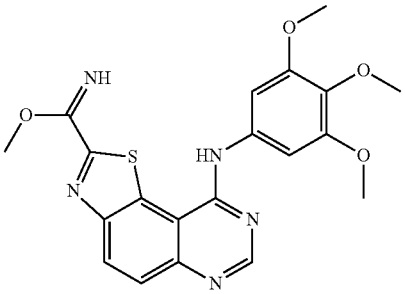

Prepared from carbonitrile VIIIea. Flash chromatography eluent (EtOAc). Yield: 87%; yellow solid; mp 254° C.; IR (KBr) $v_{max}$/cm$^{-1}$ 3291, 2941, 2833, 1640, 1583, 1496, 1434, 1415, 1337, 1228, 1164, 1143, 1116, 1073, 993, 975, 954, 861, 844, 822; $^1$H NMR (300 MHz, DMSO-d$_6$) δ 9.34 (s, 1H, NH), 8.42 (d, 1H, J=9.0 Hz), 7.94 (s, 1H), 7.74 (d, 1H, J=9.0 Hz), 6.37 (s, 2H), 3.94 (s, 3H), 3.77 (s, 6H), 3.67 (s, 3H); HRMS calcd for C$_{20}$H$_{20}$N$_5$O$_4$S (M+H$^+$): 426.1236, found 426.1240.

Methyl 9-(2,4-dimethoxyphenylamino)thiazolo[5,4-f]quinazoline-2-carbimidate 62

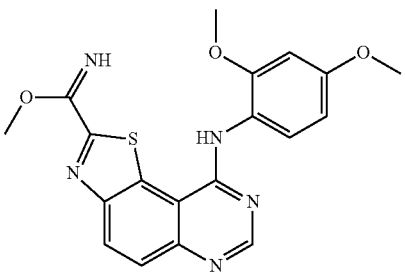

Prepared from carbonitrile VIIIra. Flash chromatography eluent (EtOAc). Yield: 71%; pale green solid; mp 245° C.; IR (KBr) $v_{max}$/cm$^{-1}$ 3380, 3277, 2999, 2942, 2828, 1654, 1608, 1566, 1545, 1526, 1506, 1455, 1431, 1332, 1276, 1204, 1152, 1123, 1097, 1063, 1026, 993, 963, 942, 916; $^1$H NMR (300 MHz, DMSO-d$_6$) δ 9.33 (s, 1H, NH), 8.41 (d, 1H, J=9.0 Hz), 7.84 (s, 1H), 7.73 (d, 1H, J=9.0 Hz), 6.88 (m, 1H), 6.68 (m, 1H), 6.58 (d, 1H, J=7.8 Hz), 3.94 (s, 3H), 3.79 (s, 3H), 3.72 (s, 3H); HRMS calcd for C$_{19}$H$_{18}$N$_5$O$_3$S (M+H$^+$): 396.1130, found 396.1124.

Methyl 9-(3,5-dimethoxyphenylamino)thiazolo[5,4-f]quinazoline-2-carbimidate 63

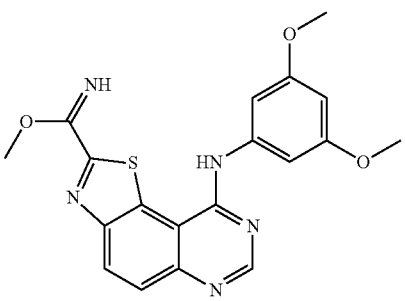

Prepared from carbonitrile VIIIsa. Flash chromatography eluent (EtOAc). Yield: 58%; pale yellow solid; mp 259° C.; IR (KBr) $v_{max}$/cm$^{-1}$ 3237, 2955, 2929, 1731, 1660, 1579, 1495, 1440, 1368, 1347, 1301, 1250, 1189, 1149, 1107, 1058, 973, 953, 856, 824; $^1$H NMR (300 MHz, DMSO-d$_6$) δ 9.34 (s, 1H, NH), 8.43 (d, 1H, J=9.0 Hz), 7.96 (s, 1H), 7.74 (d, 1H, J=9.0 Hz), 6.25 (m, 3H), 3.94 (s, 3H), 3.74 (s, 6H); HRMS calcd for C$_{19}$H$_{18}$N$_5$O$_3$S (M+H): 396.1130, found 396.1128.

Methyl 9-(phenylamino)thiazolo[5,4-f]quinazoline-2-carbimidate 64

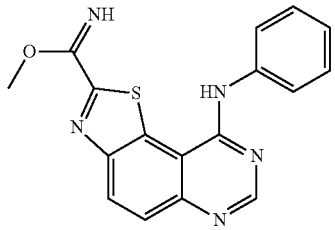 [SMILES: COC(=N)c1nc2ccc3ncnc(Nc4ccccc4)c3c2s1]

Prepared from carbonitrile VIIIta. Flash chromatography eluent (EtOAc). Yield: 52%; yellow solid; mp>260° C.; IR (KBr) $v_{max}$/cm$^{-1}$ 3294, 3147, 2950, 2877, 1727, 1640, 1609, 1570, 1552, 1507, 1480, 1434, 1351, 1284, 1210, 1153, 1067, 990, 965, 939, 869, 819; $^1$H NMR (300 MHz, DMSO-d$_6$) δ 9.32 (s, 1H, NH), 8.41 (d, 1H, J=9.0 Hz), 7.99 (s, 1H), 7.68 (d, 1H, J=9.0 Hz), 7.38 (m, 2H), 7.09 (m, 3H), 3.94 (s, 3H); HRMS calcd for $C_{17}H_{14}N_5OS$ (M+H$^+$): 336.0919, found 336.0904.

Methyl 9-(p-tolylamino)thiazolo[5,4-f]quinazoline-2-carbimidate 65

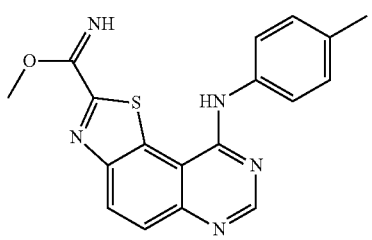

Prepared from carbonitrile VIIIua. Flash chromatography eluent (EtOAc). Yield: 88%; yellow solid; mp>260° C.; IR (KBr) $v_{max}$/cm$^{-1}$ 3292, 3148, 2848, 1725, 1641, 1600, 1557, 1488, 1434, 1351, 1283, 1155, 1068, 990, 966, 939, 820, 804; $^1$H NMR (300 MHz, DMSO-d$_6$) δ 9.33 (s, 1H, NH), 8.41 (d, 1H, J=9.0 Hz), 7.95 (s, 1H), 7.69 (d, 1H, J=9.0 Hz), 7.20 (m, 2H), 7.11 (m, 2H), 3.94 (s, 3H), 2.32 (s, 3H); HRMS calcd for $C_{18}H_{16}N_5OS$ (M+H$^+$): 350.1076, found 350.1072.

Methyl 9-(4-fluorophenylamino)thiazolo[5,4-f]quinazoline-2-carbimidate 66

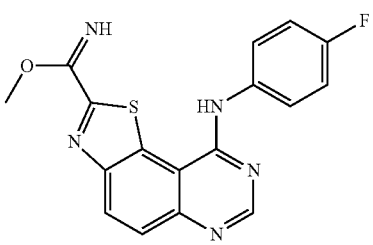 [SMILES: COC(=N)c1nc2ccc3ncnc(Nc4ccc(F)cc4)c3c2s1]

Prepared from carbonitrile VIIIva. Flash chromatography eluent (EtOAc). Yield: 77%; yellow solid; mp>260° C.; IR (KBr) $v_{max}$/cm$^{-1}$ 3416, 3298, 3226, 3150, 2950, 1731, 1641, 1611, 1574, 1558, 1506, 1490, 1434, 1400, 1355, 1329, 1285, 1226, 1157, 1103, 1072, 994, 968, 943, 819; $^{19}$F NMR (282 MHz, DMSO-d$_6$) δ −120.8; $^1$H NMR (300 MHz, DMSO-d$_6$) δ 9.33 (s, 1H, NH), 8.41 (d, 1H, J=9.0 Hz), 7.93 (s, 1H), 7.68 (d, 1H, J=9.0 Hz), 7.19 (m, 4H), 3.95 (s, 3H); HRMS calcd for $C_{17}H_{13}N_5OSF$ (M+H$^+$): 354.0825, found 354.0811.

Methyl 9-(3-cyanophenylamino)thiazolo[5,4-f]quinazoline-2-carbimidate 67

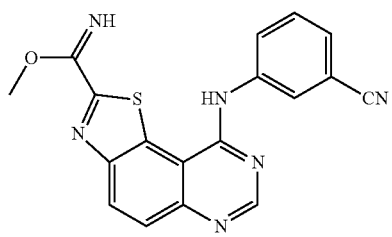 [SMILES: COC(=N)c1nc2ccc3ncnc(Nc4cccc(C#N)c4)c3c2s1]

Prepared from carbonitrile VIIIca. Flash chromatography eluent (EtOAc). Yield: 33%; pale yellow solid; mp>260° C.; IR (KBr) $v_{max/cm}^{-1}$ 3272, 2235, 1722, 1638, 1615, 1581, 1571, 1491, 1437, 1143, 1109, 1067, 989, 968, 943, 885, 840; $^1$H NMR (300 MHz, DMSO-d$_6$) δ 9.34 (s, 1H, NH), 8.45 (d, 1H, J=9.0 Hz), 8.20 (s, 1H), 7.68 (d, 1H, J=9.0 Hz), 7.61 (m, 4H), 3.95 (s, 3H); HRMS calcd for $C_{18}H_{13}N_6OS$ (M+H$^+$): 361.0872, found 361.0862.

Methyl 9-(2-bromo-4-fluorophenylamino)thiazolo[5,4-f]quinazoline-2-carbimidate 68

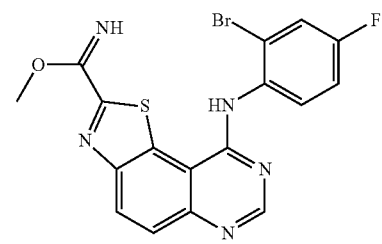 [SMILES: COC(=N)c1nc2ccc3ncnc(Nc4ccc(F)cc4Br)c3c2s1]

Prepared from carbonitrile VIIIwa. Flash chromatography eluent (EtOAc). Yield: 69%; yellow solid; mp>260° C.; IR (KBr) $v_{max}$/cm$^{-1}$ 3150, 3063, 2955, 1726, 1644, 1598, 1566, 1508, 1472, 1436, 1397, 1353, 1324, 1282, 1260, 1185, 1155, 1071, 939, 853, 812; $^{19}$F NMR (282 MHz, DMSO-d$_6$) δ −120.32; $^1$H NMR (300 MHz, DMSO-d$_6$) δ 9.34 (s, 1H, NH), 8.46 (d, 1H, J=9.0 Hz), 8.07 (s, 1H), 7.70 (d, 1H, J=9.0 Hz), 7.62 (m, 1H), 7.24 (m, 1H), 7.13 (m, 1H), 3.93 (s, 3H); HRMS calcd for $C_{17}H_2N_5OSBrF$ (M+H$^+$): 431.9930, found 431.9909.

Methyl 9-(2-fluoro-4-methoxyphenylamino)thiazolo[5,4-f]quinazoline-2-carbimidate 69

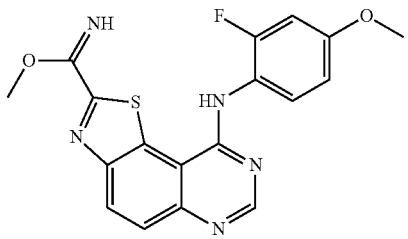

Prepared from carbonitrile VIIIxa. Flash chromatography eluent (EtOAc). Yield: 82%; yellow solid; mp 224° C.; IR (KBr) $v_{max}$/cm$^{-1}$ 3150, 2950, 1645, 1601, 1570, 1488, 1435, 1355, 1322, 1285, 1269, 1203, 1155, 1096, 1069, 1032, 939, 819; $^{19}$F NMR (282 MHz, DMSO-d$_6$) δ −120.44; $^1$H NMR (300 MHz, DMSO-d$_6$) δ 9.33 (s, 1H, NH), 8.42 (d, 1H, J=9.0 Hz), 8.06 (s, 1H), 7.70 (d, 1H, J=9.0 Hz), 7.19 (m, 1H), 6.88 (m, 1H), 6.77 (m, 1H), 3.94 (s, 3H), 3.78 (s, 3H); HRMS calcd for C$_{18}$H$_{15}$N$_5$O$_2$SF (M+H$^+$): 384.0930, found 384.0925.

Methyl 9-(4-cyanophenylamino)thiazolo[5,4-f]quinazoline-2-carbimidate 70

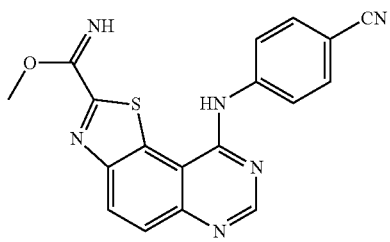

Prepared from carbonitrile VIIIya. Flash chromatography eluent (EtOAc). Yield: 52%; yellow solid; mp>260° C.; IR (KBr) $v_{max}$/cm$^{-1}$ 3264, 2215, 1655, 1625, 1591, 1561, 1493, 1435, 1385, 1335, 1272, 1227, 1146, 1069, 995, 938, 848, 815; $^1$H NMR (300 MHz, DMSO-d$_6$) δ 9.32 (s, 1H, NH), 8.43 (d, 1H, J=9.0 Hz), 8.17 (s, 1H), 7.79 (d, 2H, J=6.9 Hz), 7.68 (d, 1H, J=7.2 Hz), 7.32 (d, 2H, J=6.9 Hz), 3.94 (s, 3H); HRMS calcd for C$_{18}$H$_{13}$N$_6$OS (M+H$^+$): 361.0872, found 361.0863.

Methyl 9-(4-chloro-2-fluorophenylamino)thiazolo[5,4-f]quinazoline-2-carbimidate 71

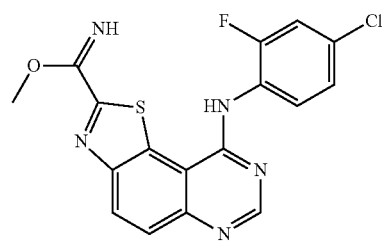 [SMILES: COC(=N)c1nc2ccc3ncnc(Nc4ccc(Cl)cc4F)c3c2s1]

Prepared from carbonitrile VIIIza. Flash chromatography eluent (EtOAc). Yield: 58%; yellow solid; mp>260° C.; IR (KBr) $v_{max}$/cm$^{-1}$ 2953, 1641, 1600, 1553, 1507, 1481, 1397, 1355, 1287, 1198, 1159, 1120, 1072, 944, 899, 818; $^{19}$F NMR (282 MHz, DMSO-d$_6$) δ −120.1; $^1$H NMR (300 MHz, DMSO-d$_6$) δ 9.34 (s, 1H, NH), 8.45 (d, 1H, J=9.0 Hz), 8.14 (s, 1H), 7.71 (d, 1H, J=9.0 Hz), 7.44 (d, 1H, J=9.0 Hz), 7.24 (m, 2H), 3.94 (s, 3H); HRMS calcd for C$_7$H$_{12}$N$_5$OSClF (M+H$^+$): 388.0435, found 388.0426.

Methyl 9-(2,4-dichlorophenylamino)thiazolo[5,4-f]quinazoline-2-carbimidate 72

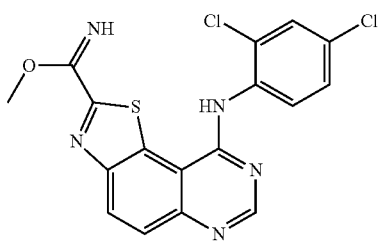 [SMILES: COC(=N)c1nc2ccc3ncnc(Nc4ccc(Cl)cc4Cl)c3c2s1]

Prepared from carbonitrile VIIIab. Flash chromatography eluent (EtOAc). Yield: 81%; yellow solid; mp>260° C.; IR (KBr) $v_{max}$/cm$^{-1}$ 2953, 1727, 1641, 1586, 1507, 1488, 1464, 1394, 1354, 1284, 1158, 1099, 1073, 1054, 941, 860, 816; $^1$H NMR (300 MHz, DMSO-d$_6$) δ 9.34 (s, 1H, NH), 8.45 (d, 1H, J=9.0 Hz), 8.10 (s, 1H), 7.71 (d, 1H, J=9.0 Hz), 7.62 (s, 1H), 7.38 (d, 1H, J=8.1 Hz), 7.18 (d, 1H, J=8.1 Hz), 3.93 (s, 3H); HRMS calcd for C$_{17}$H$_{12}$N$_5$OSCl$_2$ (M+H$^+$): 404.0140, found 404.0146.

Methyl 9-(4-methoxy-3-nitrophenylamino)thiazolo[5,4-f]quinazoline-2-carbimidate 73

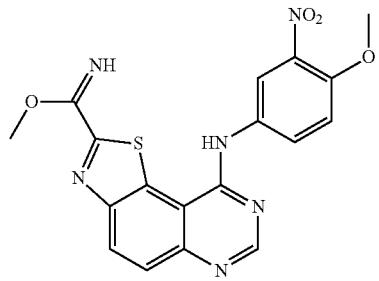

Prepared from carbonitrile VIIIbb. Flash chromatography eluent (DCM-MeOH, 95:5). Yield: 59%; yellow solid; mp 214° C.; IR (KBr) $v_{max}$/cm$^{-1}$ 1731, 1643, 1603, 1520, 1489, 1438, 1345, 1266, 1158, 1072, 1014, 946, 870, 821, 810; $^1$H NMR (300 MHz, DMSO-d$_6$) δ 9.32 (s, 1H, NH), 8.40 (d, 1H, J=9.0 Hz), 8.17 (s, 1H), 7.82 (d, 1H, J=9.0 Hz), 7.66 (d, 1H, J=9.0 Hz), 7.55 (d, 1H, J=8.1 Hz), 7.36 (d, 1H, J=9.0 Hz), 3.95 (s, 3H), 3.92 (s, 3H); HRMS calcd for C$_{18}$H$_{15}$N$_6$O$_4$S (M+H$^+$): 411.0876, found 411.0869.

Methyl 9-(4-tert-butylphenylamino)thiazolo[5,4-f]quinazoline-2-carbimidate 74

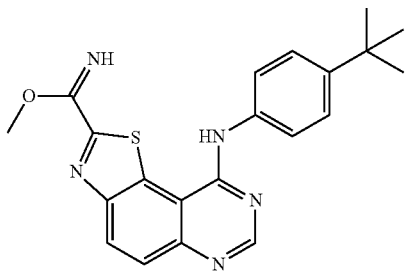 [SMILES: COC(=N)c1nc2ccc3ncnc(Nc4ccc(C(C)(C)C)cc4)c3c2s1]

Prepared from carbonitrile VIIIcb. Flash chromatography eluent (EtOAc). Yield: 69%; yellow solid; mp>260° C.; IR (KBr) $v_{max}$/cm$^{-1}$ 3267, 2939, 1731, 1644, 1599, 1580, 1493, 1342, 1269, 1248, 1161, 1114, 1066, 988, 965, 941, 899, 838; $^1$H NMR (300 MHz, DMSO-d$_6$) δ 9.31 (s, 1H, NH), 8.39 (d, 1H, J=9.0 Hz), 8.17 (s, 1H), 7.84 (d, 1H, J=9.0 Hz), 7.41 (d, 2H, J=7.8 Hz), 7.12 (m, 2H), 3.93 (s, 3H), 1.31 (s, 9H); HRMS calcd for $C_{22}H_{22}N_5OS$ (M+H$^+$): 392.1545, found 392.1539.

Methyl 9-(3-chlorophenylamino)thiazolo[5,4-f]quinazoline-2-carbimidate 75

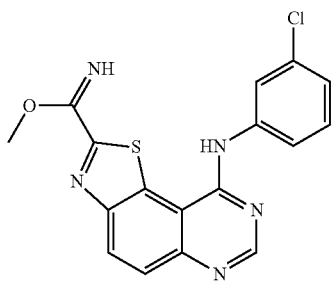 [SMILES: COC(=N)c1nc2ccc3ncnc(Nc4cccc(Cl)c4)c3c2s1]

Prepared from carbonitrile VIIIdb. Flash chromatography eluent (EtOAc). Yield: 78%; pale yellow solid; mp 235° C.; IR (KBr) $v_{max}$/cm$^{-1}$ 3293, 2950, 1639, 1593, 1550, 1507, 1470, 1437, 1355, 1286, 1157, 1070, 994, 968, 943, 876, 821; $^1$H NMR (300 MHz, DMSO-d$_6$) δ 9.32 (s, 1H, NH), 8.40 (d, 1H, J=9.0 Hz), 8.11 (s, 1H), 7.67 (d, 1H, J=9.0 Hz), 7.37 (t, 1H, J=7.8 Hz), 7.23 (m, 1H), 7.12-7.08 (m, 2H), 3.94 (s, 3H); HRMS calcd for $C_{17}H_{13}N_5OSCl$ (M+H$^+$): 370.0529, found 370.0524.

Methyl 9-(4-(dimethylamino)phenylamino)thiazolo[5,4-f]quinazoline-2-carbimidate 76

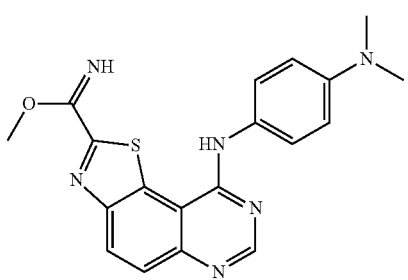

Prepared from carbonitrile VIIIeb. Flash chromatography eluent (EtOAc). Yield: 94%; beige solid; mp>260° C.; IR (KBr) $v_{max}$/cm$^{-1}$ 3288, 2945, 1629, 1608, 1577, 1520, 1496, 1444, 1337, 1291, 1275, 1209, 1183, 1167, 1068, 968, 943, 820; $^1$H NMR (300 MHz, DMSO-d$_6$) δ 9.35 (s, 1H, NH), 8.42 (d, 1H, J=9.0 Hz), 8.07 (s, 1H), 7.77 (d, 1H, J=9.0 Hz), 7.36 (d, 2H, J=8.4 Hz), 6.91 (d, 2H, J=8.4 Hz), 3.94 (s, 3H), 2.99 (s, 3H); HRMS calcd for $C_{19}H_{19}N_6OS$ (M+H$^+$): 379.1341, found 379.1330.

Methyl 9-(4-(pyrrolidin-1-yl)phenylamino)thiazolo[5,4-f]quinazoline-2-carbimidate 77

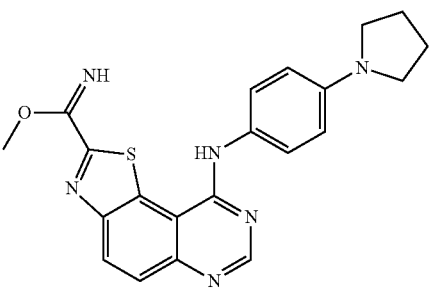 [SMILES: COC(=N)c1nc2ccc3ncnc(Nc4ccc(N5CCCC5)cc4)c3c2s1]

Prepared from carbonitrile VIIIfb. Flash chromatography eluent (DCM-EtOAc, 5:5). Yield: 75%; beige solid; mp>260° C.; IR (KBr) $v_{max}$/cm$^{-1}$ 3293, 2847, 1632, 1608, 1577, 1520, 1491, 1444, 1388, 1293, 1265, 1209, 1178, 1163, 1107, 1062, 968, 927, 820, 806; $^1$H NMR (300 MHz, DMSO-d$_6$) δ 9.35 (s, 1H, NH), 8.42 (d, 1H, J=9.0 Hz), 8.06 (s, 1H), 7.77 (d, 1H, J=9.0 Hz), 7.34 (d, 2H, J=8.4 Hz), 6.72 (d, 2H, J=8.4 Hz), 3.94 (s, 3H), 3.29 (m, 4H), 1.98 (m, 4H); HRMS calcd for $C_{21}H_{21}N_6OS$ (M+H$^+$): 405.1457, found 405.1452.

Methyl 9-(2,4-difluorophenylamino)thiazolo[5,4-f]quinazoline-2-carbimidate 78

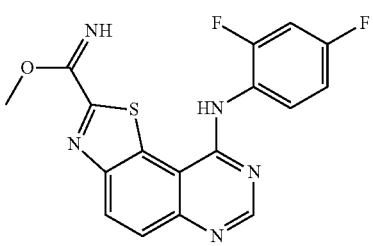 [SMILES: COC(=N)c1nc2ccc3ncnc(Nc4ccc(F)cc4F)c3c2s1]

Prepared from carbonitrile VIIIgb. Flash chromatography eluent (EtOAc). Yield: 71%; yellow solid; mp>260° C.; IR (KBr) $v_{max}$/cm$^{-1}$ 1644, 1608, 1574, 1556, 1509, 1488, 1435, 1357, 1285, 1260, 1188, 1140, 1073, 963, 943, 843, 819; $^{19}$F NMR (282 MHz, DMSO-d$_6$) δ -117.6, -118.8; $^1$H NMR (300 MHz, DMSO-d$_6$) δ 9.34 (s, 1H, NH), 8.45 (d, 1H, J=9.0 Hz), 8.12 (s, 1H), 7.70 (d, 1H, J=9.0 Hz), 7.27 (m, 2H), 7.05 (t, 1H, J=7.8 Hz), 3.94 (s, 3H); HRMS calcd for $C_{17}H_{12}N_5OSF_2$ (M+H$^+$): 372.0731, found 372.0725.

Methyl 9-(3-fluoro-4-hydroxyphenylamino)thiazolo[5,4-f]quinazoline-2-carbimidate 79

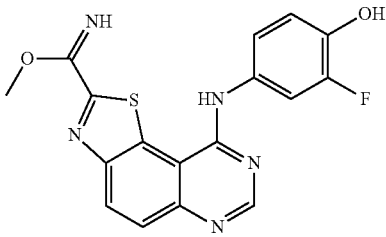 [SMILES: COC(=N)c1nc2ccc3ncnc(Nc4ccc(O)c(F)c4)c3c2s1]

Prepared from VIIIhb. Flash chromatography eluent (EtOAc). Yield: 70%; pale brown solid; mp>260° C.; IR (KBr) $v_{max}$/cm$^{-1}$ 3374, 1729, 1652, 1626, 1585, 1519, 1465, 1386, 1352, 1302, 1241, 1209, 1156, 1111, 978, 856, 827; $^{19}$F NMR (282 MHz, DMSO-d$_6$) δ −138.5; $^1$H NMR (300 MHz, DMSO-d$_6$) δ 8.52 (d, 1H, J=9.0 Hz), 8.19 (s, 1H), 7.72 (d, 1H, J=9.0 Hz), 7.04-6.91 (m, 3H), 3.95 (s, 3H); HRMS calcd for C$_{17}$H$_{13}$N$_5$O$_2$SF (M+H$^+$): 370.0774, found 370.0762.

Methyl 9-(4-(trifluoromethyl)phenylamino)thiazolo[5,4-f]quinazoline-2-carbimidate 80

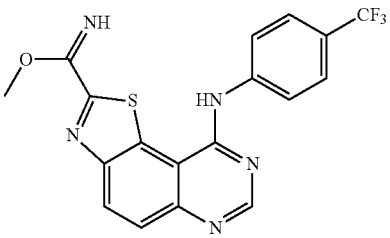 [SMILES: COC(=N)c1nc2ccc3ncnc(Nc4ccc(C(F)(F)F)cc4)c3c2s1]

Prepared from VIIIib. Flash chromatography eluent (EtOAc). Yield: 53%; pale yellow solid; mp>260° C.; IR (KBr) $v_{max}$/cm$^{-1}$ 3277, 1643, 1601, 1588, 1561, 1509, 1493, 1324, 1284, 1151, 1104, 1065, 1015, 966, 937, 829, 809; $^{19}$F NMR (282 MHz, DMSO-d$_6$) δ −59.95; $^1$H NMR (300 MHz, DMSO-d$_6$) δ 8.42 (d, 1H, J=9.0 Hz), 8.11 (s, 1H), 7.69 (d, 3H, J=7.8 Hz), 7.32 (d, 2H, J=7.8 Hz), 3.93 (s, 3H); HRMS calcd for C$_{18}$H$_{13}$N$_5$OSF$_3$ (M+H$^+$): 404.0736, found 404.0742.

6) General Procedure for the Synthesis of Ethylimidates 81 & 82

A stirred mixture of carbonitrile (0.13 mmol) and NaOCH$_2$CH$_3$ (0.5 M sol. in EtOH, 130 μL) in ethanol (4 mL) was irradiated under microwaves at 80° C. for 30 min. The solvent was removed in vacuo and the crude residue purified by flash chromatography to afford the imidates 81 & 82.

Ethyl 9-(4-bromo-2-fluorophenylamino)thiazolo[5,4-f]quinazoline-2-carbimidate 81

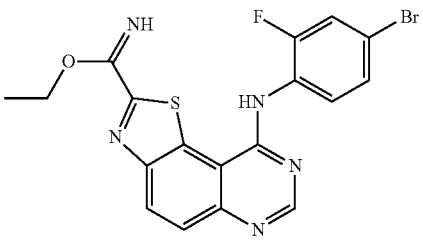 [SMILES: CCOC(=N)c1nc2ccc3ncnc(Nc4ccc(Br)cc4F)c3c2s1]

Prepared from carbonitrile VIIIba. Flash chromatography eluent (DCM-EtOAc, 2:8). Yield: 64%; yellow solid; mp 220° C.; IR (KBr) $v_{max}$/cm$^{-1}$ 3658, 3072, 2360, 1638, 1582, 1494, 1377, 1333, 1309, 1260, 1225, 1197, 1167, 1120, 1088, 1025, 966, 932, 882, 830; $^{19}$F NMR (282 MHz, DMSO-d$_6$) δ −122.4; $^1$H NMR (300 MHz, DMSO-d$_6$) δ 8.46 (d, 1H, J=9.0 Hz), 8.15 (s, 1H), 7.72 (d, 1H, J=9.0 Hz), 7.54-7.39 (m, 2H), 7.20 (t, 1H, J=9.0 Hz), 4.38 (q, 2H, J=7.0 Hz), 1.37 (t, 3H, J=7.0 Hz); HRMS calcd for C$_8$H$_{14}$N$_5$OSBrF (M+H$^+$): 446.0086, found 446.0082.

Ethyl 9-(benzo[d][1,3]dioxol-5-ylamino)thiazolo[5,4-j]quinazoline-2-carbimidate 82

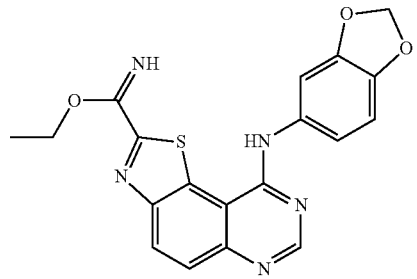 [SMILES: CCOC(=N)c1nc2ccc3ncnc(Nc4ccc5c(c4)OCO5)c3c2s1]

Prepared from carbonitrile VIIIfa. Flash chromatography eluent (DCM-EtOAc, 5:5). Yield: 79%; yellow solid; mp 193° C.; IR (KBr) $v_{max}$/cm$^{-1}$ 3286, 2892, 1722, 1654, 1626, 1579, 1497, 1484, 1465, 1372, 1334, 1242, 1230, 1184, 1159, 1128, 1036, 966, 923, 824; $^1$H NMR (300 MHz, DMSO-d$_6$) δ 8.39 (d, 1H, J=9.0 Hz), 7.94 (s, 1H), 7.68 (d, 1H, J=9.0 Hz), 6.94 (d, 1H, J=8.1 Hz), 6.76-6.46 (m, 2H), 6.01 (s, 2H), 4.38 (q, 2H, J=6.9 Hz), 1.38 (t, 3H, J=6.9 Hz); HRMS calcd for C$_{19}$H$_{16}$N$_5$O$_3$S (M+H): 394.0974, found 394.0967.

7) Synthesis of Benzylimidate: benzyl 9-(benzo[d][1,3]dioxol-5-ylamino)thiazolo[5,4-f]quinazoline-2-carbimidate 83

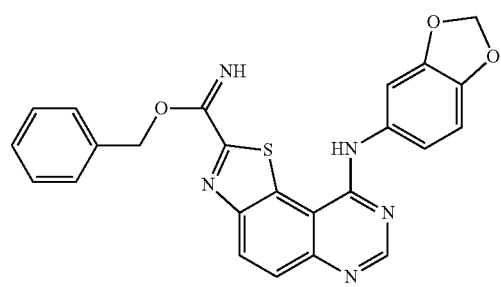 [SMILES: N=C(OCc1ccccc1)c1nc2ccc3ncnc(Nc4ccc5c(c4)OCO5)c3c2s1]

A stirred mixture of carbonitrile VIIIfa (0.05 g, 0.14 mmol) and NaOCH₂Ph (1.0 M sol. in benzylalcohol, 70 μL) in benzylalcohol (3 mL) was irradiated under microwaves at 100° C. for 30 min. The solvent was removed in vacuo and the crude residue purified by flash chromatography (EtOAc) to afford the imidate 83 as a yellow solid (0.018 g, 28% yield); mp 182° C.; IR (KBr) $v_{max}$/cm$^{-1}$ 3375, 2228, 1726, 1644, 1613, 1575, 1473, 1378, 1327, 1244, 1192, 1151, 1036, 922, 833; $^1$H NMR (300 MHz, DMSO-d₆) δ 8.42 (d, 1H, J=9.0 Hz), 7.99 (s, 1H), 7.68 (d, 1H, J=9.0 Hz), 7.51 (d, 2H, J=7.5 Hz), 7.43-7.34 (m, 3H), 6.92 (d, 1H, J=7.5 Hz), 6.78 (m, 1H), 6.59 (m, 1H), 6.01 (s, 2H), 5.45 (s, 2H); HRMS calcd for C₂₄H₁₈N₅O₃S (M+H⁺): 456.1130, found 456.1128.

8) Synthesis of methyl ester:methyl 9-(benzo[d][1,3]dioxol-5-ylamino)thiazolo[5,4-f]quinazoline-2-carboxylate 84

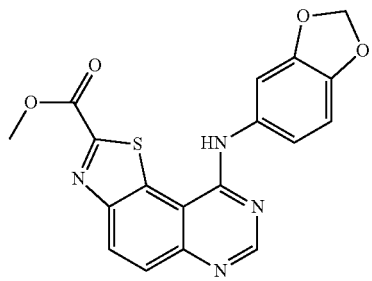 [SMILES: COC(=O)c1nc2ccc3ncnc(Nc4ccc5c(c4)OCO5)c3c2s1]

A mixture of methyl 9-(benzo[d][1,3]dioxol-5-ylamino)thiazolo[5,4-j]quinazoline-2-carbimidate 48 (0.017 mmol) and 5 mL of MeOH/H₂O+TFA(0.1%) (60/40) under argon was stirred at room temperature overnight. The solvent was removed in vacuo and the crude residue purified by flash chromatography (DCM-EtOAc, 5:5) to afford the ester 84 (5.9 mg, 94% yield) as a yellow solid; mp>260° C.; IR (KBr) $v_{max}$/cm$^{-1}$ 3287, 2902, 1648, 1617, 1575, 1528, 1499, 1483, 1452, 1432, 1385, 1322, 1272, 1196, 1125, 1043, 936, 885, 834, 817; $^1$H NMR (300 MHz, DMSO-d₆) δ 8.42 (d, 1H, J=9.0 Hz), 8.03 (s, 1H), 7.95 (d, 1H, J=9.0 Hz), 6.96 (d, 1H, J=8.0 Hz), 6.84 (m, 1H), 6.72 (d, 1H, J=8.0 Hz), 5.94 (s, 2H), 4.05 (s, 3H); HRMS calcd for C₁₈H₁₃N₄O₄S (M+H⁺): 381.0658, found 381.0651.

9) Synthesis of isopropylimidate:isopropyl 9-(benzo[d][1,3]dioxol-5-ylamino)thiazolo[5,4-f]quinazoline-2-carbimidate 85

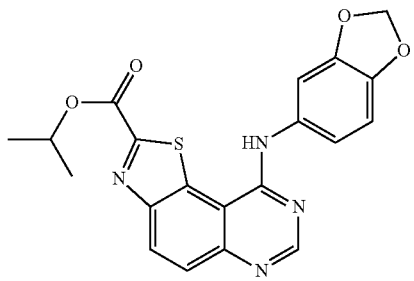 [SMILES: CC(C)OC(=O)c1nc2ccc3ncnc(Nc4ccc5c(c4)OCO5)c3c2s1]

A stirred mixture of carbonitrile VIIIfa (0.078 g, 0.22 mmol) and KOH (2.5 N sol., 78 μL) in isopropanol (3.9 mL) was irradiated under microwaves at 100° C. for 2 h. The solvent was removed in vacuo and the crude residue purified by flash chromatography (DCM-EtOAc, 5:5) to afford the imidate 85 as a yellow solid (0.024 g, 27% yield); mp 225° C.; IR (KBr) $v_{max}$/cm$^{-1}$3267, 2977, 2876, 1638, 1613, 1572, 1489, 1475, 1450, 1382, 1369, 1317, 1272, 1244, 1189, 1142, 1112, 1036, 924, 885, 828, 808; $^1$H NMR (300 MHz, DMSO-d₆) δ 8.40 (d, 1H, J=9.0 Hz), 7.94 (s, 1H), 7.68 (d, 1H, J=9.0 Hz), 6.94 (d, 2H, J=8.1 Hz), 6.75-6.55 (m, 2H), 6.01 (s, 2H), 5.32-5.24 (m, 1H), 1.38 (d, 6H, J=6.0 Hz). HRMS calcd for C₂₀H₁₈N₅O₃S (M+H⁺): 408.0962, found 408.0956.

10) Synthesis of Carboxamide: 9-((2-bromo-4-fluorophenyl)amino)thiazolo[5,4-f]quinazoline-2-carboxamide 86

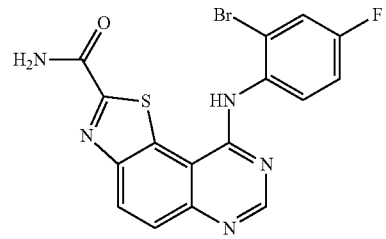 [SMILES: NC(=O)c1nc2ccc3ncnc(Nc4ccc(F)cc4Br)c3c2s1]

Prepared from carbonitrile VIIIwa following procedure described for carboxamides 35-40. Flash chromatography eluent (DCM-EtOAc, 5:5). Yield: 44%; yellow solid; mp 210° C.; IR (KBr) $v_{max}$/cm$^{-1}$ 3150 (NH), 2920, 1736 (CO), 1671, 1636, 1606, 1579, 11491, 11460, 1410, 1384, 1254, 1209, 1158, 966, 832, 779; $^1$H NMR (300 MHz, DMSO-d₆) δ 8.46 (s, 1H), 8.42 (d, 1H, J=9.0 Hz), 8.01 (s, 1H), 7.72 (d, 1H, J=9.0 Hz), 7.63 (d, 1H, J=9.0 Hz), 7.25-7.20 (m, 1H), 7.18-7.13 (m, 1H); HRMS calcd for C₁₆H₁₀N₅OSBrF (M+H⁺): 417.9773, found 417.9760.

11) Synthesis of carboxamide: 9-((2,4-dichlorophenyl)amino)thiazolo[5,4-f]quinazoline-2-carboxamide 87

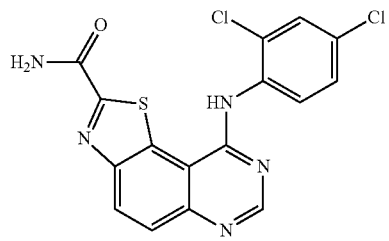 [SMILES: NC(=O)c1nc2ccc3ncnc(Nc4ccc(Cl)cc4Cl)c3c2s1]

Prepared from carbonitrile VIIIab following procedure described for carboxamides 35-40. Flash chromatography eluent (DCM-EtOAc, 5:5). Yield: 22%; yellow solid; mp>260° C.; IR (KBr) $v_{max}$/cm$^{-1}$ 3150 (NH), 1701 (CO), 1587, 1505, 1470, 1384, 1283, 1099, 808; $^1$H NMR (300 MHz, DMSO-d₆) δ 8.46 (s, 1H), 8.42 (d, 1H, J=9.0 Hz), 8.03 (s, 1H), 7.72 (s, 1H), 7.63 (s, 1H), 7.38 (d, 1H, J=6 Hz), 7.19 (d, 1H, J=9 Hz).

12) Synthesis of butyl 9-((2,4-dichlorophenyl)amino)thiazolo[5,4-f]quinazoline-2-carbimidate 88

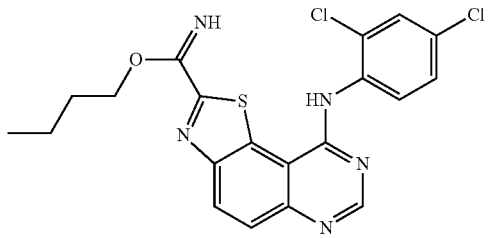 [SMILES: CCCCOC(=N)c1nc2ccc3ncnc(Nc4ccc(Cl)cc4Cl)c3c2s1]

A stirred mixture of carbonitrile VIIIab (0.05 g, 0.13 mmol) and NaOH (2.5 M sol. in water, 50 µL) in butanol (2.5 mL) was irradiated under microwaves at 117° C. for 30 min. The solvent was removed in vacuo and the crude residue purified by flash chromatography (DCM-EtOAc, 7:3) to afford the imidate 88 as a yellow solid (0.058 g, 33% yield); mp 178° C.; IR (KBr) $v_{max}$/cm$^{-1}$ 2965, 1641 (CO), 1578, 1557, 1504, 1458, 1370, 1325, 1284, 1152, 1099, 1071, 962, 811; $^1$H NMR (300 MHz, DMSO-d$_6$) δ 9.28 (s, 1H, NH), 8.45 (d, 1H, J=9.0 Hz), 8.09 (s, 1H), 7.71 (d, 1H, J=9.0 Hz), 7.60 (d, 1H, J=2.0 Hz), 7.36 (dd, 1H, J=9.0 and J 2.0 Hz), 7.22 (d, 1H, J=9.0 Hz), 4.34 (t, 2H, J=7.0 Hz), 1.77 (q, 2H, J=7.0 Hz), 1.47 (q, 2H, J=7.0 Hz), 0.95 (t, 3H, J=7.0 Hz); HRMS calcd for $C_{20}H_{18}N_5OSCl_2$ (M+H$^+$): 446.0609, found 446.0618.

12) Synthesis of methyl ester: methyl 9-((2,4-dichlorophenyl)amino)thiazolo[5,4-f]quinazoline-2-carboxylate 89

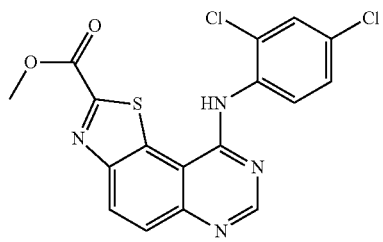 [SMILES: COC(=O)c1nc2ccc3ncnc(Nc4ccc(Cl)cc4Cl)c3c2s1]

A mixture of methyl 9-(2,4-dichlorophenylamino)thiazolo[5,4-f]quinazoline-2-carbimidate 72 (0.04 g, 0.01 mmol) in Tetrahydrofurane (THF, 1 mL) and 1 mL of diluted $H_2SO_4$ (0.5 mL in 10 mL of water was stirred) under argon at room temperature for 2 h. Water was added and the precipitate formed was filtered and washed with water. The crude residue purified by flash chromatography (DCM-MeOH, 9:1) to afford the ester 89 (19.4 mg, 48% yield) as a yellow solid; mp 202° C.; IR (KBr) $v_{max}$/cm$^{-1}$ 1742 (CO), 1584, 1552, 1501, 1482, 1470, 1391, 1296, 1245, 1099, 1080, 1055, 936, 858, 827, 808; $^1$H NMR (300 MHz, DMSO-d$_6$) δ 8.52 (d, 1H, J=9.0 Hz), 8.15 (s, 1H),), 7.75 (d, 1H, J=9.0 Hz), 7.62 (s, 1H), 7.37 (d, 1H, J=9.0 Hz), 7.23 (d, 1H, J=9.0 Hz), 3.99 (s, 3H).

Example 2

Biological Activity

The biological activity of compounds of formula (I) was evaluated using an in vitro functional assay.

Kinase Assays

The DYRK1A and DYRK1B kinase assays to determine $IC_{50}$ values were performed by Reaction Biology Corporation using HotSpot technology Worldwide website: reactionbiology.com, Malvern, PA). Kinase reaction with specific kinase/ substrate pair along with required cofactors was carried out in 20 mM Hepes pH 7.5, 10 mM MgCl$_2$, 1 mM EGTA, 0.02% Brij35, 0.02 mg/ml BSA, 0.1 mM Na$_3$VO$_4$, 2 mM DTT, 1% DMSO. Purified recombinant kinase was incubated with serial 3-fold dilutions of test compounds starting at a final concentration of 10 µM. Reaction was initiated by addition of a mixture of ATP (Sigma, St. Louis MO) and $^{33}$P ATP (Perkin Elmer, Waltham MA) to a final concentration of 10 µM and was carried out at room temperature for 120 min, followed by spotting of the reaction onto P81 ion exchange filter paper (Whatman Inc., Piscataway, NJ). Unbound phosphate was removed by extensive washing of filters in 0.75% Phosphoric acid. Dose response curves were fitted using Prism 5.0 from Graph-Pad Software.

Results

Results are reported in table 2.

TABLE 2

| Compound number | IC$_{50}$ nM DYRK1A | DYRK1B | Compound number | IC$_{50}$ nM DYRK1A | DYRK1B |
|---|---|---|---|---|---|
| 23 | 1000 < IC$_{50}$ < 10000 | | 35 | 1000 < IC$_{50}$ < 10000 | |
| 25 | 1000 < IC$_{50}$ < 10000 | | 43 | 1 < IC$_{50}$ < 1000 | |
| 29 | 1000 < IC$_{50}$ < 10000 | | 7 | 1000 < IC$_{50}$ < 10000 | |
| 30 | 1000 < IC$_{50}$ < 10000 | | 28 | 1 < IC$_{50}$ < 1000 | |
| 31 | 1000 < IC$_{50}$ < 10000 | | 38 | 1000 < IC$_{50}$ < 10000 | |
| 33 | 431.2 | | 47 | 2.76 | 3.66 |
| 34 | 1000 < IC$_{50}$ < 10000 | | 39 | 1 < IC$_{50}$ < 1000 | |
| 14 | 146.6 | | 84 | 1 < IC$_{50}$ < 1000 | |
| 16 | 1000 < IC$_{50}$ < 10000 | | 48 | 1.65 | 4.20 |
| 81 | 33.2 | 34.4 | 49 | 8.00 | 17.60 |
| 19 | 1000 < IC$_{50}$ < 10000 | | 51 | 128.80 | 160.6 |
| 44 | 3.60 | 6.55 | 53 | 1 < IC$_{50}$ < 1000 | |
| 36 | 194.4 | | 40 | 1000 < IC$_{50}$ < 10000 | |
| 45 | 13.08 | 19.22 | 54 | 4.25 | |
| 37 | 142.5 | | 55 | 17.48 | |
| 56 | 1.13 | 4.74 | 71 | 0.99 | 1.63 |

TABLE 2-continued

| Compound number | IC$_{50}$ nM DYRK1A | IC$_{50}$ nM DYRK1B | Compound number | IC$_{50}$ nM DYRK1A | IC$_{50}$ nM DYRK1B |
|---|---|---|---|---|---|
| 57 | 66.82 | 99.34 | 72 | 0.22 | 0.28 |
| 58 | 40.76 | 46.29 | 73 | 123.50 | 599.80 |
| 59 | 4.44 | 4.65 | 74 | 39.03 | 93.84 |
| 60 | 4.91 | 5.68 | 83 | 33.93 | 37.34 |
| 46 | 79.85 | 84.94 | 82 | 6.02 | 7.72 |
| 52 | 3768.00 | 4458.00 | 75 | 13.64 | 18.78 |
| 61 | 436.10 | 485.80 | 76 | 35.64 | 64.28 |
| 42 | 11000.00 | 18720.00 | 77 | 54.84 | 186.40 |
| 62 | 9.53 | 11.13 | 78 | 0.94 | 1.07 |
| 63 | 298.90 | 530.90 | 79 | 8.63 | 11.00 |
| 64 | 1.81 | 3.48 | 80 | 18.26 | 25.21 |
| 65 | 0.98 | 2.83 | 85 | 124.7 | 217.80 |
| 66 | 6.06 | 9.64 | 86 | 26.2 | 31.50 |
| 67 | 42.70 | 71.98 | 87 | 34.9 | 43.4 |
| 68 | 0.16 | 0.24 | 88 | 47.5 | 69.40 |
| 69 | 0.36 | 0.59 | 89 | 5.1 | 7.70 |
| 70 | 3.89 | 7.69 | | | |

Harmine, TG003, NCGC-00189310 and Leucettine L41 (see Table 1) were also tested has reference DYRK1A and DYRK1B inhibitors. They respectively elicited a DYRK1A IC$_{50}$ of 21.83, 24.01 nM, 2.20 nM and 7.60 nM and a DYRK1B IC$_{50}$ of 27.87, 34.39 nM, 20.57 nM and 37.00 nM.

The invention claimed is:

1. A compound of formula (I):

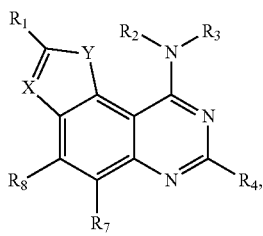

wherein:
X is a nitrogen atom;
Y is an oxygen atom, a sulfur atom, a NH group or a N—(C1-C3)alkyl group;
R1 is a —C(=A)-B group, wherein:
A is NH or O and
B is a OR5 or a NR5R6 group, wherein:
R5 and R6 are independently chosen from a hydrogen atom and an unsubstituted or substituted C1-C8 alkyl group;
A and B can alternatively independently be nitrogen and/or oxygen atoms and form, with the carbon atom to which they are bound, a heterocycloalkyl group;
R2 is a hydrogen atom or an unsubstituted C1-C8 alkyl group;
R3 is an unsubstituted or substituted C1-C8 alkyl or an unsubstituted or substituted aryl or heteroaryl group;
R4 is a hydrogen atom, a halogen atom, an amino group, a cyano group or an unsubstituted or substituted C1-C5 alkyl group;
R7 and R8 are independently chosen from a hydrogen atom, a halogen atom, a hydroxyl group, or an unsubstituted or substituted C1-C5 alkyl group or pharmaceutically acceptable salts thereof.

2. The compound according to claim 1, wherein:
Y is a sulfur atom;
A is NH;
A is NH and B is a NR5R6 group;
A is NH and B is a OR5 group;
A is NH and B is a OCH3 group;
A is O and B is NH2;
R6 is a hydrogen atom;
R2 is a hydrogen atom;
R3 is an unsubstituted C1-C8 alkyl group, a C1-C8 alkyl group substituted by an alkoxyl group, a C1-C8 alkyl group substituted by a cycloalkyl group, or a C1-C8 alkyl group substituted by an aryl or a heteroaryl group;
R3 is an unsubstituted aryl group or an aryl group substituted by at least one group selected from halogen atoms and alkoxyl groups; or
R4, R6 and R7 are hydrogen atoms.

3. The compound according to claim 1, wherein R3 is a substituted or unsubstituted aryl or heteroaryl group.

4. The compound according to claim 1, wherein:
Y is a sulphur atom;
A is NH;
B is a OR5 group wherein R5 is an unsubstituted (C1-C8)alkyl group;
R2, R4, R7 and R8 are hydrogen atoms; and
R3 is an ethyl group substituted by a (C1-C4)alkoxy group or an aryl group substituted with one or two substituents selected from the group consisting of a (C1-C4)alkyl, a halogen atom and a (C1-C4)alkoxy group.

5. The compound according to claim 1, selected from the group consisting of:
9-(3-Chloro-4-fluorophenylamino)-N-(2-morpholino-ethyl)thiazolo[5,4-f]quinazoline-2-carboximidamide (compound 1);
9-(3-Chloro-4-fluorophenylamino)-N-(2-(piperidin-1-yl)ethyl)thiazolo[5,4-f]quinazoline-2-carboximidamide (compound 2);
9-(3-Chloro-4-fluorophenylamino)-N-(2-(pyrrolidin-1-yl)ethyl)thiazolo[5,4-f]quinazoline -2-carboximidamide (compound 3);
9-(3-Chloro-4-fluorophenylamino)-N-(2-(dimethylamino)ethyl)thiazolo[5,4-f]quinazoline -2-carboximidamide (compound 4);

9-(3-Chloro-4-fluorophenylamino)-N-(2-(diethylamino) ethyl)thiazolo[5,4-f]quinazoline-2-carboximidamide (compound 5);

N-Benzyl-9-(3-chloro-4-fluorophenylamino)thiazolo[5, 4-f]quinazoline-2-carboximidamide (compound 6);

9-(3-Chloro-4-fluorophenylamino)-N,N-dimethylthiazolo[5,4-f]quinazoline-2-carboximidamide (compound 7);

9-(4-Bromo-2-fluorophenylamino)-N-(2-morpholinoethyl)thiazolo[5,4-f]quinazoline-2-carboximidamide (compound 8);

9-(4-Bromo-2-fluorophenylamino)-N-(2-(piperidin-1-yl) ethyl)thiazolo[5,4-f]quinazoline-2-carboximidamide (compound 9);

9-(4-Bromo-2-fluorophenylamino)-N-(2-(dimethylamino)ethyl)thiazolo[5,4-f]quinazoline-2-carboximidamide (compound 10);

9-(4-Bromo-2-fluorophenylamino)-N-(2-(diethylamino) ethyl)thiazolo[5,4-f]quinazoline-2-carboximidamide (compound 11);

9-(4-Bromo-2-fluorophenylamino)-N-(2-(pyrrolidin-1-yl)ethyl)thiazolo[5,4-f]quinazoline-2-carboximidamide (compound 12);

N-Benzyl-9-(4-bromo-2-fluorophenylamino)thiazolo[5, 4-f]quinazoline-2-carboximidamide (compound 13);

9-(4-Bromo-2-fluorophenylamino)-N-(2-(dimethylamino)ethyl)thiazolo[5,4-f]quinazoline -2-carboximidamide (compound 14);

9-(4-Bromo-2-fluorophenylamino)-N-isopropylthiazolo [5,4-f]quinazoline-2-carboximidamide (compound 15);

9-(4-Bromo-2-fluorophenylamino)-N-(4-fluorobenzyl) thiazolo[5,4-f]quinazoline-2-carboximidamide (compound 16);

9-(4-Bromo-2-fluorophenylamino)-N-(3-fluorobenzyl) thiazolo[5,4-f]quinazoline-2-carboximidamide (compound 17);

9-(4-Bromo-2-fluorophenylamino)-N-(cyclohexylmethyl)thiazolo[5,4-f]quinazoline-2-carboximidamide (compound 18);

9-(4-Bromo-2-fluorophenylamino)-N-(pyridin-4-ylmethyl)thiazolo[5,4-f]quinazoline-2-carboximidamide (compound 19);

9-(3-Cyanophenylamino)-N-(2-morpholinoethyl)thiazolo [5,4-f]quinazoline-2-carboximidamide (compound 20);

9-(3-Cyanophenylamino)-N-(2-(piperidin-1-yl)ethyl)thiazolo[5,4-f]quinazoline-2-carboximidamide (compound 21);

N-(2-(Dimethylamino)ethyl)-9-(4-methoxyphenylamino) thiazolo[5,4-f]quinazoline-2-carboximidamide (compound 22);

N-(2-(Diethylamino)ethyl)-9-(4-methoxyphenylamino) thiazolo[5,4-f]quinazoline-2-carboximidamide (compound 23);

9-(4-Methoxyphenylamino)-N-(2-(pyrrolidin-1-yl)ethyl) thiazolo[5,4-f]quinazoline-2-carboximidamide (compound 24);

N-benzyl-9-(4-methoxyphenylamino)thiazolo[5,4-f]quinazoline-2-carboximidamide (compound 25);

9-(4-Methoxyphenylamino)-N-(2-morpholinoethyl)thiazolo[5,4-f]quinazoline-2-carboximidamide (compound 26);

9-(4-Methoxyphenylamino)-N-(2-(piperidin-1-yl)ethyl) thiazolo[5,4-f]quinazoline-2-carboximidamide (compound 27);

9-(4-Methoxyphenylamino)-N,N-dimethylthiazolo[5,4-f] quinazoline-2-carboximidamide (compound 28);

9-(Benzo[d][1,3]dioxol-5-ylamino)-N-(2-morpholinoethyl)thiazolo[5,4-f]quinazoline-2-carboximidamide (compound 29);

9-(Benzo[d][1,3]dioxol-5-ylamino)-N-(2-(piperidin-1-yl) ethyl)thiazolo[5,4-f]quinazoline-2-carboximidamide (compound 30);

9-(Benzo[d][1,3]dioxol-5-ylamino)-N-(2-(pyrrolidin-1-yl)ethyl)thiazolo[5,4-f]quinazoline-2-carboximidamide (compound 31);

9-(Benzo[d][1,3]dioxol-5-ylamino)-N-benzylthiazolo[5, 4-f]quinazoline-2-carboximidamide (compound 32);

9-(Benzo[d][1,3]dioxol-5-ylamino)-N-(2-(dimethylamino)ethyl)thiazolo[5,4-f]quinazoline-2 -carboximidamide (compound 33);

9-(Benzo[d][1,3]dioxol-5-ylamino)-N-(2-(diethylamino) ethyl)thiazolo[5,4-f]quinazoline-2-carboximidamide (compound 34);

9-(3-Chloro-4-fluorophenylamino)thiazolo[5,4-f]quinazoline-2-carboxamide (compound 35);

9-(4-Bromo-2-fluorophenylamino)thiazolo[5,4-f]quinazoline-2-carboxamide (compound 36);

9-(4-Methoxyphenylamino)thiazolo[5,4-f]quinazoline-2-carboxamide (compound 37);

9-(3,4,5-Trimethoxyphenylamino)thiazolo[5,4-f]quinazoline-2-carboxamide (compound 38);

9-(Benzo[d][1,3]dioxol-5-ylamino)thiazolo[5,4-f]quinazoline-2-carboxamide (compound 39);

9-(3,4-Dimethoxyphenylamino)thiazolo[5,4-f]quinazoline-2-carboxamide (compound 40);

N-(3-Chloro-4-fluorophenyl)-2-(4,5-dihydro-1H-imidazol-2-yl)thiazolo[5,4-f]quinazolin-9-amine (compound 41);

2-(4,5-dihydrooxazol-2-yl)-N-(4-methoxyphenyl)thiazolo[5,4-f]quinazolin-9-amine (compound 42);

Methyl 9-(3-chloro-4-fluorophenylamino)thiazolo[5,4-f] quinazoline-2-carbimidate (compound 43);

Methyl 9-(4-bromo-2-fluorophenylamino)thiazolo[5,4-f] quinazoline-2-carbimidate (compound 44);

Methyl 9-(4-methoxyphenylamino)thiazolo[5,4-f]quinazoline-2-carbimidate (compound 45);

Methyl 9-((4-methoxyphenyl)(methyl)amino)thiazolo[5, 4-f]quinazoline-2-carbimidate (compound 46);

Methyl 9-(7-bromobenzo[d][1,3]dioxol-5-ylamino)thiazolo[5,4-f]quinazoline-2-carbimidate (compound 47);

Methyl 9-(benzo[d][1,3]dioxol-5-ylamino)thiazolo[5,4-f] quinazoline-2-carbimidate (compound 48);

Methyl 9-(2,3-dihydrobenzo[b][1,4]dioxin-6-ylamino) thiazolo[5,4-f]quinazoline-2-carbimidate (compound 49);

Methyl 9-((2,3-dihydrobenzo[b][1,4]dioxin-6-yl) (methyl)amino)thiazolo[5,4-f]quinazoline-2-carbimidate (compound 50);

Methyl 9-(3,4-dimethoxyphenylamino)thiazolo[5,4-f] quinazoline-2-carbimidate (compound 51);

Methyl 9-((3,4-dimethoxyphenyl)(methyl)amino)thiazolo [5,4-f]quinazoline-2-carbimidate (compound 52);

Methyl 9-(4-hydroxyphenylamino)thiazolo[5,4-f]quinazoline-2-carbimidate (compound 53);

Methyl 9-(3-hydroxy-4-methoxyphenylamino)thiazolo[5, 4-f]quinazoline-2-carbimidate (compound 54);

Methyl 9-(2,3-dihydrobenzofuran-5-ylamino)thiazolo[5,4-f]quinazoline-2-carbimidate (compound 55);
Methyl 9-(4-chlorophenylamino)thiazolo[5,4-f]quinazoline-2-carbimidate (compound 56);
Methyl 9-(3,4-dichlorophenylamino)thiazolo[5,4-f]quinazoline-2-carbimidate (compound 57);
Methyl 9-(3-ethynylphenylamino)thiazolo[5,4-f]quinazoline-2-carbimidate (compound 58);
Methyl 9-(1H-benzo[d]imidazol-6-ylamino)thiazolo[5,4-f]quinazoline-2-carbimidate (compound 59);
Methyl 9-(4-hydroxy-3-nitrophenylamino)thiazolo[5,4-f]quinazoline-2-carbimidate (compound 60);
Methyl 9-(3,4,5-trimethoxyphenylamino)thiazolo[5,4-f]quinazoline-2-carbimidate (compound 61);
Methyl 9-(2,4-dimethoxyphenylamino)thiazolo[5,4-f]quinazoline-2-carbimidate (compound 62);
Methyl 9-(3,5-dimethoxyphenylamino)thiazolo[5,4-f]quinazoline-2-carbimidate (compound 63);
Methyl 9-(phenylamino)thiazolo[5,4-f]quinazoline-2-carbimidate (compound 64);
Methyl 9-(p-tolylamino)thiazolo[5,4-f]quinazoline-2-carbimidate (compound 65);
Methyl 9-(4-fluorophenylamino)thiazolo[5,4-f]quinazoline-2-carbimidate (compound 66);
Methyl 9-(3-cyanophenylamino)thiazolo[5,4-f]quinazoline-2-carbimidate (compound 67);
Methyl 9-(2-bromo-4-fluorophenylamino)thiazolo[5,4-f]quinazoline-2-carbimidate (compound 68);
Methyl 9-(2-fluoro-4-methoxyphenylamino)thiazolo[5,4-f]quinazoline-2-carbimidate (compound 69);
Methyl 9-(4-cyanophenylamino)thiazolo[5,4-f]quinazoline-2-carbimidate (compound 70);
Methyl 9-(4-chloro-2-fluorophenylamino)thiazolo[5,4-f]quinazoline-2-carbimidate (compound 71);
Methyl 9-(2,4-dichlorophenylamino)thiazolo[5,4-f]quinazoline-2-carbimidate (compound 72);
Methyl 9-(4-methoxy-3-nitrophenylamino)thiazolo[5,4-f]quinazoline-2-carbimidate (compound 73);
Methyl 9-(4-tert-butylphenylamino)thiazolo[5,4-f]quinazoline-2-carbimidate (compound 74);
Methyl 9-(3-chlorophenylamino)thiazolo[5,4-f]quinazoline-2-carbimidate (compound 75);
Methyl 9-(4-(dimethylamino)phenylamino)thiazolo[5,4-f]quinazoline-2-carbimidate (compound 76);
Methyl 9-(4-(pyrrolidin-1-yl)phenylamino)thiazolo[5,4-f]quinazoline-2-carbimidate (compound 77);
Methyl 9-(2,4-difluorophenylamino)thiazolo[5,4-f]quinazoline-2-carbimidate (compound 78);
Methyl 9-(3-fluoro-4-hydroxyphenylamino)thiazolo[5,4-f]quinazoline-2-carbimidate (compound 79);
Methyl 9-(4-(trifluoromethyl)phenylamino)thiazolo[5,4-f]quinazoline-2-carbimidate (compound 80);
Ethyl 9-(4-bromo-2-fluorophenylamino)thiazolo[5,4-f]quinazoline-2-carbimidate (compound 81);
Ethyl 9-(benzo[d][1,3]dioxol-5-ylamino)thiazolo[5,4-f]quinazoline-2-carbimidate (compound 82);
Benzyl 9-(benzo[d][1,3]dioxol-5-ylamino)thiazolo[5,4-f]quinazoline-2-carbimidate (compound 83);
Methyl 9-(benzo[d][1,3]dioxol-5-ylamino)thiazolo[5,4-f]quinazoline-2-carboxylate (compound 84);
Isopropyl 9-(benzo[d][1,3]dioxol-5-ylamino)thiazolo[5,4-f]quinazoline-2-carbimidate (compound 85);
9-((2-Bromo-4-fluorophenyl)amino)thiazolo[5,4-f]quinazoline-2-carboxamide (compound 86);
9-((2,4-Dichlorophenyl)amino)thiazolo[5,4-f]quinazoline-2-carboxamide (compound 87);
Butyl 9-((2,4-dichlorophenyl)amino)thiazolo[5,4-f]quinazoline-2-carbimidate (compound 88); and
Methyl 9-((2,4-dichlorophenyl)amino)thiazolo[5,4-f]quinazoline-2-carboxylate (compound 89).

6. A pharmaceutical composition comprising a compound according to claim 1, and a pharmaceutically acceptable carrier.

7. The pharmaceutical composition according to claim 6, further comprising another pharmaceutically active drug.

8. A method for the inhibition of dual-specificity tyrosine-regulated kinase 1A (DYRK1A) and/or dual-specificity tyrosine-regulated kinase 1B (DYRK1B) comprising administering to a subject in need thereof or to a cell a compound according to claim 1.

9. A method for the amelioration of symptoms associated with Alzheimer's disease comprising administering to a subject in need thereof a therapeutically effective amount of a compound according to claim 1, said therapeutically effective amount of said compound ameliorating the symptoms associated with Alzheimer's disease.

10. A process of synthesis of a compound of formula I

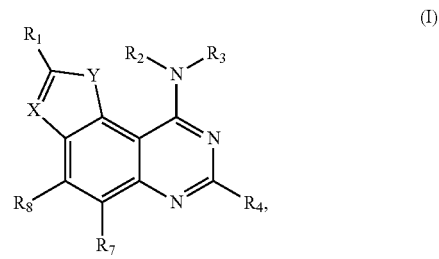

or pharmaceutically acceptable salts thereof,
wherein:

X is a nitrogen atom;

Y is an oxygen atom, a sulfur atom, a NH group or a N—(C1-C3)group;

R1 is a —C(=A)-B group, wherein:
  A is NH or O and
  B is a OR5 or a NR5R6 group, wherein:
  R5 and R6 are independently chosen from a hydrogen atom and an unsubstituted or substituted C1-C8 alkyl group;
A and B can alternatively independently be nitrogen and/or oxygen atoms and form, with the carbon atom to which they are bound, a heterocycloalkyl group;

R2 is a hydrogen atom or an unsubstituted C1-C8 alkyl group;

R3 is an unsubstituted or substituted C1-C8 alkyl or an unsubstituted or substituted aryl or heteroaryl group;

R4 is a hydrogen atom, a halogen atom, an amino group, a cyano group or an unsubstituted or substituted C1-C5 alkyl group;

R7 and R8 are independently chosen from a hydrogen atom, a halogen atom, a hydroxyl group, or an unsubstituted or substituted C1-C5 alkyl group comprising the steps of:
  a) condensing Appel's salt (4,5-dichloro-1,2,3-dithiazol-1-ium chloride

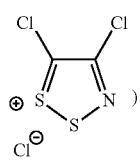

on a compound of formula (III)

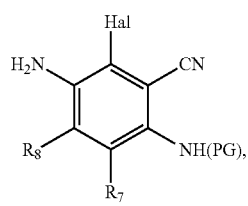

wherein (PG) is an amino protecting group and Hal is a halogen atom to form a compound of formula (IV)

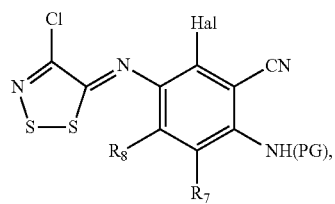

b) deprotecting the amino group of the compound of formula (IV), and cyclising the obtained compound of formula (V)

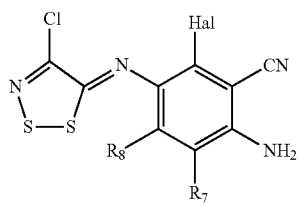

to form a compound of formula (VI)

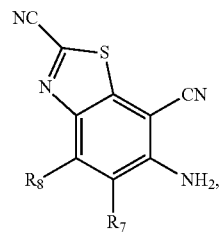

c) aminating the compound of formula (VI) obtained in step b) with dimethylformamide dimethylacetal to form a compound of formula (VII)

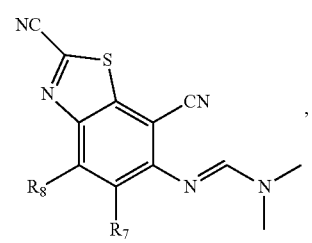

and
d) cyclising the compound of formula (VII) obtained in step c) to form a tricyclic compound of formula (VIII)

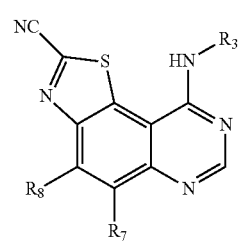

via a
Dimroth rearrangement.

* * * * *

UNITED STATES PATENT AND TRADEMARK OFFICE
CERTIFICATE OF CORRECTION

| | |
|---|---|
| PATENT NO. | : 9,446,044 B2 |
| APPLICATION NO. | : 14/238925 |
| DATED | : September 20, 2016 |
| INVENTOR(S) | : Bertrand Leblond et al. |

It is certified that error appears in the above-identified patent and that said Letters Patent is hereby corrected as shown below:

Column 4,
Line 42, "Bain eta al., *Biochem J.*, 2003, 371, 199" should read --Bain et al., *Biochem J.*, 2003, 371, 199--.

Columns 7-8,
Line 38, "Leudettines WO 2009050352 (CNRS)" should read --Leucettines WO 2009050352 (CNRS)--.

Column 14,
Line 8, "3-naphtyl," should read --β-naphtyl,--.

Column 15,
Line 60, "ahalgen" should read --a halogen--.
Lines 60-61, "unsubstitution or substitution C1-C5 alky group" should read --unsubstituted or substituted C1-C5 alkyl group--.

Column 19,
Lines 11-12, "Methyl 9-(2,4-dichorophenylamino)thiazolo[5,4-f]quinazoline-2-carbimidate 72," should read --Methyl 9-(2,4-dichlorophenylamino)thiazolo[5,4-f]quinazoline-2-carbimidate 72,--.

Column 27,
Line 23, "thiazolo[5.4-f]quinazoline-2-carbonitriles VIIIaa" should read --thiazolo[5,4-f]quinazoline-2-carbonitriles VIIIaa--.
Lines 29-30, "thiazolo[5,4-f]quinazoline-2-earbonitriles" should read --thiazolo[5,4-f]quinazoline-2-carbonitriles--.
Lines 30-31, "N-methylated-thiazolo [5,4-f]quinazoline-2-carbonitriles" should read --N-methylated-thiazolo[5,4-f]quinazoline-2-carbonitriles--.
Line 44, "VIIIab" should read --VIIIab--.

Signed and Sealed this
Sixth Day of June, 2017

Michelle K. Lee
*Director of the United States Patent and Trademark Office*

Column 31,
Line 52, "DYRK1A and DYRK1B" should read --DYRK1A and/or DYRK1B--.
Line 53, "compound Of" should read --compound of--.

Column 36,
Lines 45-46, "DMSO-$d_6$)δ8.82 (s, 1H, NH.) 7.02(d," should read
--DMSO-$d_6$) δ 8.82 (s, 1H, NH, 7.02 (d,--.
Line 47, "1H,J=2.7" should read --1H, J=2.7--.
Line 49, "$C_{12} H_{16}N_3O_2$" should read --$C_{12}H_{16}N_3O_2$--.

Column 38,
Line 29, "(DCM-EtOAc , 9:1" should read --(DCM-EtOAc, 9:1--.
Line 33, "DMSO- d $_6$)" should read --DMSO-$d_6$)--.

Column 39,
Lines 5-6, "(E)-N-(2,7-dicyanobenzo[d]thiazol-6-yl)-N,N-dimethylformimidamide" should read
--(E)-N'-(2,7-dicyanobenzo[d]thiazol-6-yl)-N,N-dimethylformimidamide--.

Column 41,
Line 15, "VIIfa" should read --VIIIfa--.

Column 43,
Line 52, "VIIIa" should read --VIIIIa--.

Column 48,
Line 3, "19F" should read --$^{19}$F--.

Column 51,
Line 18, "$v_{max/cm}^{-1}$" should read --$v_{max}$/cm$^{-1}$--.

Column 56,
Line 2, "$C_{23}H_{24}N7SClF$" should read --$C_{23}H_{24}N_7SClF$--.
Line 33, "$C_{22}H_{22}N7SClF$" should read --$C_{22}H_{22}N_7SClF$--.

Column 58,
Line 5, "δ --125.9;" should read --δ -125.9;--.

Column 61,
Line 9, "$C_1H_{15}N_6SBrF$" should read --$C_{18}H_{15}N_6SBrF$--.

Column 63,
Line 43, "$C_{22}H_{16}N7SBrF$" should read --$C_{22}H_{16}N_7SBrF$--.

Column 65,
Line 64, "VIIda" should read --VIIIda--.

Column 68,
Line 29, "88.33" should read --δ 8.33--.

Column 73,
Line 7, "6.96 (dd, 1H, J=2" should read --6.96 (dd, 1H, $J_1$=2--.
Line 7, "6.73 (dd, 1H, J=2" should read --6.73 (dd, 1H, $J_1$=2--.

Column 74,
Line 2, "$C_{18}H_{13}N6SClF$" should read --$C_{18}H_{13}N_6SClF$--.
Line 66, "$C_{17}H_2N_5OSClF$" should read --$C_{17}H_{12}N_5OSClF$--.

Column 78,
Line 39, "J=2.1" should read --$J_1$=2.1--.

Column 79,
Line 43, "VIIIa." should read --VIIIa.--.

Column 84,
Line 30, "$v_{max/cm}^{-1}$" should read --$v_{max}$/cm$^{-1}$--.
Line 66, "$C_{17}H_2N_5OSBrF$" should read --$C_{17}H_{12}N_5OSBrF$--.

Column 86,
Line 8, "$C_7H_{12}N_5OSClF$" should read --$C_{17}H_{12}N_5OSClF$--.

Column 90,
Line 23, "$C_8H_{14}N_5OSBrF$" should read --$C_{18}H_{14}N_5OSBrF$--.
Lines 25-26, "Ethyl 9-(benzo[d][1,3]dioxol-5-ylamino)thiazolo[5,4-j]quinazoline-2-carbimidate 82" should read --Ethyl 9-(benzo[d][1,3]dioxol-5-ylamino)thiazolo[5,4-f]quinazoline-2-carbimidate 82--.

Column 91,
Line 36, "thiazolo[5,4-j]quinazoline-2-carbimidate" should read --thiazolo[5,4-f]quinazoline-2-carbimidate--.

Column 94,
Line 28, "technology Worldwide" should read --technology (see Worldwide--.
Line 30, "kinase/ substrate" should read --kinase / substrate--.

Column 96,
Lines 62-67, "9-(3-Chloro-4-fluorophenylamino)-N-(2-(pyrrolidin-1-yl)ethyl)thiazolo[5,4-f]quinazoline -2-carboximidamide (compound 3); 9-(3-Chloro-4-fluorophenylamino)-N-(2-(dimethylamino)ethyl)thiazolo [5,4-f]quinazoline -2-carboximidamide (compound 4);" should read --9-(3-Chloro-4-fluorophenylamino)-N-(2-(pyrrolidin-1-yl)ethyl)thiazolo[5,4-f]quinazoline-2-carboximidamide (compound 3);
9-(3-Chloro-4-fluorophenylamino)-N-(2-(dimethylamino)ethyl)thiazolo[5,4-f]quinazoline-2-carboximidamide (compound 4);--.

Column 98,
Lines 14-16, "9-(Benzo[d][1,3]dioxol-5-ylamino)-N-(2-(dimethylamino)ethyl)thiazolo[5,4-f]quinazoline-2 -carboximidamide (compound 33);" should read --9-(Benzo[d][1,3]dioxol-5-ylamino)-N-(2-(dimethylamino)ethyl)thiazolo[5,4-f]quinazoline-2-carboximidamide (compound 33)--.

Column 100,
Line 42, "N—(C1-C3)group;" should read --N-(C1-C3)alkyl group;--.